(12) United States Patent
Cheng et al.

(10) Patent No.: US 8,906,862 B2
(45) Date of Patent: Dec. 9, 2014

(54) MULTIPLE ANTIGEN DELIVERY SYSTEM USING HEPATITIS E VIRUS-LIKE PARTICLE

(75) Inventors: R. Holland Cheng, Davis, CA (US); Li Xing, Davis, CA (US); Tatsuo Miyamura, Tokyo (JP); Yasuhiro Yasutomi, Ibaraki (JP); Tian-Cheng Li, Tokyo (JP); Naokazu Takeda, Tokyo (JP)

(73) Assignees: The Regents of the University of California, Oakland, CA (US); National Institute of Infectious Disease, Tokyo (JP); Tsukuba Primate Research Center, National Institue of Biomedical Innovation, Ibaraki (JP)

( * ) Notice: Subject to any disclaimer, the term of this patent is extended or adjusted under 35 U.S.C. 154(b) by 77 days.

(21) Appl. No.: 13/220,356

(22) Filed: Aug. 29, 2011

(65) Prior Publication Data
US 2012/0064169 A1 Mar. 15, 2012

Related U.S. Application Data

(63) Continuation-in-part of application No. PCT/US2010/025803, filed on Mar. 1, 2010.

(60) Provisional application No. 61/156,446, filed on Feb. 27, 2009, provisional application No. 61/408,501, filed on Oct. 29, 2010.

(51) Int. Cl.
| | |
|---|---|
| *A61K 38/16* | (2006.01) |
| *C07K 14/005* | (2006.01) |
| *A61K 39/29* | (2006.01) |
| *A61K 39/21* | (2006.01) |
| *A61K 39/00* | (2006.01) |

(52) U.S. Cl.
CPC ......... *A61K 39/21* (2013.01); *A61K 2039/5258* (2013.01); *A61K 2039/541* (2013.01); *A61K 2039/542* (2013.01); *C07K 14/005* (2013.01); *C07K 2319/40* (2013.01); *C12N 2740/16134* (2013.01); *C12N 2770/28142* (2013.01); *C12N 2740/16122* (2013.01); *C12N 2770/28123* (2013.01); *C12N 2740/16234* (2013.01); *A61K 39/29* (2013.01); *C12N 2770/28134* (2013.01)
USPC ....................................... 514/21.2

(58) Field of Classification Search
None
See application file for complete search history.

(56) References Cited

FOREIGN PATENT DOCUMENTS

| EP | 1331271 A1 | 7/2003 |
|---|---|---|
| EP | 1461357 A2 | 9/2004 |
| WO | 94/06913 A2 | 3/1994 |
| WO | 96/12807 A2 | 5/1996 |
| WO | 01/73078 A1 | 10/2001 |

OTHER PUBLICATIONS

Niikura et al.; "Chimeric Recombinant Hepatitis E Virus-like Particles as an Oral Vaccine Vehicle Presenting Foreign Epitopes"; *Virology*; 293:273-280 (2002).
Takamura et al.; "DNA vaccine-encapsulated virus-like particles derived from an orally transmissible virus stimulate mucosal and systemic immune responses by oral administration"; *Gene Therapy*; 11:628-635 (2004).
Wang et al.; "Crystallization and preliminary X-ray diffraction analysis of recombinant hepatitis E virus-like particle"; *Acta Cryst.*; F64:318-322 (2008).
International Search Report and Written Opinion from PCT/US2010/025803, dated May 27, 2010.
Niikura, M., "Hepatitis E virus-like particles as mucosal vaccine carriers," presentation reference, Simon Fraser University, pp. 1-29, May 16, 2008.
Extended European Search Report dated Jan. 23, 2014 for European Patent Application No. 10746985.0, 12 pages.
Kui et al., "The expression, purification, and immunogenicity of a new chimeric virus-like particle", *Viral Immunology*, 22(1): 49-56 (2009).
Renoux et al., "Induction of antibody response against hepatitis E virus (HEV) with recombinant human papillomavirus pseudoviruses expressing truncated HEV capsid proteins in mice", *Vaccine*, 26 (51): 6602-6607 (2008).
Li et al., "Essential elements of the capsid protein for self-assembly into empty virus-like particles of hepatitis E virus", *Journal of Virology*, 79(20): 12999-13006 (2005).
Zhou et al, "A truncated ORF2 protein contains the most immunogenic site on ORF2: antibody responses to non-vaccine sequences following challenge of vaccinated and non-vaccinated macaques with hepatitis E virus", *Vaccine*, 23 (24): 3157-3165 (2005).
Li et al., "Recombinant subunit ORF2.1 antigen and inudction of anytibody against immunodominant epitopes in the hepatitis E virus capsid proten", *Journal of Medical Virology*, 60(4): 379-386 (2000).
Li et al., "Expression and self-assembly of empty virus-like particles of hepatitis E virus", *Journal of Virology*, 71(10): 7207-7213 (1997).
Final Office Action mailed Dec. 27, 2013 for U.S. Appl. No. 13/224,151, 24 pages.
Non-Final Office Action mailed Jun. 20, 2013 for U.S. Appl. No. 13/224,151, 15 pages.
Yasutomi, *Clinical Virology* (RinshoToUirusu), 32:362-371 (2004).
Takamura et al., "DNA vaccine-encapsulated virus-like particles derived from an orally transmissible virus stimulate mucosal and systemic immune responses by oral administration", *Gene Ther.*, 11:628-635 (2004).
Yasutomi et al., *Clinical Immunology* (Rinsho Men'eki), 43(6):635-639.
Notice of Reasons for Rejection mailed on Jul. 8, 2014 for Japanese Patent Application No. 2011-552226, with translation, 8 pages.
Notice of Allowance issued on Aug. 5, 2014 for U.S. Appl. No. 13/224,151, 11 pages.

*Primary Examiner* — Thomas Heard
(74) *Attorney, Agent, or Firm* — Kilpatrick Townsend & Stockton LLP

(57) ABSTRACT

This invention provides a peptide/nucleic acid composition for oral/mucosal, dual-modal activation of immune protection systems.

16 Claims, 39 Drawing Sheets

```
525          .         .         .         .
PLSTIQQYSKTFFVLPLRGKLSFWE
----EEE-----EEE-----------HHH

550          .         .         .         .
AGTTKAGYPYNYNTTASDQLLVENA
H---------------------EEEE--

575          .         .         .         .
AGHRVAISTYTTSLGAGPVSISAVA
----EEEE----------HHHHHHHH

600          .
VLAPHSALA
HH--HHHH-
```

FIG. 8

MULTIPLE ANTIGEN DELIVERY SYSTEM USING HEPATITIS E VIRUS-LIKE PARTICLE

CROSS-REFERENCES TO RELATED APPLICATIONS

This application is a continuation-in-part of PCT/US2010/025803, filed Mar. 1, 2010, which claims priority to U.S. Provisional Patent Application No. 61/156,446, filed Feb. 27, 2009. This application also claims priority to U.S. Provisional Patent Application No. 61/408,501, filed Oct. 29, 2010. The contents of each of the above are hereby incorporated by reference in the entirety for all purposes.

BACKGROUND OF THE INVENTION

HEV is an ss(+)RNA virus causing self-limited hepatitis in human. When expressed in insect Tn5 cells, the truncated capsid protein (CP) covering residues 112-608 is able to self-assemble into virus-like particle (VLP). The VLP is smaller than the HEV native virion and contain no HEV genomic RNA. The VLP itself induces efficiently the immunity in chimpanzee against the challenge of HEV virus without adjuvant. The structure of this HEV VLP has recently been achieved in atomic resolution by the present inventors to elucidate that HEV CP is composed of three major domains, S1, S2, and P, with epitope presentation and capsid assembly modularized in independent modalities (Wang et al., 2008. Acta Crystallographica F, Acta Cryst. F 64, 318-322; Xing et al., 1999. Virology 265, 35-45). HEV VLP is a potential carrier of mucosal vaccine for the presentation of antigenic epitopes through oral administration. The chimeric CP, with an insertion of 11 amino acids of a B-cell epitope tag at the C-terminus of a truncated CP, still forms icosahedral particle. After oral administration, this HEV chimeric VLP is able to stimulate humoral immune response and significant level of IgM and IgG antibodies to the inserted epitope and HEV were observed in intestinal secretions (Niikura et al., 2002. Virology 293, 273-280). Importantly, the HEV VLP can disassemble and reassemble in vitro with the ability of encapsidating DNA plasmids. With this method, the HEV VLP is demonstrated to deliver DNA plasmid encoding human immunodeficiency virus (HIV) gp120 into the intestinal mucosa. Significant level of specific IgG and IgA to HIV env was found in fecal extracts and sera of testing experimental animal. Moreover, mice used in the study exhibited CTL response specific to gp120 in the spleen, Payer's patches and mesenteric lymph modes. (Takamura, S., et al., 2004. Gene Ther 11, 628-63.) In summary, these data demonstrate that the HEV VLP is capable of delivering both amino acid antigens and DNA encoding the antigens to or conferring immunity to mucosal tissue by oral administration.

BRIEF SUMMARY OF THE INVENTION

The present invention provides a composition comprising a modified hepatitis E virus (HEV) capsid protein and a heterologous nucleic acid encapsulated in a chimeric virus-like particle (VLP) formed by the modified HEV capsid protein. The modified HEV capsid comprises a portion of HEV ORF 2 protein and a heterologous peptide. In some embodiments, the heterologous nucleic acid and the heterologous peptide are from the same source. In some embodiments, the heterologous nucleic acid and the heterologous peptide are from different sources. In some embodiments, the modified HEV capsid protein comprises a portion of HEV ORF 2 protein and two or more heterologous peptides. The two or more heterologous peptides can be from the same source or from different sources.

In one embodiment of the invention, the modified HEV capsid protein of the composition of the present invention comprises residues 112-608 of HEV ORF 2 protein. For example, the modified HEV capsid comprises residues 112-608 of HEV ORF 2 protein and a heterologous peptide. In another embodiment of the invention, the modified HEV capsid protein further comprises residues 91-123 of HEV ORF 3 protein fused to the N-terminal of residues 112-608 of the HEV ORF 2 protein. In other embodiments of the invention, the modified HEV capsid protein further comprises residues 70-123 of HEV ORF 3 protein fused to the N-terminal of residues 112-608 of the HEV ORF 2 protein. For instance, a modified HEV capsid can also be a fusion protein of residues 112-608 of the HEV ORF 2 protein and residues 70-123/91-123 of the HEV ORF 3 protein and a heterologous peptide.

In some embodiments of the invention, the heterologous peptide is located at the C-terminal of the modified HEV capid protein. In some embodiments of the invention, the heterologous peptide is located at the N-terminal of the modified HEV capid protein.

In some embodiments of the invention, the heterologous peptide is inserted into HEV ORF 2 protein of the modified HEV capid protein within a pre-selected region selected from a group consisting of residues 483-490, residues 530-535, residues 554-561, residues 573-577, residues 582-593, and residues 601-613. In other embodiments of the invention, at least one residue of the pre-selected region is deleted. In some cases, all residues within the pre-selected region are deleted.

The compositions of the present invention may further comprise a pharmaceutically acceptable excipient. The excipient may be suitable for oral delivery of the composition. Alternatively, the exicipient may be adapted for mucosal delivery of the composition. In some embodiments of the invention, the exicipient is an adjuvant.

The present invention further provides a method of inducing an immunogenic response in a host, comprising the step of administering to the host an effective amount of the composition of this invention.

The present invention also relates to a modified hepatitis E virus (HEV) capsid protein and polynucleotides encoding such protein. The modified hepatitis E virus (HEV) capsid protein comprises a portion of HEV ORF 2 protein and a heterologous peptide inserted into the portion of HEV ORF 2 within a pre-selected region of residues 483-490, residues 530-535, residues 554-561, residues 573-577, residues 582-593, or residues 601-613 of the HEV ORF 2 protein.

In an additional aspect, the present invention provides a means for delivery of therapeutics, especially to various mucosal tissues. For instance, the VLPs of this invention may be used to encapsulate and deliver an agent for therapeutic purpose. The capsid proteins forming the VLPs may comprise only portions or full length of the HEV protein such as ORF2 or ORF3 or may comprise a portion of a heterologous protein. The therapeutic agent may be of any chemical nature, including small molecules or macromolecules.

BRIEF DESCRIPTION OF THE DRAWINGS

FIG. 8 HEV-VLP having a chimerized epitope with a DNA vaccine encapsulated.

DETAILED DESCRIPTION OF THE INVENTION

I. Introduction

Figure 1:
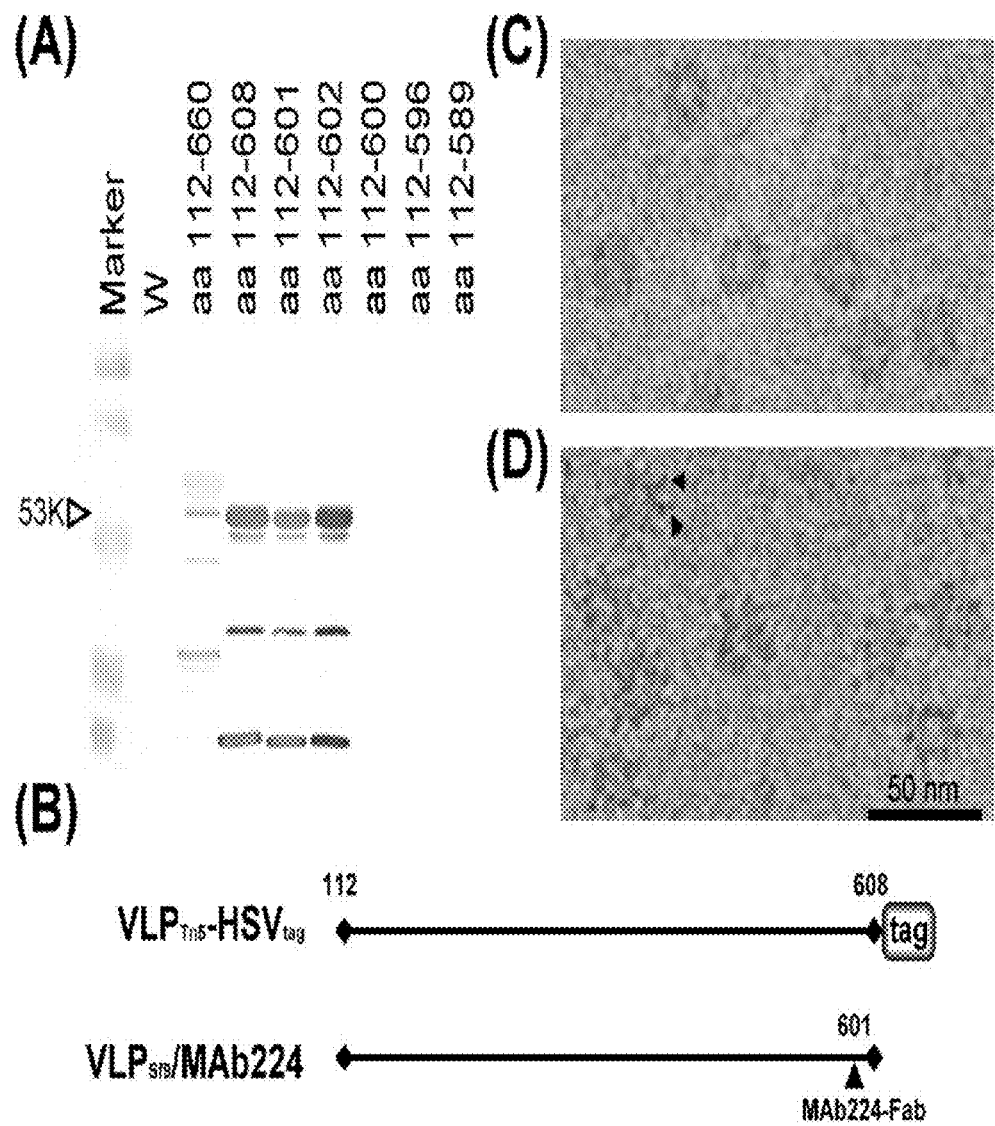
FIG. 1 Characterization of VLP/C-tag and VLP/MAb224. (A) Western blotting assay of the C-terminally truncated ORF2 proteins with MAb224. M, molecular weight markers; W, wild-type baculovirus-infected cells. (B) Diagram of the C-terminal markers. Electron micrographs of frozen-hydrated VLP/C-tag (C) and VLP/MAb224 (D). Both particles show an absence of density in the center of particles. Note the surface of VLP/MAb224 showed longer thorn-like densities compared to VLP/C-tag. Scale bar presents 50 nm.

The present invention relates to an HEV VLP-based peptide/nucleic acid (P/N) system. The idea of using HEV VLP-based P/N system provides several unique advantages, besides inducing immune response via both MHC class I and II system. 1) the P/N system provides the possibility of oral vaccination. Practically, oral administration is less stressful and does not require professional skill. Besides, delivery of vaccine through intestinal tract is considered safer than systemic injection. The nature infection route of HEV and the structure of HEV VLP provide resistance to hash environments in the digestive tracts, such as low pH in the stomach, the presence of proteolytic enzymes, and the presence of physical and biochemical barriers associated with the mucosal surface. 2) the HEV VLP can be produced from standard cultivation protocols and the yield of purified HEV-VLPs can be 50-100 µg/ml, about 100 times greater compared to other VLPs. 3) the HEV VLP deliver amino acid immunogen in the form of icosahedral particles, ie, every successfully entered particle brings in 60 copies of immunogen to the same host cell. 4) anti-HEV immune responses are proven to have no effect on both DNA administration and peptide immunogen vaccination. 5) the HEV is stable at room temperature. By combining all the features, we therefore anticipate the P/N system would accomplish our goal of develop efficacious and broadly reactive vaccine.

II. Definitions

"Hepatitis E virus" or "HEV" refers to a virus, virus type, or virus class, which i) causes water-borne, infectious hepatitis; ii) distinguishes from hepatitis A virus (HAV), hepatitis B virus (HBV), hepatitis C virus (HCV), or hepatitis D virus (HDV) in terms of serological characteristics; iii) contains a genomic region that is homologous to a 1.33 kb cDNA inserted in pTZKF1(ET1.1), a plasmid embodied in a *E. coli* strain deposited in American Type Culture Collection (ATCC) with accession number 67717.

The terms "capsid protein" or "modified capsid protein", with reference to HEV, refer to a mature or modified ORF2 or ORF 3 polypeptide. As used herein, reference to such ORF 2 or ORF 3 polypeptides or proteins is meant to include the full-length polypeptide, and fragments thereof, and also include any substitutions, deletions, or insertions or other modifications made to the ORF 2 or ORF 3 proteins.

As used herein, the term "virus-like particle" (VLP) refers to a structure that in at least one attribute resembles a virus but is not infectious due to the lack of a viral genome. "VLP" refers to a nonreplicating viral shell, preferably derived from hepatitis E virus proteins such as capsid proteins. VLPs are generally composed of one or more viral proteins, including, but are not limited to those proteins referred to as Hepatitis E capsid proteins, or modified hepatitis E virus capsid protein. VLPs can form spontaneously upon recombinant expression of the protein in an appropriate expression system.

The term "heterologous nucleic acid," as used herein, refers to a nucleic acid not endogenous to the hepatitis E virus, i.e., from a source other than HEV. The term "heterologous polypeptide," as used herein, refers to a peptide or polypeptide not endogenous to the hepatitis E virus, or a peptide or polypeptide to a protein or peptide coded for by a DNA sequence which is not endogenous to the native genome of hepatitis E virus, i.e., from a source or organism other than HEV.

The term "encapsulation," or "encapsulated," as used herein refers to the envelopment of a heterologous substance, such as a heterologous nucleic acid, within the virus-like particles defined herein.

The term "chimeric protein" refers to an amino acid sequence having two or more parts that generally are not found together in an amino acid sequence in nature. The term "chimeric virus-like particle" refers to a virus-like particle comprising HEV capsid proteins and one or more heterologous peptide. As defined herein, the term "chimeric virus-like particle" further refers to a virus-like particle comprising an HEV capsid protein and a heterologous peptide encapsulating one or more heterologous nucleic acids.

As defined herein, the term "source" refers to a pathogen. The term "source" may also refers to the cells derived from diseased tissues, e.g., tissues of a cancer, infectious disease, allergic reaction, or autoimmune disease. Pathogens include, for example, a bacterium, virus, protozoan, fungus, parasite, or infectious particle, such as a prion. Examples of pathogens further include Adenoviradae; Arenaviridae (for example, Ippy virus and Lassa virus); Birnaviridae; Bunyaviridae; Caliciviridae; Coronaviridae; Filoviridae; Flaviviridae (for example, yellow fever virus, dengue fever virus and hepatitis C virus); Hepadnaviradae (for example, hepatitis B virus); Herpesviradae (for example, human herpes simplex virus 1); Orthomyxoviridae (for example, influenza virus A, B and C); Paramyxoviridae (for example, mumps virus, measles virus and respiratory syncytial virus); Picornaviridae (for example, poliovirus and hepatitis A virus); Poxviridae; Reoviridae; Retroviradae (for example, BLV-HTLV retrovirus, HIV-I, HIV-2, bovine immunodeficiency virus and feline immunodeficiency virus); Rhabodoviridae (for example, rabies virus), and Togaviridae (for example, rubella virus). In one embodiment, the products comprise one or more antigens derived from a major viral pathogen such as the various hepatitis viruses, polio virus, human immunodeficiency virus (HIV), various influenza viruses, West Nile virus, respiratory syncytial virus, rabies virus, human papilloma virus (HPV), Epstein Barr virus (EBV), polyoma virus, or SARS coronavirus. Specific examples of hepatitis viruses include, e.g., hepatitis A virus (HAV), hepatitis B virus (HBV), hepatitis C virus (HCV), delta hepatitis virus (HDV), hepatitis E virus (HEV) and hepatitis G virus (HGV); Specific examples of herpesvirus family include herpes simplex virus (HSV) types 1 and 2. Pathogens further include agents causing diseases such as diptheria (e.g., *Corynebacterium diphtherial*), pertussis (e.g., *Bordetella pertussis*), tetanus (e.g., *Clostridium tetan*?), tuberculosis (e.g., *Mycobacterium tuberculosis*), bacterial or fungal pneumonia, cholera (e.g., *Vibrio cholerae*), typhoid fever (e.g., *S. typhi*), plague, shigellosis (e.g., *Shigella dysenteriae serotype* 1 (*S. dysenteriae* I)), Salmonellosis, Legionnaire's disease (e.g., *Legionella pneumophila*), Lyme disease, leprosy (e.g., *Mycobacterium leprae*), malaria (e.g., *Plasmodium falciparum*), Hookworm, Onchocerciasis, Schistosomiasis, Trypamasomialsis, leishmaniasis, giardia (e.g., *Giardia lamblia*), Amoebiasis (e.g., *Entamoeba histolytica*), Filariasis, Borrelia, Trichinosis, influenza, hepatitis B and C, meningococcal meningitis, community acquired pneumonia, chickenpox, rubella, mumps, measles, AIDS, dengue respiratory infections, diarrhoeal diseases, tropical parasitic diseases, sexually transmitted diseases and chlamydia infections. Antigenic material may also be derived from causative agents responsible for new emerging, re-emerging diseases or bioterrorism diseases such as: SARS infection, Vancomycin-resistant *S. aureus* infections, West Nile Virus infections, Cryptosporidiosis, Hanta virus infections, Epstein Barr virus infections, Cytomegalovirus infections, H5N1 influenza, Enterovirus 71 infections, *E coli*. O157:H7 infections, human monkey pox, Lyme disease, Cyclosporiasis, Hendra virus infections, Nipah virus infections, Rift Valley fever, Marburg haemorrhagic fever, Whitewater arrollo virus infections and Anthrax.

As defined herein, the term "same source" refers to the fact that a heterologous nucleic acid and a heterologous peptide (or two or more heterologous peptides) are derived from the same organism, such as a disease-causing pathogen including virus, bacterium, etc. The "same source" encompasses mutated or modified forms of the pathogen, such as different strains of a virus or bacterium.

A "pharmaceutically acceptable" or "pharmacologically acceptable" material is one that is not biologically harmful or otherwise undesirable, i.e., the material may be administered to an individual along with the modified hepatitis E virus capsid protein or the chimeric virus-like particles or the compositions of the present invention without causing any undesirable biological effects. Neither would the material interact in a deleterious manner with any of the components of the composition in which it is contained.

The term "excipient" refers to any essentially accessory substance that may be present in the finished dosage form of the composition of this invention. For example, the term "excipient" includes vehicles, binders, disintegrants, fillers (diluents), lubricants, glidants (flow enhancers), compression aids, colors, sweeteners, preservatives, suspending/dispersing agents, film formers/coatings, flavors and printing inks.

The term "adjuvant" refers to a compound that, when administered in conjunction with an antigen, augments the immune response to the antigen, but does not generate an immune response to the antigen when administered alone. Adjuvants can augment an immune response by several mechanism including lymphocyte recruitment, stimulation of B and/or T cells, and stimulation of macrophages.

An "immunogenic response" to an antigen or composition is the development in a subject of a humoral and/or a cellular immune response to an antigen present in the composition of interest. For purposes of the present disclosure, a "humoral immune response" refers to an immune response mediated by antibody molecules, while a "cellular immune response" is one mediated by T-lymphocytes and/or other white blood cells. One important aspect of cellular immunity involves an antigen-specific response by cytolytic T-cells ("CTL"s). CTLs have specificity for peptide antigens that are presented in association with proteins encoded by the major histocompatibility complex (MHC) and expressed on the surfaces of cells. CTLs help induce and promote the destruction of intracellular microbes, or the lysis of cells infected with such microbes. Another aspect of cellular immunity involves an antigen-specific response by helper T-cells. Helper T-cells act to help stimulate the function, and focus the activity of, non-specific effector cells against cells displaying peptide antigens in association with MHC molecules on their surface. A "cellular immune response" also refers to the production of cytokines, chemokines and other such molecules produced by activated T-cells and/or other white blood cells, including those derived from CD4+ and CD8+ T-cells. Hence, an immunological response may include one or more of the following effects: the production of antibodies by B-cells; and/or the activation of suppressor T-cells and/or γΔ T-cells directed specifically to an antigen or antigens present in the composition or vaccine of interest. These responses may serve to neutralize infectivity, and/or mediate antibody-complement, or antibody dependent cell cytotoxicity (ADCC) to provide protection to an immunized host. Such responses can be determined using standard immunoassays and neutralization assays, well known in the art.

As used herein, the term "host" refers to humans as well as other animals.

The term "mucosal delivery" relates to delivery of a composition to a mucous membrane, such as the mucosa of the gastro-intestinal tract (e.g., the buccal or labial mucosa) or the mucosa of the respiratory tract (e.g., the nasal mucosa).

III. Hepatitis E Virus Capsid Protein

Hepatitis E virus (HEV) is known to cause severe acute liver failure. HEV belongs to the genus Hepevirus in the family Hepeviridae. HEV contains a single-stranded positive-sense RNA molecule of approximately 7.2-kb. The RNA is 3' polyadenylated and includes three open reading frames (ORF). ORF1 encodes viral nonstructural proteins, located in the 5' half of the genome. ORF2 encodes a protein-forming viral capsid, located at the 3' terminus of the genome. ORF3 encodes a 13.5-kDa protein, overlapped with C-terminus of ORF1 and N-terminus of ORF2. ORF3 is associated with the membrane as well as with the cytoskeleton fraction.

III. Virus-Like Particles (Vlps)

One aspect of the invention relates to construction of HEV capsid protein for self-assembly into virus-like particles (VLPs). Various constructs of capsid protein can be used for formation of VLPs (Expression and self-assembly of empty virus-like particles of hepatitis E virus. Li TC, Yamakawa Y, Suzuki K, Tatsumi M, Razak M A, Uchida T, Takeda N, Miyamura T., J Virol. 1997 October; 71(10):7207-13. Essential elements of the capsid protein for self-assembly into empty virus-like particles of hepatitis E virus. Li T C, Takeda N, Miyamura T, Matsuura Y, Wang J C, Engvall H, Hammar L, Xing L, Cheng R H. J Virol. 2005 October; 79(20):12999-3006.). An HEV capsid protein comprising HEV ORF 2 protein can be used as a construct for formation of VLPs in vitro, since HEV's major capsid protein is encoded by ORF 2 gene. Preferably, an HEV capsid protein comprising a portion of HEV ORF 2 protein can be used as a construct for formation of VLPs in vitro. Optionally, an HEV capsid protein comprising a portion of HEV ORF 2 protein and a portion of HEV ORF 3 protein can be used as a construct for formation of VLPs in vitro. HEV ORF 2 is a protein of 660 residues having the following amino acid sequence:

(SEQ ID NO: 1; GenBank Accession No: AAA45736.1)
```
MRPRP ILLLL LMFLP MLPAP PPGQP SGRRR GRRSG GSGGG FWGDR VDSQP

FAIPYI HPTNP FAPDV TAAAG AGPRV RQPAR PLGSA WRDQA QRPAV ASRRR

PTTAG AAPLT AVAPA HDTPP VPDVD SRGAI LRRQY NLSTS PLTSS VATGT NLVLY

AAPLS PLLPL QDGTN THIMA TEASN YAQYR VARAT IRYRP LVPNA VGGYA ISISF

WPQTT TTPTS VDMNS ITSTD VRILV QPGIA SELVI PSERL HYRNQ GWRSV ETSGV

AEEEA TSGLV MLCIH GSLVN SYTNT PYTGA LGLLD FALEL EFRNL TPGNT NTRVS

RYSST ARHRL RRGAD GTAEL TTTAA TRFMK DLYFT STNGV GEIGR GIALT LFNLA

DTLLG GLPTE LISSA GGQLF YSRPV VSANG EPTVK LYTSV ENAQQ DKGIA IPHDI

DLGES RVVIQ DYDNQ HEQDR PTPSP APSRP FSVLR ANDVL WLSLT AAEYD QSTYG

SSTGP VYVSD SVTLV NVATG AQAVA RSLDW TKVTL DGRPL STIQQ YSKTF FVLPL

RGKLS FWEAG TTKAG YPYNY NTTAS DQLLV ENAAG HRVAI STYTT SLGAG PVSIS

AVAVL APHSA LALLE DTLDY PARAH TFDDF CPECR PLGLQ GCAFQ STVAE LQRLK

MKVGK TREL
```

Some constructs of the invention are fusion proteins of a portion of HEV ORF 2 protein and a heterologous peptide. Some constructs of the invention are HEV capsid proteins comprising HEV ORF 2 protein with deletions at the N-terminal region. Some novel constructs of the invention are HEV capsid proteins comprising HEV ORF 2 proteins having a deletion of at least contiguous 10 amino acids at the N-terminal region. Some novel constructs of the invention are HEV capsid proteins comprising HEV ORF 2 protein having a deletion of at least contiguous 25 amino acids at the N-terminal region, preferably having a deletion of at least contiguous 50 amino acids, and particularly preferably having a deletion of at least contiguous 100 amino acids. Preferred constructs of the invention are HEV capsid proteins comprising HEV ORF 2 proteins having a deletion of 111 to 124 residues at the N-terminal region. Particularly preferred constructs of the invention are HEV capsid proteins comprising HEV ORF 2 proteins having a deletions of 1-111 at the N-terminal region.

Some constructs of the invention are fusion proteins of a portion of HEV ORF 2 protein and a heterologous peptide. Some constructs of the invention are HEV capsid proteins comprising HEV ORF 2 protein with deletions at the C-terminal region. Some novel constructs of the invention are HEV capsid proteins comprising HEV ORF 2 proteins having a deletion of at least contiguous 10 amino acids at the C-terminal region. Some novel constructs of the invention are HEV capsid proteins comprising HEV ORF 2 protein having a deletion of at least contiguous 20 amino acids at the C-terminal region, preferably having a deletion of at least contiguous 30 amino acids, and particularly preferably having a deletion of at least contiguous 50 amino acids. Preferred constructs of the invention are HEV capsid proteins comprising HEV ORF 2 proteins having a deletion of 52 to 60 residues at the C-terminal region. Particularly preferred constructs of the invention are HEV capsid proteins comprising an HEV ORF 2 protein having a deletion of 609-660, 601-660, 602-660, 603-660, 604-660, 605-660, 606-660, 607-660, 608-660, or 609-660 at the C-terminal region.

Some constructs of the invention are fusion proteins of a portion of HEV ORF 2 protein and a heterologous peptide. Some constructs of the invention are HEV capsid proteins comprising HEV ORF 2 protein with deletions at both the N-terminal region and the C-terminal region. Some novel constructs of the invention are HEV capsid proteins comprising HEV ORF 2 proteins having a deletion of at least contiguous 10 amino acids at the N-terminal region and a deletion of at least contiguous 10 amino acids at the C-terminal region. Some novel constructs of the invention are HEV capsid proteins comprising HEV ORF 2 proteins having a deletion of at least contiguous 25 amino acids at the N-terminal region and a deletion of at least contiguous 20 amino acids at the C-terminal region. Some novel constructs of the invention are HEV capsid proteins comprising HEV ORF 2 proteins having a deletion of at least contiguous 50 amino acids at the N-terminal region and a deletion of at least contiguous 30 amino acids at the C-terminal region. Some novel constructs of the invention are HEV capsid proteins comprising HEV ORF 2 proteins having a deletion of at least contiguous 100 amino acids at the N-terminal region and a deletion of at least contiguous 50 amino acids at the C-terminal region. Preferred constructs of the invention are HEV capsid proteins comprising HEV ORF 2 proteins having a deletion of 111 to 124 residues at the N-terminal region and a deletion of 52 to 60 residues at the C-terminal region. Particularly preferred constructs of the invention are HEV capsid proteins comprising residues 112-608 of HEV ORF 2.

Another aspect of the invention relates to the construction of HEV capsid protein for self-assembly into virus-like particles (VLPs), using a portion of HEV ORF 3 protein fused to the N-terminal of a portion of HEV ORF 2 protein. HEV ORF 3 is a protein of 123 residues having the following amino acid sequence:

(SEQ ID NO: 2; GenBank Accession No: AAA45726.1)
```
MNNMS FAAPM GSRPC ALGLF CCCSS CFCLC CPRHR PVSRL AAVVG

GAAAV PAVVS GVTGL ILSPS QSPIF IQPTP SPPMS PLRPG LDLVF ANPPD HSAPL

GVTRP SAPPL PHVVD LPQLG PRR
```

According to the present invention, a portion of HEV ORF 3 can be fused to the N-terminal of any HEV ORF 2 construct described above. HEV ORF 3 fusion useful for the present invention comprises the C-terminal region of HEV ORF 2, including the dimerization essential region of residues 81-123 of ORF 3. Some novel constructs of the invention are HEV capsid proteins comprising at least 60 residues of the C-terminal of HEV ORF 3 protein fused to the N-terminal of a portion of HEV ORF 2 protein. Some novel constructs of the invention are HEV capsid proteins comprising at least 70 residues of the C-terminal of HEV ORF 3 protein fused to the N-terminal of a portion of HEV ORF 2 protein, preferably comprising at least 80 residues of the C-terminal of HEV ORF 3 protein fused to the N-terminal of a portion of HEV ORF 2 protein, and particularly preferably comprising at least 90 residues of the C-terminal of HEV ORF 3 protein fused to the N-terminal of a portion of HEV ORF 2 protein. Preferred constructs of the invention are HEV capsid proteins comprising residues 91-123 of HEV ORF 3 protein fused to the N-terminal of a portion of HEV ORF 2 protein. Particularly preferred constructs of the invention are HEV capsid proteins comprising residues 70-123 of HEV ORF 3 protein fused to the N-terminal of a portion of HEV ORF 2 protein.

IV. Chimeric Recombinant Hev Virus-Like Particles

One aspect of the invention relates to a modified hepatitis E virus capsid protein for self-assembly into virus-like particles (VLPs) using the various constructs of capsid protein fused with a heterologous peptide as described in section III above.

In some embodiments of the invention, the heterologous peptide is located at the C-terminal of the modified HEV capsid protein. In some embodiments of the invention, the heterologous peptide is located at the N-terminal of the modified HEV capsid protein. Preferably the insertion of the heterologous peptide at the C-terminal or the N-terminal of the modified HEV capsid protein does not disrupt the self-assembly of the VLP. More preferably, the inserted heterologous peptide is exposed to the surface of the VLP for presentation of the heterologus peptide as an antigenic epitope. The length of the heterologous peptide is preferably chosen to be compatible with the formation of VLP. In general, the heterologous peptide can be 3 or 4 amino acids in length, more typically, 5,6, or 7 amino acids in length, more typically 8 or 9 amino acids in length, and even more typically 10 or more amino acids in length.

In other embodiments of the invention, the heterologous peptide of the present invention can also be inserted into HEV ORF 2 protein of the modified HEV capsid protein within a pre-selected region. Any region within HEV ORF 2 protein of the modified HEV capsid protein can be selected for insertion of the heterologous peptide. Preferably the insertion of the heterologous peptide at the pre-selected region of the modified HEV capsid protein does not disrupt the self-assembly of the VLP. More preferably, the inserted heterologous peptide is exposed to the surface of the VLP for presentation of the heterologus peptide as an antigenic epitope. Particularly preferably, the pre-selected region is a loop region of HEV ORF 2, wherein the loop region is exposed on the surface of the VLP. Most preferably, the pre-selected region is one of the following loop regions: residues 483-490, residues 530-535, residues 554-561, residues 573-577, residues 582-593, and residues 601-613. The length of the heterologous peptide is preferably chosen to be compatible with the formation of VLP. In general, the heterologous peptide can be 3 or 4 amino acids in length, more typically, 5,6, or 7 amino acids in length, more typically 8 or 9 amino acids in length, and even more typically 10 or more amino acids in length.

When the heterologous peptide is inserted into a pre-selected region of HEV ORF 2 protein of the modified HEV capsid protein, deletions within the pre-selected region can be made to accommodate the insertion of the heterologous peptide. Necessary deletions of the pre-selected region can be made to maintain the folding of the capsid protein, to facilitate the self-assembly of the VLP, and to maintain or enhance the stability of the VLP. Necessary deletions can also be made to allow longer heterologous insertions, particularly in cases of presenting a conformational epitope.

In some embodiments of the invention, at least one residue of the pre-selected region is deleted. In other embodiments of the invention, all residues of the pre-selected region are deleted. In preferred embodiments of the invention, the number of the residues deleted from the pre-selected region is the same or about the same as the number of the residues of the inserted heterologous peptide.

A skilled artisan would readily recognize that more than one antigen can be made by incorporating more than one heterologous peptides in the modified HEV capsid protein. For example, a first heterologous peptide may be inserted at the C-terminal of the modified HEV capsid protein, and a second heterologous peptide may be inserted into a pre-selected region.

The present invention also provide a polynucleotide encoding the modified HEV capsid protein or polypeptide as described herein.

V. Production And Purification Of Virus-Like Particles

One aspect of the invention relates to methods for production and purification of virus-like particles (See, Expression and self-assembly of empty virus-like particles of hepatitis E virus. Li T C, Yamakawa Y, Suzuki K, Tatsumi M, Razak M A, Uchida T, Takeda N, Miyamura T., J Virol. 1997 October; 71(10):7207-13. Essential elements of the capsid protein for self-assembly into empty virus-like particles of hepatitis E virus. Li T C, Takeda N, Miyamura T, Matsuura Y, Wang J C, Engvall H, Hammar L, Xing L, Cheng R H. J Virol. 2005 October; 79(20):12999-3006. Niikura M et al, Chimeric recombinant hepatitis E virus-like particles as an oral vaccine vehicle presenting foreign epitopes. Virology 2002; 293: 273-280). Various expression systems can be used to express the modified hepatitis E virus capsid protein of the present invention. Examples of expression systems useful for the production of virus-like particles of the present invention include, but are not limited to, bacterial expression system (e.g., *Escherichia coli*), insect cells, yeast cells and mammalian cells. Preferred expression system of the present invention includes baculovirus expression systems using insect cells. General methods, for example, for handling and preparing baculovirus vectors and baculoviral DNA, as well as insect cell culture procedures, are outlined in A Manual of Methods for Baculovirus Vectors and Insect Cell Culture Procedures.

The modified hepatitis E virus capsid protein of the present invention can be cloned into the baculovirus vector, and used to infect appropriate host cells (see, for example, O'Reilly et al., "Baculovirus Expression Vectors: A Lab Manual," Freeman & Co. 1992.). An insect cell line (e.g., Sf9 or Tn5) can be transformed with a transfer vector containing polynucleic acids which encodes the modified HEV capsid proteins of the invention. The transfer vector includes, for example, linearized baculovirus DNA and a plasmid containing the desired polynucleotides. The host cell line may be co-transfected with the linearized baculovirus DNA and a plasmid in order to make a recombinant baculovirus.

Purification of the virus-like particles of the present invention can be carried out according to the standard technique in the art (See, Li T C, et al., J Virol. 1997 October; 71(10):7207-

13. Li T C, et al., J Virol. 2005 October; 79(20):12999-3006. Niikura M et al, Virology 2002; 293: 273-280). The purified VLPs are then resuspended in a suitable buffer.

VI. Encapsulation Of Heterologous Nucleic Acids

Another aspect of the invention relates to the encapsulation of a heterologous nucleic acid in HEV virus-like particles (See, DNA vaccine-encapsulated virus-like particles derived from an orally transmissible virus stimulate mucosal and systemic immune responses by oral administration, Gene Therapy 2004. 11, 628-635. S Takamura, M Niikura, T-C Li, N Takeda, S Kusagawa, Y Takebe, T Miyamura and Y Yasutomi). Any standard technique in the art can be used to encapsulate a heterologous nucleic acid into the VLPs of the present invention. The general procedure involves (1) disassembling the VLPs formed by the modified HEV capsid protein according to the present invention; and (2) reconstructing the VLPs in the presence of a heterologous nucleic acid. A skilled artisan would recognize that it is preferred to have purified VLPs before the encapsulation procedure. It is particularly preferred to have the VLPs depleted of, or substantially depleted of, any undesired nucleic acids before the encapsulation procedure.

Disassembly of VLPs can be carried out using any standard technique in the art. Reconstituted virus-like particle can be produced under physiological conditions (See, US Patent Publication No.: 20080131928). Often, disassembly of virus-like particles require an agent to disrupt the assembly of VLPs, such as a reducing agent or a chelating agent (See, US Patent Publication No.: 20040152181). A skilled artisan would recognize that factors and conditions that affect assembly and disassembly include: pH, ionic strength, posttranslational modifications of viral capsid proteins, disulfide bonds, and divalent cation bonding, among others. For example, the importance of cation bonding, specifically calcium, in maintaining virion integrity has been shown for polyomavirus (Brady et al., J. Virol, 23:717-724, 1977), and rotovirus (Gajardo et al., J. Virol, 71:2211-2216, 1997). Also, disulfide bonds appear to be significant for stabilizing polyomavirus (Walter et al., Cold Spring Har Symp. Quant. Biol, 39:255-257, 1975; Brady et al., J. Virol, 23:717-724, 1977); and SV40 viruses (Christansen et al., J. Virol, 21:1079-1084, 1977). Also, it is known that factors such as pH and ionic strength influence polyomavirus capsid stability, presumably by affecting electrostatic interactions (Brady et al., J. Virol, 23:717-724, 1977; Salunke et al., Cell, 46:895-904, 1986; Salunke et al., Biophys. J, 56:887-900, 1980). Also, it is known that post-translational modifications of some viral capsid proteins may affect capsid stability and assembly, e.g., glycosylation, phosphorylation, and acetylation (Garcea et al., Proc. Natl. Acad. Sci. USA, 80:3613-3617, 1983; Xi et al., J. Gen. Virol, 72:2981-2988, 1991). Thus, there are numerous interrelated factors which may affect capsid stability, assembly and disassembly.

Preferably, the VLPs of the present invention is disassembled by the removal of calcium ions (See, Touze A, Coursaget P. In vitro gene transfer using human papillomavirus-like particles. Nucleic Acids Res 1998; 26:1317-1323; Takamura et al., DNA vaccine-encapsulated virus-like particles derived from an orally transmissible virus stimulate mucosal and systemic immune responses by oral administration. Gene Therapy 2004; 11:628-635). According to the present invention, a reducing agent or a chelating agent or both are used to disassemble the VLPs. Various reducing agents can be used. Preferred embodiments of the reducing agents include, but are not limited to, dithiothreitol (DTT). Various chelating agents can be used, e.g., ethylene glycol tetraacetic acid (EGTA) or ethylenediaminetetraacetic acid (EDTA). Examples of VLP disassembly conditions include, but are not limited to, the following: purified VLPs were disrupted by incubation of a buffer containing 50 mM Tris-HCl (pH 7.5), 150 mM NaCl, 1 mM EGTA and 20 mM dithiothreitol for 30 minutes.

A skilled artisan would also recognize that complete disassembly of the VLPs is not required, although preferred, to encapsulate a heterologous nucleic acid. An artisan would also recognize that, on other occasions, it is preferred to have partial disassembly of the VLPs. According to the present invention, the conditions for the partial disassembly of the VLPs can be controlled to still allow efficient encapsulation of a heterologous nucleic acid. Partial disassembly of the VLPs can be achieved by treatment of VLPs with reducing agents alone (e.g., 20 mM DTT) (Sapp et al, J. Gen. Virol., 76:2407-2412, 1995.). According to the present invention, once the VLPs are disassembled completely or partially, encapsulation of a heterologous nucleic acid can be carried out by reassembling the VLPs in the presence of a heterologous nucleic acid.

In some embodiments of the present invention, reassembly of the VLPs is achieved by re-supplementation of calcium ions to the disrupted VLPs. Alternatively, reassembly of the VLPs is achieved by removal of the reducing agents or the chelating agents. Optionally, factors such as pH and ionic strength, other factors described in the present invention, can be adjusted to achieve efficient reassembly of the VLPs and efficient encapsulation of the heterologous nucleic acid. Examples of VLP disassembly conditions include, but are not limited to, the following:

Following 30 min of incubation at room temperature, a heterologous nucleic acid in 50 mM Tris-HCl buffer (pH 7.5) and 150 mM NaCl was added to the disrupted VLP preparation. The disrupted VLP preparation was then refolded by incubation for 1 h with increasing concentrations of $CaCl_2$ up to a final concentration of 5 mM. VLPs were pelleted by ultracentrifugation and resuspended in 10 mM potassium-MES buffer (pH 6.2). At each step, the VLP structure formation was confirmed by electron microscopy after negative staining, as described previously. To estimate the amounts of encapsulated plasmid DNA, refolded and purified VLPs were treated with 10 IU benzonase (SIGMA-ALDRICH, Irvin, UK) for 1 h at 20° C. to remove DNA on the surfaces of VLPs and disrupted with EGTA (1 mM). Absorbance of the supernatant was measured for detection of plasmid DNA contents.

One aspect of the invention relates to encapsulation of a heterologous nucleic acid with a modified HEV capsid protein, wherein the heterologous nucleic acid comprises an DNA expression cassette encoding an antigen of non-HEV source. According to the present invention, the DNA expression cassette may comprise a promoter sequence and a terminator sequence.

One advantage of the compositions and methods of the present invention is that the VLPs of the present invention can carries both peptide antigens and nucleic acid antigens. The peptide antigen is presented to the immune system in associated with MHC class II molecule. The encapsulated nucleic acids will be presented in the context of MHC class I systems.

In some embodiments of the invention, the heterologous peptide of the present invention (peptide antigen) and the heterologous nucleic acids of the present invention (nucleic acid antigen) are from the different sources. In some embodiments of the invention, the heterologous peptide of the present invention (peptide antigen) and the heterologous nucleic acids of the present invention (nucleic acid antigen) present different antigenic epitopes. In particularly preferred embodiments, the heterologous peptide of the present invention (peptide antigen) and the heterologous nucleic acids of the present invention (nucleic acid antigen) are from the same source, e.g., from the same virus. In most preferred embodiments, the heterologous peptide of the present invention (peptide antigen) and the heterologous nucleic acids of the present invention (nucleic acid antigen) present the same antigenic epitope or epitopes from a single pathogen. This provides synergistic effects in stimulating immune response against the same pathogen, therefore providing enhanced protection against a disease caused by the pathogen.

The size and number of the heterologous nucleic acids are controllable. According to the present invention, depending on the numbers of desired nucleic acids antigens to be presented, the amount and types of the heterologous nucleic acids can vary. In some embodiments of the invention, it is desired to present one epitope using the encapsulated nucleic acid, a number of copies of the heterologous nucleic acids can be allowed to be encapsulated within the VLPs. In other embodiments of the invention, it is desired to present 2 or more epitopes using the encapsulated nucleic acids, fewer copies of the heterologous nucleic acids would then be encapsulated within the VLPs.

The size of the VLPs can vary when different constructs of the modified hepatitis E virus capsid protein are used. For example, the N-terminal portion of the modified hepatitis E virus capsid protein can be adjusted to increase or decrease the size and encapsulation capacity of the VLPs. In some embodiments of the invention, in constructing the modified hepatitis E virus, a portion of HEV ORF 3 protein fused to the N-terminal of a portion of HEV ORF 2 proteins to adjust the size of the VLPs.

IX. Pharmaceutical Compositions, Formulations And Administration

The present invention also provides pharmaceutical compositions or physiological compositions comprising a heterologous nucleic acid encapsulated in a chimeric VLP formed by the modified HEV capsid protein of the present invention. Such pharmaceutical or physiological compositions also include one or more pharmaceutically or physiologically acceptable excipients or carriers. Pharmaceutical compositions of the invention are suitable for use in a variety of drug delivery systems. Suitable formulations for use in the present invention are found in *Remington's Pharmaceutical Sciences*, Mack Publishing Company, Philadelphia, Pa., 17th ed. (1985). For a brief review of methods for drug delivery. See Langer, *Science* 249: 1527-1533 (1990).

The compositions of the present invention can be administered to a host with an excipient. Excipients useful for the present invention include, but are not limited to, vehicles, binders, disintegrants, fillers (diluents), lubricants, glidants (flow enhancers), compression aids, colors, sweeteners, preservatives, suspending/dispersing agents, film formers/coatings, flavors and printing inks Various adjuvants can be used to increase the immunological response, depending on the host species, and include but are not limited to, Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette Guerin) and Corynebacterium parvum. Such adjuvants are also well known in the art. Further adjuvants that can be administered with the compositions of the invention include, but are not limited to, Monophosphoryl lipid immunomodulator, AdjuVax 100a, QS 21, QS18, CRL1005, Aluminum salts, MF 59, and Virosomal adjuvant technology. The adjuvants can also comprise a mixture of these substances.

One advantage of the compositions and methods of the present invention is that the compositions of the present invention can be administered to stimulate immune response without an adjuvant. Therefore, the compositions of the present invention are in some cases administered to a host without an adjuvant.

Another advantage of the present invention is that the compositions of the present invention are suitable for oral delivery. Because mucosal surfaces are inter-connected, stimulation of one mucosal surface by an antigen can induce mucosal immunity not only on the directly stimulated surface, but also on the distant ones. For example, oral delivery of the compositions of the present invention can protect against respiratory and genital-urinary infections. The compositions of the present invention are also suitable for mucosal delivery, such as delivery to the buccal or labial mucosa or the respiratory tract mucosa, including the nasal mucosa.

The pharmaceutical compositions of the present invention can be administered by various routes, e.g., oral, subcutaneous, transdermal, intramuscular, intravenous, or intraperitoneal. The preferred routes of administering the pharmaceutical compositions are oral delivery at daily doses of about 0.01-5000 mg, preferably 5-500 mg. The appropriate dose may be administered in a single daily dose or as divided doses presented at appropriate intervals, for example as two, three, four, or more subdoses per day.

For preparing pharmaceutical compositions of the present invention, inert and pharmaceutically acceptable carriers are used. The pharmaceutical carrier can be either solid or liquid. Solid form preparations include, for example, powders, tablets, dispersible granules, capsules, cachets, and suppositories. A solid carrier can be one or more substances that can also act as diluents, flavoring agents, solubilizers, lubricants, suspending agents, binders, or tablet disintegrating agents; it can also be an encapsulating material.

In powders, the carrier is generally a finely divided solid that is in a mixture with the finely divided active component, e.g., a chimeric virus-like particles with an encapsulated nucleic acid. In tablets, the active ingredient (a chimeric virus-like particles with an encapsulated nucleic acid) is mixed with the carrier having the necessary binding properties in suitable proportions and compacted in the shape and size desired.

For preparing pharmaceutical compositions in the form of suppositories, a low-melting wax such as a mixture of fatty acid glycerides and cocoa butter is first melted and the active ingredient is dispersed therein by, for example, stirring. The molten homogeneous mixture is then poured into convenient-sized molds and allowed to cool and solidify.

Powders and tablets preferably contain between about 5% to about 70% by weight of the active ingredient. Suitable carriers include, for example, magnesium carbonate, magnesium stearate, talc, lactose, sugar, pectin, dextrin, starch, tragacanth, methyl cellulose, sodium carboxymethyl cellulose, a low-melting wax, cocoa butter, and the like.

The pharmaceutical compositions can include the formulation of the active compound with encapsulating material as a carrier providing a capsule in which the active component (with or without other carriers) is surrounded by the carrier, such that the carrier is thus in association with the compound. In a similar manner, cachets can also be included. Tablets, powders, cachets, and capsules can be used as solid dosage forms suitable for oral administration.

Liquid pharmaceutical compositions include, for example, solutions suitable for oral or parenteral administration, suspensions, and emulsions suitable for oral administration. Sterile water solutions of the active component (e.g., a chimeric virus-like particles with an encapsulated nucleic acid) or sterile solutions of the active component in solvents comprising water, buffered water, saline, PBS, ethanol, or propylene glycol are examples of liquid compositions suitable for parenteral administration. The compositions may contain pharmaceutically acceptable auxiliary substances as required to approximate physiological conditions, such as pH adjusting and buffering agents, tonicity adjusting agents, wetting agents, detergents, and the like.

Sterile solutions can be prepared by suspending the active component (e.g., a chimeric virus-like particles with an encapsulated nucleic acid) in the desired solvent system, and then passing the resulting solution through a membrane filter to sterilize it or, alternatively, by dissolving the sterile compound in a previously sterilized solvent under sterile conditions. The resulting aqueous solutions may be packaged for use as is, or lyophilized, the lyophilized preparation being combined with a sterile aqueous carrier prior to administration. The pH of the preparations typically will be between 3 and 9, more preferably from 5 to 8, and most preferably from 6 to 7.

The pharmaceutical compositions of the present invention can be administered for prophylactic and/or therapeutic treatments. In therapeutic applications, compositions are administered to a patient already suffering from a condition in an amount sufficient to prevent, cure, reverse, or at least partially slow or arrest the symptoms of the condition and its complications. An amount adequate to accomplish this is defined as a "therapeutically effective dose." Amounts effective for this use will depend on the severity of the disease or condition and the weight and general state of the patient, but generally range from about 0.1 mg to about 2,000 mg of the composition per day for a 70 kg patient, with dosages of from about 5 mg to about 500 mg of the composition per day for a 70 kg patient being more commonly used.

In prophylactic applications, pharmaceutical compositions of the present invention are administered to a patient susceptible to or otherwise at risk of developing a disease or condition, in an amount sufficient to delay or prevent the onset of the symptoms. Such an amount is defined to be a "prophylactically effective dose." In this use, the precise amounts of the composition again depend on the patient's state of health and weight, but generally range from about 0.1 mg to about 2,000 mg of the inhibitor for a 70 kg patient per day, more commonly from about 5 mg to about 500 mg for a 70 kg patient per day.

Single or multiple administrations of the compositions can be carried out with dose levels and pattern being selected by the treating physician. In any event, the pharmaceutical formulations should provide a quantity of composition of the present invention sufficient to effectively stimulate immune response in the patient, either therapeutically or prophylatically.

XI. EXAMPLES

The following examples are provided by way of illustration only and not by way of limitation. Those of skill in the art will readily recognize a variety of non-critical parameters that could be changed or modified to yield essentially the same or similar results.

Examlpe 1

The Capsid Structures of Hepatitis E Virus (HEV)

Hepatitis E accounts for the majority of enterically transmitted non-A, non-B hepatitis worldwide. In countries with poor sanitary conditions and high population density, hepatitis E causes water-borne epidemics with substantial mortality rates (20%) in pregnant women (Zhou et al., 2005. Vaccine 23:3157-65.). The causative agent is the hepatitis E virus (HEV), a non-enveloped single-stranded positive-sense RNA virus, belonging to the Hepevirus genus in the Hepeviridae family (Emerson et al., 2004. Hepevirus. Elsevier/Academic Press, London.).

The HEV virion has a diameter about 32 to 34 nm and encapsidates a 7.2 kb genome. The full-length genome contains three open reading frames (ORFs), one of which, ORF2, maps to the 3' terminus and encodes the 660 amino acids viral capsid protein. Like other hepatitis viruses, HEV is unable to propagate in large quantities in current cell culture systems. Preventive strategies rely on recombinant protein vaccines derived from the HEV capsid protein (Maloney et al., 2005. Vaccine 23:1870-4.).

Self assembled virus-like particles (VLPs) from the HEV structural protein were observed when a construct of the ORF2 protein lacking the RNA-binding N-terminal 111 amino acids was expressed in the Tn5 insect cell line. These particles, measuring 27 nm in diameter, were much smaller than the native virion; but nevertheless, they were recognized by anti-HEV sera and could induce protective immunity in Cynomolgus macaques (Li et al., 2004. Vaccine 22:370-7.). Therefore, essential epitopes are well-preserved and remain exposed on the surface of these small particles, making them a potential viable vaccine (Li et al., 2001. Vaccine 19:3476-84; Maloney et al., 2005. Vaccine 23:1870-4.). Analysis showed that the recombinant HEV VLPs were assembled of the ORF2 protein truncated at the C-terminus by a Tn5 cell furin-like activity (Li et al., 2005. J Virol 79:12999-3006; Li et al., 1997. J Virol 71:7207-13.). Expression of the HEV ORF2 protein in other cells demonstrated that removal of the C-terminal 52 amino acid (aa) residues is a prerequisite to VLP formation. With this knowledge, several self-assembling recombinant HEV VLPs have been constructed, demonstrating that the residues 126 to 601 are the essential elements for the initiation of VLP assembly (Li et al., 2005. J Virol 79:12999-3006.).

Three-dimensional structures of the recombinant VLP expressed in Tn5 (VLPTn5) and Sf9 (VLPSf9) cells have been determined by electron cryomicroscopy (cryo-EM) at the resolutions of 22 and 23 Å, respectively. Structural studies revealed that the recombinant HEV VLP is an empty T=1 icosahedral particle containing 30 spike-like protrusions extending from the capsid surface (Li et al., 2005. J Virol 79:12999-3006; Xing et al., 1999. Virology 265:35-45.). Density analysis revealed that the truncated ORF2 protein contains two distinct domains; namely, a shell (S) domain, which forms the continuous surface of the viral capsid, and a protrusion (P) domain, which forms the protruding spikes. Neighboring protein subunits at each icosahedral 2-fold axis combine to form the 30 protrusions. The internal cavity of the recombinant HEV VLP has a diameter of 9.3 nm, which is insufficient to encapsidate a full length RNA genome; hence, there is no significant RNA density found within the particle in the three-dimensional reconstruction (Xing et al., 1999. Virology 265:35-45.).

Similar studies using the recombinant truncated ORF2 protein (aa residues 112-607) from Sar55 strain expressed in Sf9 cells failed to detect VLP formation. The monoclonal antibodies (MAbs) raised against the truncated ORF2 or isolated by phage display from a chimpanzee cDNA library neutralized the HEV SAR-55 strain in vivo (Schofield et al., 2000. J Virol 74:5548-55.). These antibodies were mapped to recognize the epitope located at residues 578-607 by radio-immunoprecipitation assays. A further characterization of the antigenic sites of the truncated ORF2 protein (aa residues 112-607) of the Sar55 strain showed that the antigenic site located at the C-terminal region overlaps with the epitope recognized by neutralizing antibodies, and the C-terminus is important for enhancing the presentation of this epitope (Schofield et al., 2003. Vaccine 22:257-67.).

The location of the HEV ORF2 C-terminus has not yet been experimentally identified. Sequence analysis indicates, however, that this site is solvent accessible. The HEV ORF2 aggregation into VLP is a key factor for assembly of the conformation-dependent epitopes in a functional form (Maloney et al., 2005. Vaccine 23:1870-4.). Taking into consideration that the HEV neutralizing antigenic epitope is conformation-dependent and located in the C-terminal region ORF2 proteins (Meng et al., 2001. Virology 288:203-11; Schofield et al., 2003. Vaccine 22:257-67.), we have conducted a structural analysis of the C-terminal region in the context of HEV VLP assembled of the truncated ORF2 protein using cryo-EM and three-dimensional reconstruction techniques. In the course of the study we determined the structure of a chimeric recombinant VLP containing a B-cell tag of 11 amino acids inserted after residue 608 (Niikura et al., 2002. Virology 293:273-80.) and a recombinant VLP associated with Fab fragments from the mouse monoclonal antibody against residues 595-601. Additionally, three-dimensional structure was predicted for the C-terminal region at position 525 to 608, which is partially included in the HEV neutralizing epitope (Meng et al., 2001. Virology 288:203-11.). It is important to note that the results from three-dimensional structure prediction concur with those from cryo-EM, revealing that the binding footprint at the C-terminal region covers the lateral side of the P domain, including the neutralizing epitope of ORF2 protein, and terminates at the spike surface.

Materials and Methods

Production and purification of IgGs: Eight-week-old female BALB/c mice were immunized at 0 and 4 weeks by intraperitoneal inoculation with HEV VLPs (100 ug/ml). Four weeks later, a final boost of equal volume of antigen was administered. Three days after the final boost, mouse spleen cells were fused with P3U1 mouse myeloma cells using polyethylene glycol 1500 (50% [wt/vol]) (Boehringer, Mannheim, Germany) as essentially described by Adler and Faine (Adler et al., 1983. Pathology 15:247-50). Supernatant from microplate wells positive for hybridoma growth was screened by enzyme-linked immunosorbent assay (ELISA) using the recombinant HEV VLPs as antigen. Hybridomas secreting specific antibodies to HEV were subcloned three times by limiting dilution, after which they were considered to be monoclonal. Antibodies in the supernatants were isotyped using the Mouse Monoclonal Antibody Isotyping kit (Amersham, Little Chalfont, Buckinghamshire, U.K.) in accordance with the manufacturer's protocol. Hybridomas were grown in bulk in stationary flasks (Nunc, Roskilde, Denmark) using PRMI-1640 with 15% FCS. Supernatant was harvested and antibodies were purified using HiTrap protein G affinity columns (Pharmacia Biotech AB, Uppsala, Sweden) and stored at −80 C. The mouse monoclonal antibody MAb 224 has immunoglobulin G1 (IgG1) isotype.

Preparation of Fab fragments: A method employing papain cleavage was used to yield the isolated Fab fragments from purified MAb224. A reducing L-cystein buffer was used to activate papain, and the MAb224 was mixed with papain in a 100:1 molar ratio. The cleavage mixture was incubated overnight at 30 ° C. The reaction was quenched by adding iodacetamide and analyzed on SDS-PAGE. The papain digestion product was purified using a Protein-A column according to the manufacturer's instruction. The Fc fragments and uncleaved MAbs224 were immobilized on the column in binding buffer while the Fab fragments were collected in the flow-through fractions.

Purification of the VLPs: The construct of recombinant baculoviruses was prepared as described (Li et al., 2005. J Virol 79:12999-3006; Li et al., 1997. J Virol 71:7207-13; Niikura et al., 2002. Virology 293:273-80.); as VLP/C-tag, B-cell tag epitope on glycoprotein D of herpes simplex virus "QPELAPEDPED" (SEQ ID NO:7) was inserted after amino acid 608. The production and purification of HEV VLPs were conducted as described (Li et al., 2005. J Virol 79:12999-3006; Li et al., 1997. J Virol 71:7207-13; Niikura et al., 2002. Virology 293:273-80; Xing et al., 1999. Virology 265:35-45.). Briefly, the DNA fragments containing the N-truncated ORF2 protein (for VLPTn5), N-and-C-truncated ORF2 protein (for VLPSf9) and N-truncated-and-C-inserted ORF2 protein (contains VLP/C-tag) were cloned with baculovirus transfer vector pVL1393 to yield pVLORF2. Insect Sf9 cells (Riken Cell Bank, Tsukuba, Japan) were co-transfected with pVLORF2 and the linearized wild-type *Autographa californica* nuclear polyhedrosis virus DNA (Pharmingen BaculoGold™ #21100D) by the lipofectin-mediated method to produce recombinant baculoviruses. The recombinant baculovirus was plaque-purified three times. Both Sf9 and Tn5 cells, the latter from a Trichoplusia ni, BTL-Tn 5B1-4 (Tn5) (Invitrogen, San Diego, Calif.) (Wickham et al., 1993) were infected with the recombinant baculoviruses at a m.o.i.>5 and incubated in EX-CELL™ 405 medium (JRH Biosciences, Lenexa, Kans.) for 6 days at 26.5° C. The supernatant was collected and intact cells, cell debris and progeny baculoviruses were removed by centrifugation at 10,000g for 90 min. The supernatant was then spun at 30,000 rpm for 2 h in a Beckman SW32 Ti rotor. The resulting pellet was resuspended in 4.5 ml EX-CELL™ 405 and stored at 4° C. After mixing with 1.96 g of CsCl, the sample was centrifuged at 35,000 rpm for 24 h at 4° C. in a Beckman SW55Ti rotor. The white band was harvested by puncturing the tubes with a 22-gauge needle, diluted 4 times with EX-CELL™ 405 and centrifuged for 2 h in a Beckman TLA 55 rotor at 45,000 rpm to remove CsCl. The VLPs were re-suspended in 100-500 µl of EX-CELL™ 405 and stored at 4° C. The material was later diluted with 10 mM potassium-MES buffer.

Preparation of VLP-Fab complexes for cryo-electron microscopy: The VLP/Fab224 complexes were prepared by incubating Fab224 fragments with VLP purified from Sf9 cells (VLPsf9) at a molar ratio exceeding 1:300 in 10 mM pH 6.2 potassium-MES buffer at 4° C. over night. High purity VLP/Fab224 complexes were obtained using a short column containing Sephacryl-300 to remove the unbound Fab fragments from the sample in order to reduce the background densities for the subsequent structural determination. The fractions containing VLP/Fab224 complexes were collected based on reading UV spectro-photometer at an optical density (OD) of 280 nm. The Fab binding occupancy was roughly estimated by SDS-PAGE, in which the purified VLP/Fab224 complexes were loaded on an acrylamide gel (gradient 8-25%) and electrophoresis was run on a Phast™ system (Pharmacia) under constant-voltage condition. The integrity of particles was checked by negative stained electron microscopy (EM) using 2% uranyl acetate (UA).

Cryo-electron microscopy: The sample preparation and cryo-EM operation were followed well established procedures described previously (Li et al., 2005. J Virol 79:12999-3006; Xing et al., 1999. Virology 265:35-45.). Briefly, a drop containing 3.5 μl of sample was applied on a glow-discharged homemade holey-carbon grid, blotted with a piece of filter paper for 3 s to remove the extra liquid and quickly plunged into liquid ethane cooled by liquid nitrogen in a homemade cryo-container. Samples were frozen in a thin layer of vitrified ice. The grid was then transferred into a Gatan 626DH (Gatan Inc, CA) cryo-holder and kept at the low temperature environment (−178 °C.) for the subsequent processing. Micrographs were recorded under low-dose condition (<10 e-/Å2) using Kodak 50163 films at a magnification of 45,000× on an Philips CM-120 electron microscopy operated at 120 kV and photographed at the defocus range from 1000 to 3000 nm. Micrographs were visually inspected and selected based on the criteria of suitable particle concentration, optimal ice thickness and minimal specimen drift. Only those micrographs fulfilling these criteria were analyzed.

Figure 2:
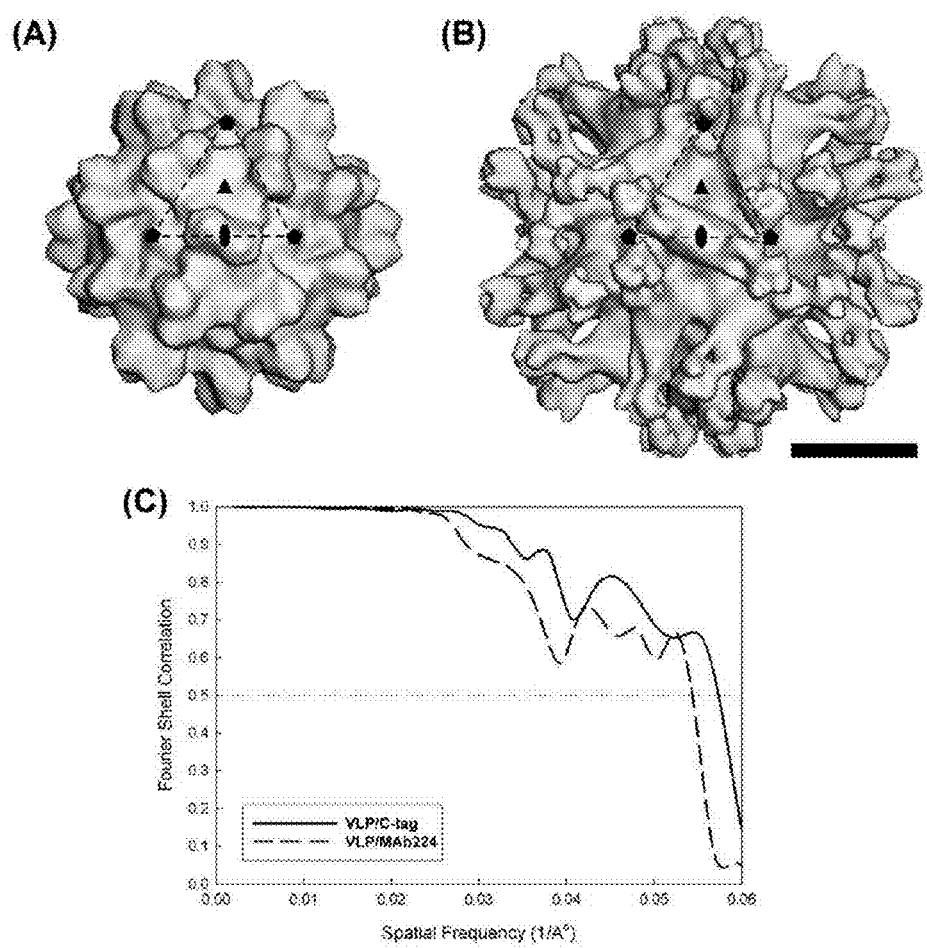
FIG. 2 Surface representation of the HEV structures. (A) VLP/C-tag and (B) VLP/MAb224 viewed along the icosahedral two-fold axis. The positions of the two-, three-, and five-fold axis are marked as oval, triangle, and pentagon, respectively. The density level was used to account for 100% of the expected protein volume. In both reconstruction the capsid protein, truncated ORF2 protein, establishes an arrangement according to a T=1 surface lattice with 30 protruding spikes at each two-fold positions. In (B), the MAb224 appeared as two domains configuration, where the variable domain was bound to the side-shoulder of the P domain of VLP, and the constant domain was slightly tilted perpendicular to the surface of the particle. The scale bar is 100 Å. (C) Resolution estimated by FSC. The particles of each map were evenly divided into two sub-datasets and reconstructed. The correlation was used as a function of spatial frequency (1/resolution, Å) between two independent reconstructions. The resolution of VLP/C-tag (dashed line) was calculated to 17.5 Å and the resolution of VLP/MAb224 was calculated to 18.5 Å (solid line).

Image processing: Selected micrographs were digitized using a Heidelberg Primescan D8200 (Heidelberg, Germany) at a 14 μm scanning step size, corresponding to 3.11 Å per pixel at specimen space. Particles were manually picked using Robem (v2.14), and centered by cross-correlating each of them against the circular average image. The astigmatism and the defocus value were evaluated by the average sum of the power spectra from all particles within single micrograph. The first zero of the data used for the following structural determination was approximately within the range of 17-20. The self-common line algorithmic was used to yield the initial models for VLP/C-tag and VLP/MAb224 (Crowther, 1971. Philos Trans R Soc Lond B Biol Sci 261:221-30.), respectively. The following origins and orientations search of each particle was carried out iteratively using polar Fourier transformation (PFT) algorithm (pftsearch program) running on an AMD MP1800 MHz dual-processors Linux workstation (Baker & Cheng. 1996. J Struct Biol 116:120-30.). Three-dimensional reconstructions were computed by combining a set of particles of orientations spreading evenly in an icosahedral asymmetric unit, with the Fourier-Bessel algorithm and superimposing of 5-3-2 icosahedral symmetry (em3dr program). To examine the reliability of the three-dimensional reconstruction, at the final refinement step, the dataset was evenly divided into two parts and computed two three-dimensional reconstructions, respectively. The resolution was estimated using Fourier shell correlation (FSC) by assessing the agreement between these two reconstructions in the Fourier space; a coefficient value of 0.5 was used as the criteria, the estimated resolutions of the three-dimensional reconstructions of VLP/C-tag and VLP/Fab224 were computed to 17.5 Å and 18.5 Å, respectively (FIG. 2C).

The three-dimensional reconstructions were rendered and visualized using Robem and PyMOL (DeLano, 2002. The PyMOL Molecular Graphics System. DeLano Scientific, Palo Alto, Calif., USA.). The contour level was chosen at the value corresponding to the 100% mass of the particle volume. The electron density map was inspected in the isosurface mode, which builds a surface barrier to contour the density about a certain threshold, provided the concise surface details on the density map.

Difference maps analysis: Difference maps were computed by first searching the magnification factor between two three-dimensional models and adjusted them to have the minimum difference using cmpEM. As the searching results showed all the models having the size difference less than 0.5%, the magnification factor was set to 1. Then, all the densities corresponding to the S domain were radially scaled by multiplied a fixed factor and added a constant using cmpEM. The difference maps were obtained by subtracting VLPTn5 from VLP/C-tag and VLPSf9 from VLP/Fab224. The models of VLPTn5 and VLPSf9 were taken from previously study (Li et al., 2005. J Virol 79:12999-3006.). The resulting difference maps were set the solvent density to zero at the radii smaller than inner surface of S domain and the radii beyond the largest radii of VLP/C-tag and VLP/Fab224. The contour level were chosen to match the mass of tag using an average protein density of 1.36 g/cm3 and the estimated molecule weight of Fab224 was used 45 kDa.

Structural prediction on partial truncated HEV ORF2 protein: The structure prediction was carried out by two steps methods; namely (A) Domain parsing and (B) De novo three-dimensional structure prediction.

(A) Domain parsing: to predict the three-dimensional model of the C-terminal region of the truncated ORF2 protein (residues 112-608), a domain prediction method Ginzu (Kim et al., 2005. Proteins 61 Suppl 7:193-200.) was used as the first step for structure prediction. Ginzu is a sequential procedure for detection of putative domains. It first performs homologous structure searches to detect regions in a query sequence that are homologous to experimentally determined three-dimensional structures. BLAST, PSIBLAST (Altschul et al., 1997. Nucleic Acids Res 25:3389-402.), FFAS03 (Jaroszewski et al., 2002. Protein Sci 11:1702-13; Rychlewski et al., 2000. Protein Sci 9:232-41.), and 3D-Jury (Ginalski et al., 2003. Bioinformatics 19:1015-8; Ginalski & Rychlewski, 2003. Nucleic Acids Res 31:3291-2.) are used for this step. In the case of regions without homologous structures, Ginzu continues with a search against Pfam-A using HMMER (Cheng et al., 1994. Structure 2:271-82.) and then parsing by multiple sequence alignment (MSA) based methods to predict putative domains. Since the truncated ORF2 protein sequence did not match any homologous structure, selecting cut points between the domains was done using an MSA of the full-length ORF2 protein target derived from PSI-BLAST search against NCBI non-redundant (NR) protein sequence database. The most populated non-overlapping clusters of sequences in the MSA were assigned as domains, and the final cut points were made at positions that have high incidence of sequence termini, a strong loop prediction (as determined by PSIPRED (Jones, 1999. J Mol Biol 292:195-202.)), and reduced occupancy of aligned residues. Boundaries were assigned so that the putative domains remained within size limits (~200 residues) approachable to the de novo three-dimensional structure prediction protocol of the Rosetta software package (Bonneau et al., 2001. Proteins 43:1-11; Bonneau et al., 2001. Proteins Suppl 5:119-26.). Hence, the truncated ORF2 protein was broken up into putative five domains and the domain corresponding to the C-terminal region contains 84 amino acids (residues 525-608).

(B) De novo three-dimensional structure prediction: the three-dimensional structure of this domain was modeled using the Rosetta de novo protocol, as implemented in the Rosetta server (Kim et al., 2004. Nucleic Acids Res 32:W526-31.). For each putative domain, three- to nine-residue fragment libraries representing local conformations present in the protein database (PDB) were generated and then assembled into models by fragment insertion using a scoring function that favors protein-like features (Simons et al., 1997. J Mol Biol 268:209-25; Simons et al., 1999. Proteins 34:82-95.). Ten thousand decoys for the original C-terminal region of the truncated HEV ORF2 query protein and 5000 decoys for up to two sequence homologs were generated. From this set of decoys, 2000 query decoys and 1000 decoys from the sequence homologs were selected based on score and filtering out decoys with unfavorable number of local contacts or strand topologies. The selected decoys were then clustered based on Cα root-mean-square deviation (RMSD) over all ungapped positions. The top 9 cluster centers were chosen as the best ranked models, and the best scoring model that passed all of the above mentioned filters was selected as the 10th model. The models having the best 10 ranking scores were then used for fitting into cryo-EM density maps.

Fitting the X-ray Atomic model of the truncated ORF2 protein into cryo-EM density maps of chimeric HEV VLP and VLP/Fab224: Manually fitting was carried out by translational and rotational movement of the predicted three-dimensional atomic models into the cryo-EM density maps using program O (Jones et al., 1991. Acta Crystallogr A 47 (Pt 2):110-9.). The contour level of cryo-EM density maps was chosen to ensure the volume rendered at 100% mass assuming a protein density of 1.36 g/cm3. To achieve the best fit of the models in cryo-EM density maps, the entire atomic model was treated as a rigid body; the fitting procedure used the criteria that the residues 595-601 need to be exposed at the surface as well as located closed to the density of MAb224-Fab; in the meantime, the C-terminus of the predicted model should also point toward to the surface of the particle. To optimize the fitting results, symmetry-related molecules were generated and judged by the crashes between each molecule. Only one out of the best ten models was found to meet the fitting criteria by visual inspection. The figures were prepared using the program PyMOL (DeLano, 2002. The PyMOL Molecular Graphics System. DeLano Scientific, Palo Alto, Calif., USA.).

Results

MAb224 recognizes residues 595-601 of the HEV ORF2 protein: A Western blotting assay was performed to characterize the epitope recognized by antibody MAb224. A series of C-terminally truncated ORF2 proteins were separated using 10% SDS-PAGE, and blotted with MAb224 (FIG. 1A). Truncated ORF2 proteins comprising residues 112-600, 112-596, and 112-589 were unable to interact with MAb224. These data indicate that residue 601 is the most important for MAb224 binding. Taking into consideration that antigenic epitopes are usually short regions of 3-7 aa long, Mab224 binding site should locate within aa position 595-601 of the ORF2 protein and it is within the neutralization epitope localized at residues 578-607 reported by Schofield et al (Schofield et al., 2000. J Virol 74:5548-55.). The lower molecular weight protein detected with MAb224 are products of degraded ORF2 protein at the N-termini.

The C-terminal markers: We used two markers for the identification of position of the C-terminal region in three-dimensional structure as shown in FIG. 1B. First, a chimeric recombinant HEV VLP containing the 11 aa B-cell tag epitope inserted at aa 608 (VLP/C-tag) was used to map this epitope in VLP. Results from both immunoprecipitation and enzyme-linked immunosorbent assay (ELISA) experiments suggest that the tag epitope is exposed on the particle surface (Niikura et al., 2002. Virology 293:273-80.). Second, MAb224 epitope mapped at 601-608 was used to detect this region in VLP particles. It was found that MAb224 reacted with the intact recombinant HEV VLP in an ELISA experiment, suggesting that the region at position 601-609 is exposed on the BLP surface. To increase the density of the MAb224 binding to VLP; we used Fab fragments instead of MAb224 in the IgG form. For this purpose, MAb224 was treated with papain and the Fab fragments were purified. The resulting Fab fragments were incubated with VLP overnight to obtain VLP-Fab complexes (VLP/MAb224) for the subsequent data collection.

Two-dimensional electron cryo-micrographs: Cryo-EM specimens of VLP/C-tag and VLP/MAb224 were prepared by standard procedures (Li et al., 2005. J Virol 79:12999-3006; Li et al., 1997. J Virol 71:7207-13.). The samples were imaged at a magnification of 45,000× in a Philips CM-120 EM operated at 120 kV. Digitized cryo-electron micrographs of frozen-hydrated samples embedded in the thin layer of vitreous ice shown that both particles had circular profiles with spiky densities extending from the surface (FIG. 1C). Both particles appeared as empty cores, suggesting the absence of RNA moiety, which is completely consistent with our previous observation (Li et al., 2005. J Virol 79:12999-3006; Xing et al., 1999. Virology 265:35-45.). The sizes of both particles were approximately 27 nm without taking into account the extra densities extending further from the surface of VLP/MAb224 (FIG. 1C, right).

Three-dimensional reconstruction of VLP/C-tag and VLP/MAb224: A total of 782 particles were used to reconstruct the final three-dimensional model of VLP/C-tag and 615 particles for VLP/MAb224. Surface representations of cryo-EM structures of VLP/C-tag and VLP/MAb224 exhibited similar features as they both displayed T=1 icosahedral symmetry with 60-protein-subunits arranged into 30 dimeric protruding spikes located at each icosahedral two-fold axis. In agreement with the previously published cryo-EM structure of VLP (Li et al., 2005. J Virol 79:12999-3006.), the surfaces of VLP/C-tag and VLP/MAb224 can also be divided into two distinct domains, a surface (S) domain and a protrusion (P) domain. The S domain forms a continuous basal shell of the capsid with small hollows at each icosahedral five-fold axis. The P domain projects outward from the surface with adjacent protein subunits located at two-fold axis forming dimeric arch-like spike. The distance between each two-fold axis at the top surface of P domain was ~76 Å and that is also consistent with the results measured in VLPTn5 and VLPSf9 (Li et al., 2005. J Virol 79:12999-3006.). No significant RNA density was found within both structures.

In VLP/C-tag, the particle had a diameter of approximately 280 Å measured from three-dimensional reconstruction (FIG. 2A). The P domains showed two discernible prominences at the top, which were not observed in VLP/MAb224 (FIG. 2B) or other VLP structures published earlier (Li et al., 2005. J Virol 79:12999-3006.). The prominence has the height about 6 Å measured from the top of the P domain. In contrast to structure of VLP/C-tag, in VLP/MAb224 the diameter of the particle itself without Fab fragments was approximately 270 A; in addition, sixty Fab fragments were observed around the particle. MAb224 bound to the shoulder of the P domain tilting away from the parallel direction of the two-fold axis. The height of the Fab molecule was measured ~57 Å as by the long axis perpendicular to the surface of P domain, and along the top view of two-fold axis, the adjacent MAb224 has a distance of 95 Å. Both VLP/C-tag and VLP/MAb224 presented here were the density maps rendered at the contour of 100% mass-volume estimated by using an average protein density of 1.36 g/cm3. No steric hindrance was observed in the 3D reconstruction between each Fab molecule around the regions of either five-fold or three-fold axes.

Figure 3:
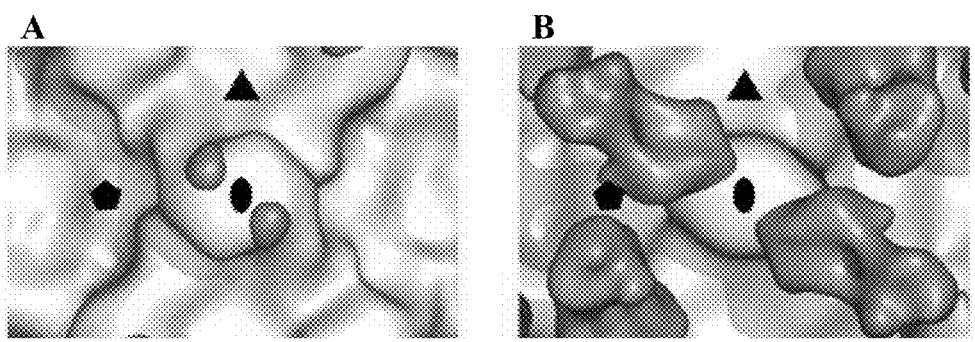
FIG. 3 The difference maps for the tag epitope and MAb224 at the two-fold axis. (A) Difference map calculated by subtracting VLP/C-tag from VLPTn5, and the resulting C-terminal inserted tag epitope was superimposed on the corresponding region of the reconstruction of VLPTn5, and the density level was chosen to account for 100% mass of expected tag volume using the average protein density of 1.36 g/cm3. (B) Difference map calculated by subtracting VLP/MAb224 from VLPSf9, and the resulting MAb224 fragments was superimposed on the corresponding region of the reconstruction of VLPSf9.

Determining the C-terminal tail on recombinant HEV VLP: Significant differences were noted on the top surface of P domain of VLP/C-tag compared to unmodified VLP. To analyze whether the difference was caused by the inserted tag, a complementary analysis was used to calculate the difference map by subtracting VLPTn5 from VLP/C-tag. The S domain radii were matched, which allowed for analyzing differences between the radii corresponding to the P domain since the tag was found to be exposed to the surface. Taking into consideration that the average protein density is 1.36 g/cm3, the tag volume was estimated to be 1.70 nm3, The resulting difference map superimposed on VLPTn5 revealed the density of the tag located at the top surface of the P domain where the prominences were found (FIG. 3A). Similar analysis was applied to VLP/MAb224; the difference map was calculated by subtracting VLPSf9 from VLP/MAb224 revealing the Fab density located at the lateral side of P domain (FIG. 3B). The footprint of MAb224 binding covered the residues of 601-608 of the C-terminal region according to the western blotting analysis.

Figure 4:
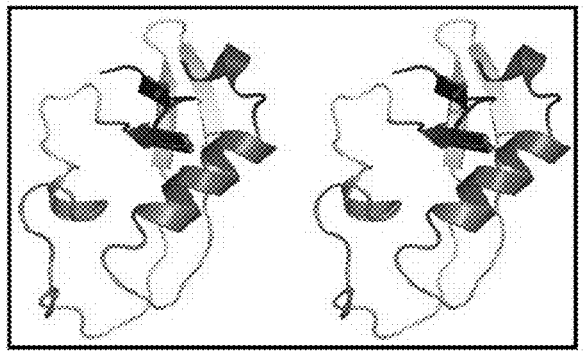
FIG. 4 Secondary and tertiary structure predictions of C-terminal peptide (SEQ ID NO:3). Alpha-helix was marked with the letter H and beta-sheet was marked with E. Stereo view of the tertiary structure was shown in the inset at the right bottom. The protein backbone was rendered in a 'cartoon' style to highlight the secondary structure.
Figure 5:
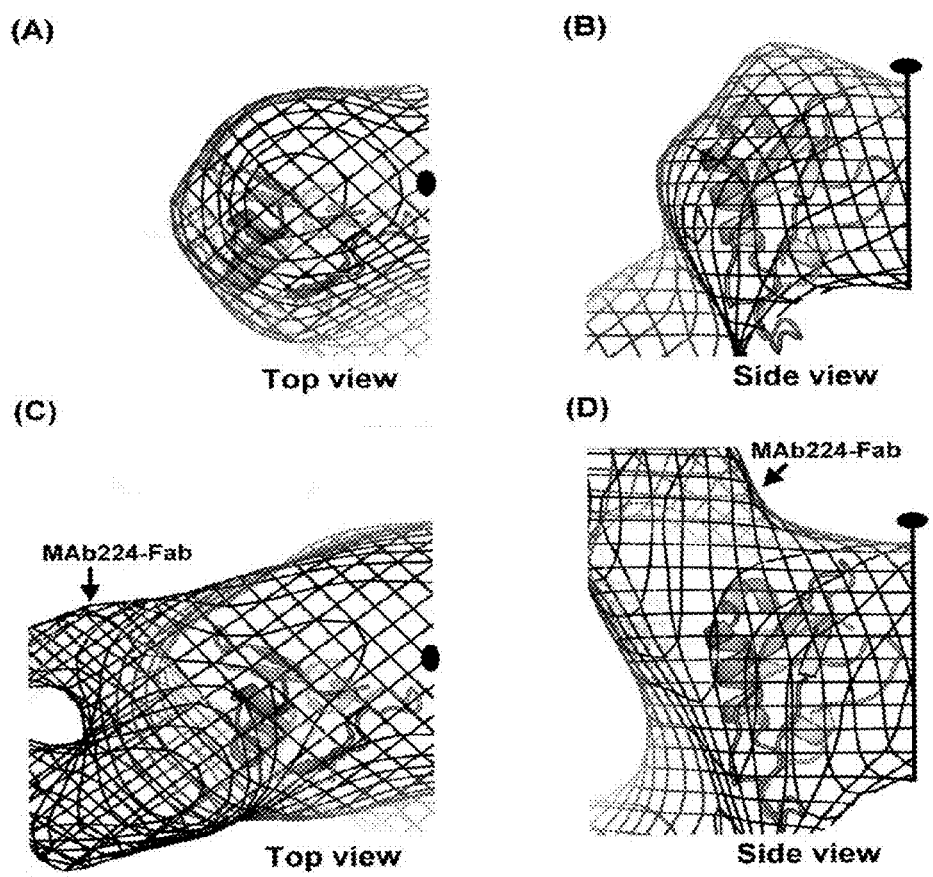
FIG. 5 Fitting of the predicted 3D atomic model into cryo-EM density maps. (A and C) top views and (B and D) side views of VLP/C-tag and VLP/MAb224. Cryo-EM density maps (as shown in mesh) were fitted with the predicted model shown in a cartoon representation. The predicted atomic model was manually fitted into the cryo-EM density according to the epitope region and C-terminus region of cryo-EM density maps. The epitope position was exposed to the surface and located at the side of the P domain.
Figure 6:
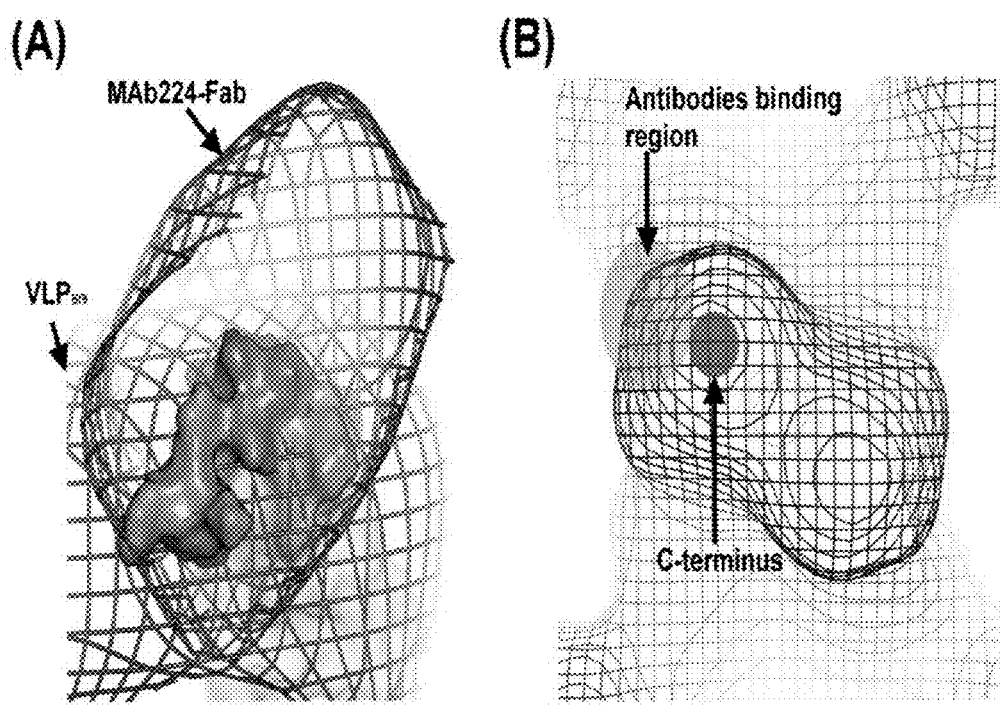
FIG. 6 Surface mapping of the epitope and C-terminus. (A) The predicted 3D model fitted in the difference map of MAb224 together with VLPSf9 viewed from the side of the P domain. The epitope region is shown in a surface representation. Note the binding site of the neutralizing antibody overlaps with the binding site of MAb224, and the footprint of MAb224 covers the whole epitope. (B) The C-terminal route started from the lateral sides of P domain, which was found interacting with antibodies recognized the antigenic site at the carboxyl terminus, and ended at the top surface of the P domain.
Figure 7:
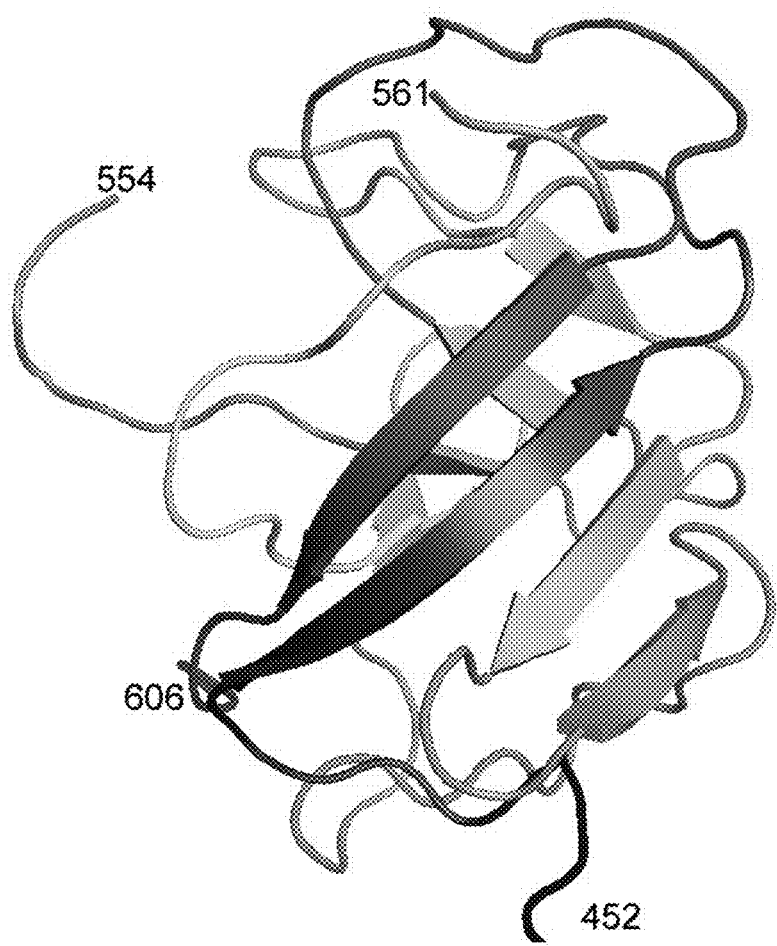
FIG. 7 The atomic structure of C-terminal P domain determined by X-ray crystallography. The structure was shown as 'cartoon' mode to highlight the secondary structure. The amino acids 555-560 are disordered in the capsid and are less resolved from the electron density map.
Figure 9:
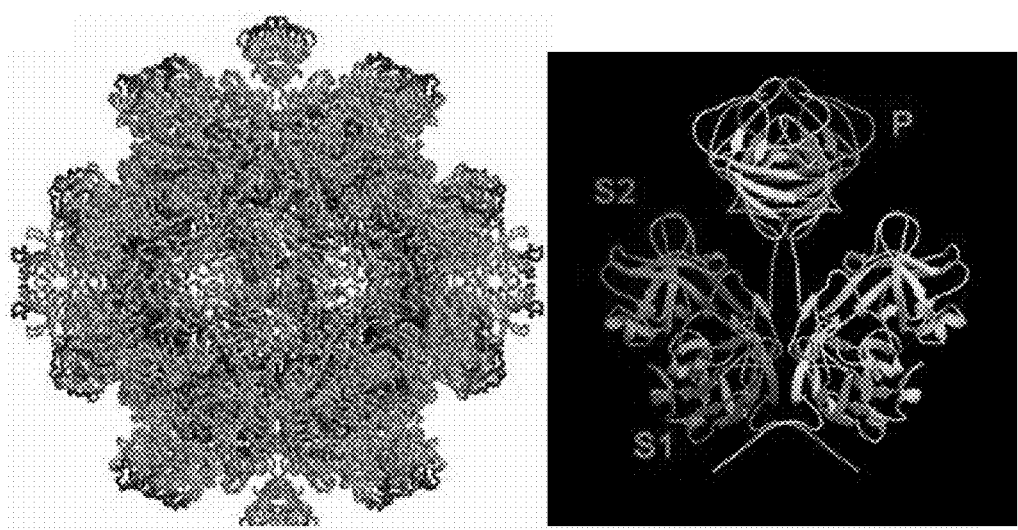
FIG. 9 Structure of HEV-VLP and capsid protein dimer of HEV-VLP.

Structural prediction for the C-terminal region: The structure of the C-terminal region at position 525-608 was modeled using Rosetta protocols (Kim et al., 2004. Nucleic Acids Res 32:W526-31.). The model with the top 10 scores were used and evaluated by manually fitting each of them into VLP/C-tag and VLP/MAb224 density maps using the software O (Jones et al., 1991. Acta Crystallogr A 47 (Pt 2):110-9.). As the tag epitope was shown to be exposed on the surface of VLP/C-tag (Niikura et al., 2002. Virology 293:273-80.), those models with tag buried either in the center of the P domain or under the S domain of VLP were discarded because the region 601-608 should be located close to the footprint of the MAb224 binding sites. Only one model met the criteria described above (FIG. 4). This model contains three alpha-helixes (residues 546-550, 591-601 and 604-607), and four beta-strands (residues 526-530, 535-540, 563-573, and 577-585). The structure fitting experiment showed that the C-terminus was located underneath the prominent density in the VLP/C-tag density map (FIG. 5A and 5B) and the alpha-helix (residues 604-607) and beta-sheet (residues 577-585) were exposed to the interface between Fab224 and VLP so that the beta-sheet oriented downward from the surface and connected by a loop curved in a U-shape to an alpha-helix turning upward to the top surface again. The residues 591-607 recognized by the neutralizing antibody reported by Schofield et al (Schofield et al., 2003. Vaccine 22:257-67.) were also covered by the footprint of MAb224 (FIG. 6A). As indicated in FIG. 6B, the essential epitope located not only at the lateral sides of the capsid protrusions, but also in the vicinity on the top of the protruding surface extended by the C-terminus of the capsid protein.

Discussion

Expressing the truncated HEV ORF2 protein in either Tn5 or Sf9 cells results in self-assembled VLPs of similar structure (Li et al., 2005. J Virol 79:12999-3006.). The recombinant VLP and native virion share antigenic properties because both capable of inducing systemic and mucosal immune responses (Li et al., 2001. Vaccine 19:3476-84.) as well as the HEV specific neutralizing immune responses (Li et al., 2004. Vaccine 22:370-7.) in experimental animals. Earlier identified cryo-EM three-dimensional structures showed that the recombinant HEV VLPs form a T=1 icosahedral particle with 30 dimeric protrusions projected ~43 Å radially above a capsid shell (Li et al., 2005. J Virol 79:12999-3006; Xing et al., 1999. Virology 265:35-45.). As the protrusions are the most exposed part of the particle, they were suspected to form the antigenic determinates. Our results provide the first evidence relating the HEV ORF2 protein sequence to its spatial configuration.

Two strategies were independently used for localizing the C-terminus of the truncated ORF2 protein in VLP; namely, the eleven-residue peptide C-tag and MAb224 recognizing the C-terminal region at position 601-608. A comparative analysis of the VLPs with and without the C-tag revealed a significant density difference at the top surface of the P domain around the two-fold axis (FIG. 3A). The shell domain and symmetry appeared to be identical, suggesting that the inserted tag epitope was not directly involved in the protein-protein interactions during the VLP formation. Superimposition of the difference map on the VLP without tag showed that the tag is exposed on the top surface of the P domain (FIG. 3A). This finding is in agreement with a report that the tag epitope is exposed on the VLP surface since it can be recognized with antibodies against this tag epitope as detected in immuno-precipitation and ELISA experiments (Niikura et al., 2002. Virology 293:273-80.). Additionally, this finding suggests the use of the recombinant HEV VLP for constructing a multivalent vaccine since the HEV ORF2 C-terminal region not only contains the HEV neutralizing epitope but also can successfully present foreign epitopes such as the C-tag to immunocompetent cells.

The monoclonal antibody (MAb224) can recognize the terminal region at position 601-608 at shown by the Western blot analysis (FIG. 1A). The HEV ORF2 proteins truncated at position 600 could not bind to MAb224. This finding suggests that the antigenic site recognized by MAb224 is at least a part of a linear epitope located at the C-terminus. However, it is conceivable that a conformational epitope at the C-terminus may be preserved in denaturing condition if the ORF2 protein were to form a rigid secondary structure capable of withstanding this condition. Similar results have been obtained by Schofield et al. (Schofield et al., 2000. J Virol 74:5548-55.), who originally hypothesized that the neutralizing epitope located at the C-terminus of the ORF2 protein from genotype 1 HEV was linear; but later after examining a shorter peptide comprising residues 589-607 that failed to interact with the neutralizing antibodies in the denaturing RIPA, suggested that this epitope(s) is conformational (Schofield et al., 2003. Vaccine 22:257-67.). Since the site recognized by MAb224 overlaps with the neutralizing epitope (Li et al., 2005. J Biol Chem 280:3400-6; Meng et al., 2001. Virology 288:203-11; Schofield et al., 2003. Vaccine 22:257-67.), the MAb224 binding to the recombinant VLP may be considered as a model for the neutralizing interaction. We used the Fab fragment (Fab224) produced from Mab224 to study antibody binding to the C-terminal region of the HEV ORF2. This experiment suggests that the HEV neutralization mechanism involves the abrogation of the virus attachment to cell. In the detailed analysis of the antigenic site located at C-terminus, Schofield et al. showed that the antibodies, HEV#4 and HEV#31, recognized amino acids between 597 and 607 are capable to neutralize HEV (Schofield et al., 2003. Vaccine 22:257-67.), and the epitope recognized by those antibodies is overlapped with the site recognized by MAb224. The neutralizing activity of MAb224 has not yet been examined. However, our three-dimensional reconstruction of VLP/MAb224 suggests the MAb224 antigenic site is exposed at the lateral sides of the P domain. The long dimension of the MAb224 density extends ~53 Å radially away from the surface of the P domain (FIG. 3B). This data suggests that the Fab224 binding can cause a steric interference with the cell receptor recognition. Because the binding footprint of MAb224 also covers the epitope recognized by HEV#4 and HEV#31 (FIG. 6A), the neutralizing mechanisms of antibodies HEV#4 and HEV#31 might be similar to Fab224 through blocking the viral attachment pathway.

It has been shown that at least one immunodominant neutralization epitope is commonly shared by all four major HEV genotypes and the peptide encompassing the HEV ORF2 region at position 458 to 607 is able to present this conformational neutralization epitope (Emerson et al., 2006. J Gen Virol 87:697-704; Zhou et al., 2005. Vaccine 23:3157-65.). HEV has only one known serotype. Therefore, this neutralizing epitope should be considered as a major component for the development of a universal vaccine against HEV. The HEV ORF2 protein used in this study shares 93-94% sequence similarity with this protein from other three genotypes. Additionally, the spatial configuration of the P domain is conserved in recombinant VLPs for all HEV genotypes (will be published elsewhere). Since the P domain contains the neutralizing epitope, the dimeric nature of this domain may present the key structural property of this epitope.

We previously reported that the HEV ORF2 protein region 125-601 aa is the essential elements for VLP assembly. Truncation of the C-terminal region at position 600 prevents the VLP formation. Li et al. (Li et al., 2005. J Biol Chem 280: 3400-6.) hypothesized that the hydrophobic region at amino acids 597-602 is a site for dimeric interactions; however, neither our cryo-EM 3D structures nor the predicted model of the C-terminal region supports this hypothesis. Our results showed that the peptide regions (residue 597-602) of the neighboring ORF2 protein molecules are distant from each other. Therefore, the possible reason for the abrogation of VLP formation may be duo to the decrease in stability in the secondary structural element at the C-terminal region which leads to the destruction of dimeric interactions.

In conclusion, the C-terminal region of the HEV ORF2 protein is important for both the presentation of the neutralizing epitope and capsid assembly. In the present study we found the C-terminal region extends from lateral sides to the top surface of the P domain. The significant surface exposure of this domain is consistent with location of the major HEV neutralizing epitope in this domain. The structural analysis of VLP/C-tag suggests that the HEV ORF2 protein C-terminal region may be used for insertion of foreign antigenic epitope and, therefore, may serve as a novel platform for engineering multivalent vaccines. A complex structure of MAb224 conjugated to VLP provides a direct evidence that the MAb224 antigenic site is located at the upper side of the P domain. This implies that the region 609-660 removed from the recombinant VLP does not obstruct the presentation of this neutralizing epitope by native virion, and that the P domain observed in the recombinant VLP is present on the surface of native HEV.

Example 2

Biological and Immunological Characteristics of Hepatitis E Virus-Like Particles Based on the Crystal Structure Hepatitis E virus (HEV) is a causative agent of acute hepatitis. The crystal structure of HEV-like particles (HEV-LP) consisting of capsid protein was determined at 3.5-Å resolution. The capsid protein exhibited a quite different folding at the protruding and middle domains from the members of the families of Caliciviridae and Tombusviridae, while the shell domain shared the common folding. Tyr-288 at the 5-fold axis plays key roles in the assembly of HEV-LP, and aromatic amino acid residues are well conserved among the structurally related viruses. Mutational analyses indicated that the protruding domain is involved in the binding to the cells susceptive to HEV infection and has some neutralization epitopes. These structural and biological findings are important for understanding the molecular mechanisms of assembly and entry of HEV and also provide clues in the development of preventive and prophylactic measures for hepatitis E.

Hepatitis E is an acute viral hepatitis caused by infection with hepatitis E virus (HEV) that is transmitted primarily by a fecal-oral route (Panda S K, Thakral D, Rehman S, Rev Med Virol, 17:151-180 (2007); Purcell R H, Emerson S U, J Hepatol, 48:494-503 (2008)). Numerous epidemic and sporadic cases have occurred in developing countries of Asia, the Middle East, and North Africa, where sanitary conditions are not well-maintained. Hepatitis E affects predominantly young adults, and HEV infection in pregnancy is one of the risk factors for severe disease and death (Navaneethan U, Al Mohajer M, Shata M T, Liver Int, 28:1190-1199 (2008)). Recent epidemiological studies show that significant prevalence of HEV and anti-HEV antibody is found in humans and several animals worldwide, even in developed countries (Meng X J, et al., Proc Natl Acad Sci USA, 94:9860-9865 (1997); Sonoda H, et al., J Clin Microbiol, 42:5371-5374 (2004); Okamoto H, Virus Res, 127:216-228 (2007); Li T C, et al., Emerg Infect Dis, 11:1958-1960 (2005); Yazaki Y, et al., J Gen Virol, 84:2351-2357 (2003)).

HEV is the sole member of the genus Hepevirus within the family Hepeviridae and has a 7.2-kb positive-sense RNA genome (Tam AW, et al. Virology, 185:120-131 (1991)). Five major genotypes have been identified so far (Purcell R H, Emerson S U, J Hepatol, 48:494-503 (2008)). The viruses in the genotypes 1 and 2 are maintained among only humans, while those in the genotypes 3 and 4 are found in pigs or wild animals (Meng X J, et al., Proc Natl Acad Sci USA, 94:9860-9865 (1997); Sonoda H, et al., J Clin Microbiol, 42:5371-5374 (2004); Okamoto H, Virus Res, 127:216-228 (2007)). However, infections of human with genotypes 3 and 4 via zoonotic transmission or blood transfusion were reported in the developed countries, such as Japan and the United States (Li T C, et al., Emerg Infect Dis, 11:1958-1960 (2005); Yazaki Y, et al., J Gen Virol, 84:2351-2357 (2003); Matsubayashi K, et al., Transfusion, 44:934-940 (2004)), suggesting that hepatitis E caused by infection with genotypes 3 and 4 of HEV is an important emerging infectious disease. The viruses in the genotype 5 are of avian origin and are thought to be uninfectious to humans (Huang F F, et al. J Gen Virol, 85:1609-1618 (2004)). The genomic RNA contains three ORFs (ORFs) encoding nonstructural proteins (ORF1), the viral capsid protein composed of 660 amino acids (ORF2) and a small phosphorylated protein of unidentified function (ORF3) (Panda S K, Thakral D, Rehman S, Rev Med Virol, 17:151-180 (2007); Tam A W, et al. Virology, 185:120-131 (1991)). The viral capsid protein induces neutralizing antibodies by its immunization (Emerson S U, et al. J Gen Virol, 87:697-704 (2006); He S, et al., J Gen Virol, 89:245-249 (2008); Meng J, et al., Virology, 288:203-211 (2001); Takahashi M, et al., Arch Virol, 153:657-666 (2008)) or during the course of infection (Schofield DJ et al., J Virol, 74:5548-5555 (2000); Schofield D J et al., Vaccine, 22:257-267 (2003)). A typical signal sequence at the N terminus and 3 potential N-glycosylation sites (Asn-X-Ser/Thr) are well-conserved in the capsid protein derived from all mammalian genotypes (Graff J, et al., J Virol, 82:1185-1194 (2008); Zafrullah M et al., J Virol, 73:4074-4082 (1999)), but the glycosylation status of this protein is still controversial and the biological significance of the modification in the viral life cycle remains unknown. Although propagation of HEV in the cell culture systems reported in earlier studies was not efficient (Huang R, et al., Clin Diagn Lab Immunol, 6:729-733 (1999); Kazachkov Yu A, et al., Arch Virol, 127:399-402 (1992); Meng J, Dubreuil P, Pillot J, J Clin Microbiol, 35:1373-1377 (1997); Tam A W, et al., Virology, 238:94-102 (1997)), Tanaka et al. succeeded in the establishment of a persistent infection system of HEV genotype 3 in human hepatoma (PLC/PRF/5) and human carcinomic alveolar epithelial (A549) cell lines (Tanaka T et al., *J Gen Virol*, 88:903-911 (2007)). However, sufficient amounts of viral particles cannot be obtained for studies of the structure, life cycle, and pathogenesis of HEV.

Electron microscopy of human stool specimens showed that HEV is a nonenveloped spherical particle with a diameter of approximately 320 Å (Bradley D, et al., *J Gen Virol*, 69:731-738 (1988)). As an alternative to in vitro propagation of HEV, the baculovirus expression system opens the prospect of studying HEV capsid assembly, since HEV-like particles (HEV-LP) with protruding spikes on the surface can be formed in insect cells infected with a recombinant baculovirus expressing the capsid protein of a genotype 1 strain (Li T C, et al., *J Virol*, 71:7207-7213 (1997); Li T C, et al., J Virol, 79:12999-13006 (2005); Xing L, et al., *Virology*, 265:35-45 (1999)). Cryo-electron microscopic (cryoEM) analysis has revealed that HEV-LP is a T=1 icosahedral particle composed of 60 copies of truncated products of ORF2 (Li T C, et al., *J Virol*, 79:12999-13006 (2005); Xing L, et al., *Virology*, 265: 35-45 (1999)). The HEV-LP appeared to be empty due to a lack of significant density containing RNA inside and was 270 Å in diameter (Li T C, et al., *J Virol*, 71:7207-7213 (1997); Li T C, et al., *J Virol*, 79:12999-13006 (2005); Xing L, et al., *Virology*, 265:35-45 (1999)), which is smaller than the diameter of the native virions. However, the HEV-LP retained the antigenicity and capsid formation of the native HEV particles.

The crystal structures of the recombinant or native T=3 viral particles derived from structurally related mammalian and plant viruses, such as recombinant Norwalk virus (rNV; PDB accession code 1IHM) (Prasad BV, et al., *Science*, 286: 287-290 (1999)), San Miguel sea lion virus (SMSV; PDB accession code 2GH8) (Chen R et al., *Proc Natl Acad Sci USA*, 103:8048-8053 (2006)), the members of the family Caliciviridae, and Carnation mottle virus (CARMV; PDB accession code 1OPO) (Morgunova E, et al., *FEBS Lett*, 338:267-271 (1994)), a member of the family Tombusviridae, have been determined at resolutions of 3.4 Å, 3.2 Å, and 3.2 Å, respectively. In this study, to understand the structural basis on HEV, we solved the crystal structure of HEV-LP derived from a genotype 3 strain at 3.5-Å resolution and found differences in the folding of the capsid protein among these viruses. On the other hand, we found several structural similarities of shell formation. In particular, it was revealed that aromatic amino acids (Tyr-288 in the case of HEV-LP) at the 5-fold axis play a crucial role in the hydrophobic interaction required for particle formation and are well conserved among these viruses. Furthermore, mutational analyses depicted the putative cellular receptor-binding regions and epitopes for neutralizing of binding (NOB) antibodies on the 3D structure of HEV-LP. The availability of the 3D structure of HEV-LP at high resolution will provide valuable information not only for analyses of the entry and assembly of HEV, but also for the development of a vaccine for hepatitis E.

Results

Preparation of HEV-LP of a Genotype 3. Upon infection with a recombinant baculovirus possessing a genome of the truncated capsid protein (amino acids 112-608) from a genotype 3 strain under the control of polyhedrin promoter, a large amount of HEV-LP was secreted into the culture supernatant as described in the case of HEV-LP of genotype 1 strain (Li T C, et al., *J Virol*, 71:7207-7213 (1997); Li T C, et al., *J Virol*, 79:12999-13006 (2005); Xing L, et al., *Virology*, 265:35-45 (1999)). The purified HEV-LP of genotype 3 was used for further structural and biological analyses.

Figure 10:
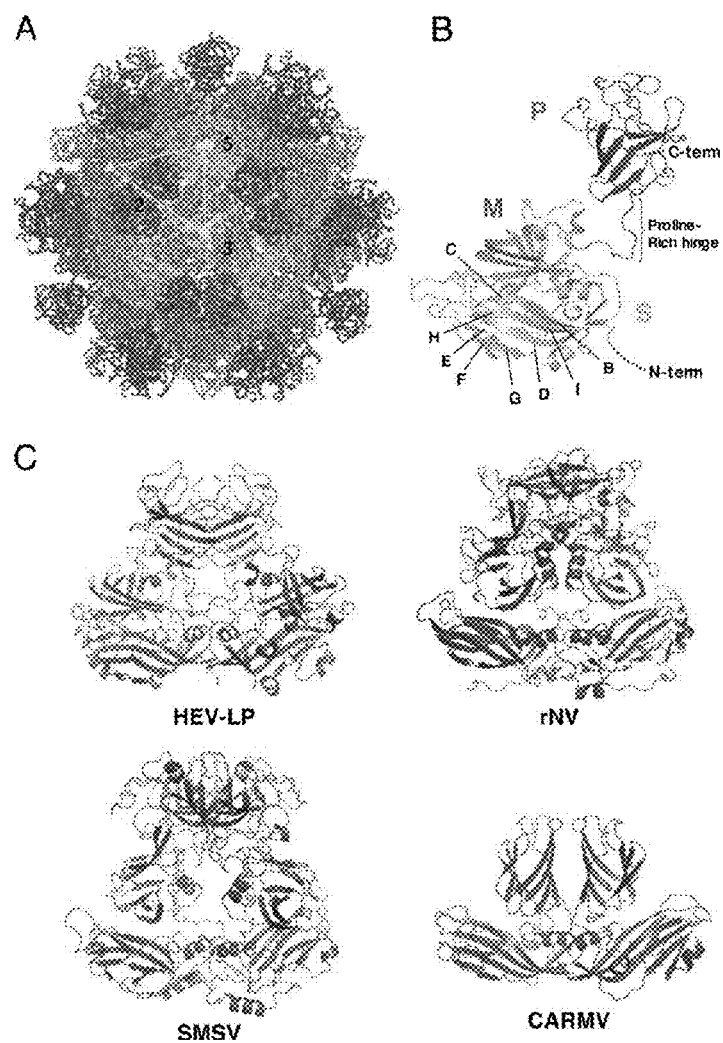
FIG. 10. Crystal structure of HEV-LP and comparison of capsid protein dimers of HEV-LP, rNV, SMSV, and CARMV. The S, M, and P domains of the HEV capsid protein are indicated. (A) HEV-LP is composed of sixty capsid subunits forming icosahedral 2-, 3-, and 5-fold axes and indicating a T=1 symmetry. (B) The ribbon diagram of a capsid subunit of HEV-LP (PDB accession code: 2ZTN) shows P, M, and S domains at the top, middle, and bottom, respectively. The disordered regions are shown with dashed lines. The S domain shows a jerry roll-like β-barrel structure conserved in some viruses. The conserved anti-parallel β-strands are indicated (B to I). (C) The ribbon diagrams of crystal structures of capsid protein dimers of HEV-LP and those of rNV (PDB accession code 1IHM), SMSVc(PDB accession code 2GH8), and CARMV (PDB accession code 1 OPO) are indicated.

Overall Structure of HEV-LP. The crystal structure of HEV-LP derived from the genotype 3 strain was determined at 3.5-Å resolution by the molecular replacement method by using a cryoEM map of HEV-LP derived from the genotype 1 strain (Li T C, et al., *J Virol*, 79:12999-13006 (2005); Xing L, et al., *Virology*, 265:35-45 (1999)) as an initial phasing model (FIG. 10A). As shown in the previous papers (Li T C, et al., *J Virol*, 79:12999-13006 (2005); Xing L, et al., *Virology*, 265: 35-45 (1999)), HEV-LP shows a T=1 icosahedral symmetry with an external diameter of 270 Å. This particle is composed of 60 subunits of the truncated capsid proteins, forming the icosahedral 2-, 3-, and 5-fold axes. It has 30 protrusions at the 2-fold axis of the surface with large depressions at the 3- and 5-fold axes.

Structure of the HEV Capsid Protein. The truncated HEV capsid protein has 3 definite domains designated as S (shell), M (middle), and P (protruding) composed of the amino acid residues 129-319, 320-455, and 456-606, respectively (FIG. 10B). Because the N- and C-terminally truncated capsid proteins were used for the characterization, the typical signal sequence (amino acids 1-22) and following arginine-rich domain (amino acids 23-111) and the C-terminal domain removed by cleavage in insect cells (amino acids 609-660) were not determined in this study. Additionally, the amino acid residues 112-128, 486-487, 555-560, and 607-608 were disordered in this study. The S domain, which forms an internal scaffold structure of the particle, folds into a classical anti-parallel jelly roll-like β-sandwich structure with 8 β-strands (designated as B to I) and 4 short α-helices that are conserved among many viral capsids (FIG. 10B) (Prasad BV, et al., *Science*, 286:287-290 (1999); Chen R et al., *Proc Natl Acad Sci USA*, 103:8048-8053 (2006); Morgunova E, et al., *FEBS Lett*, 338:267-271 (1994); Hogle J M, Chow M, Filman D J, *Science*, 229:1358-1365 (1985); Tsao J, et al., *Science*, 251:1456-1464 (1991)). The M domain, which is one of the characteristic domains, has a twisted anti-parallel β-barrel structure composed of 6 β-strands and 4 short β-helices. This domain is tightly associated with the S domain and located on the surface around the icosahedral 3-fold axis (FIGS. 10A and B). The M and P domains are linked with a long proline-rich hinge (amino acids 445-467). Previous studies on the structures of rNV (Prasad BV, et al., *Science*, 286:287-290 (1999)) and SMSV (Chen R et al., *Proc Natl Acad Sci USA*, 103:8048-8053 (2006)) revealed that the P domains of the viruses are composed of 2 subdomains, P1 and P2, and the P2 subdomain is located as a large protrusion of the P1 subdomain (Fig. S1). In contrast, the P domain of HEV-LP is composed of a single individual domain forming a twisted anti-parallel β-sheets structure (FIG. 10B), demonstrating that the capsid protein of HEV-LP has a significantly different fold from those of caliciviruses, except for the S domain. Although we have no evidence of glycosylation of HEV-LP prepared in insect cells, the HEV capsid protein has 3 potential N-glycosylation sites, Asn-137-Leu-Ser, Asn-310-Leu-Thr and Asn-562-Thr-Thr (Zafrullah M et al., J Virol, 73:4074-4082 (1999)). In the dimer structure, the former 2 sites are mapped on the horizontal surface of the S domain, as shown in Fig. S2A. However, Asn-137 and Asn-310 are located in the interfaces of the pentamer and trimer structures, respectively (Fig. S2B and C), suggesting that, if it occurs at all, N-glycosylation in these sites may inhibit assembly of HEV-LP. Indeed, Graff et al. (Graff J, et al., *J Virol*, 82:1185-1194 (2008)) reported that HEV carrying mutations in Asn-137 or Asn-310 to Glu lost infectivity to cells or rhesus macaques due to a defect in the virion assembly. On the other hand, Asn-562 is mapped in the central region in the top of the P dimer and exposed in the surface of HEV-LP.

The Dimer Structure at the 2-Fold Axis. It is noteworthy that the HEV-LP dimer at the icosahedral 2-fold axis shows a crossing topology of the P versus M and S domains, while that of the other viruses with protrusions at the 2-fold axis, containing rNV, SMSV, and CARMV, exhibits a parallel topology of each domain (FIG. 10C). The flexibility of the long proline-rich hinge region between the M and P domains allows this unique topology of HEV-LP. The P domain of HEV-LP interacts with not only the P domain but also the M domain of the counterpart to stabilize the dimer structure. Despite these topological differences, the overall structure of the protrusion dimeric structure at the 2-fold axis is similar to that of rNV and SMSV. The disordered residues 486-487 and 555-560 are located in the apical region of the protrusion, suggesting that this region is flexible to take advantage of the interaction with other molecules.

Figure 11:
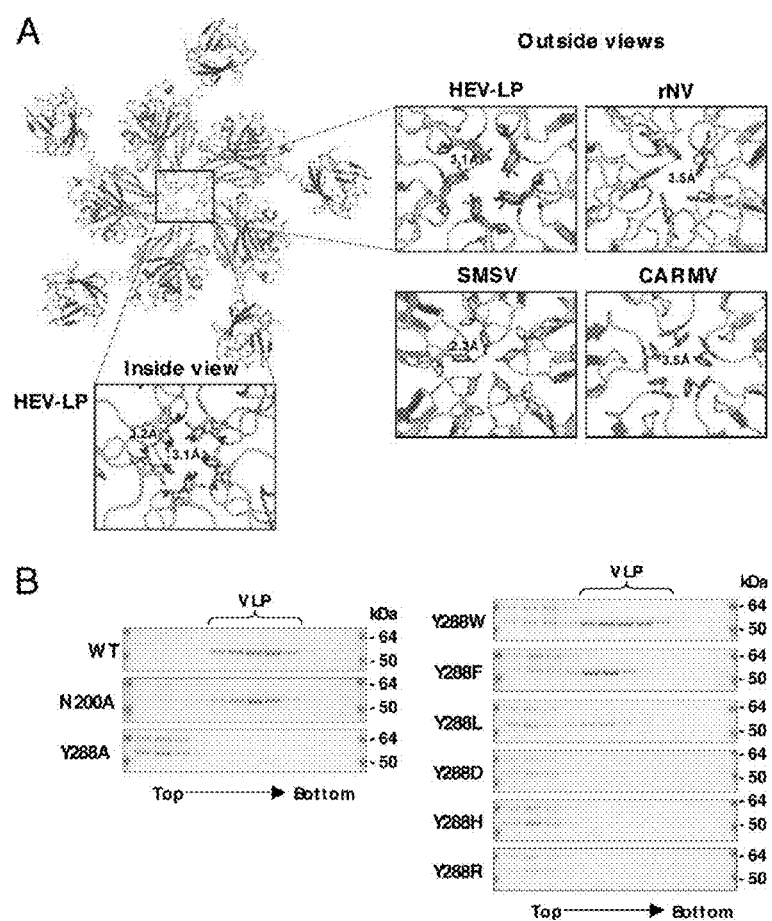
FIG. 11. Interaction of capsid protein subunits of HEV-LP around the 5-fold axis. (A) The pentamer of the capsid protein of HEV-LP. The close-up surface diagram of the 5-fold axis showed from outside and inside of HEV-LP. Amino acid residues Asn-200 and Tyr-288 are shown. The close-up surface diagram of the 5-fold axis showed from outside of rNV, SMSV, and CARMV. The aromatic amino acids Phe-118 of rNV, Tyr-330 of SMSV, and Phe-145 of CARMV are indicated. The deduced interacting atoms are connected with dashed lines, and the distances are indicated. (B) Sucrose density fractionation assay using the wild-type or mutant capsid proteins (53 kDa) in which the amino acids composing the 5-fold axis were substituted. The capsid protein composing HEV-LP was found in the 5-9$^{th}$ fractions from the top, while that which failed to form particles was found in the top fractions. The molecular mass of approximately 64 kDa was a nonspecific protein.

Five-Fold Axis Packaging. The inter-molecule-interface of the capsid pentamer at the icosahedral 5-fold axis is composed of only S domains, and these interaction regions are narrower than those of the dimer and trimer at the 2-fold and 3-fold axes, respectively (FIG. 11A), suggesting that the pentamer formation is a key step of HEV-LP assembly. There are 4 loops between the β-sheets in the S domain, designated as loops B-C (amino acids 139-152), D-E (amino acids 196-206), F-G (amino acids 236-241), and H-I (amino acids 281-296), around the center of the pentamer structure. Among them, the loops B-C and F-G are not in close proximity to the next subunits, suggesting they are not implicated in the intermolecular interaction. In contrast, loops D-E and H-I do interact with the next subunits. In particular, the side chains of Asn-200 and Tyr-288 in loops D-E and H-I, respectively, interact with those of the next subunits, from which they are separated by a distance of approximately 3.2 Å, filling in the central pore (FIG. 11A). These observations led us to hypothesize that these amino acid residues are important for assembly and stability of the particles. To examine this hypothesis, we constructed 2 mutant capsid proteins in which Asn-200 was replaced with alanine (N200A) or Tyr-288 was replaced with alanine (Y288A), and the effect of these mutations on the particle formation was determined by a density-fractionation assay (FIG. 11B). Comparative amounts of the mutant proteins to the wild-type capsid were expressed and released into the supernatants of cells infected with the recombinant baculoviruses. N200A but not Y288A formed VLP as the wild-type, indicating that Tyr-288 plays a more crucial role in particle formation than Asn-200. The aromatic amino acids, Phe-118, Tyr-330, and Phe-145, are also found in the icosahedral 5-fold axis of rNV, SMSV, and CARMV, respectively (FIG. 11A). To examine the role of the aromatic side chain in Tyr-288 in the particle formation, a series of mutants in which Tyr-288 was replaced with tryptophan, phenylalanine, leucine, aspartic acid, histidine, or arginine (Y288W, Y288F, Y288L, Y288D, Y288H, or Y288R) were generated. All of them were expressed and released into the culture medium, as well as was the wild type. The mutants with aromatic amino acids, Y288W and Y288F, were able to form HEV-LP, whereas other mutants produced no or very few particles (FIG. 11B). These results suggest that the aromatic side chain of Tyr-288 plays a crucial role in the HEV-LP formation by shutting off the central pore of the pentamer, and that the aromatic amino acids in the positions corresponding to Tyr-288 of HEV are functionally conserved among the structurally related viruses.

Binding of HEV-LP to Cultured Cells. The early steps of HEV entry remain unclear because of the lack of a robust cell culture system for HEV, despite recent progress in the in vitro propagation of HEV in the cell lines PLC/PRF/5 and A549 (Tanaka T et al., *J Gen Virol*, 88:903-911 (2007)). HEV-LP was able to bind to several cell lines, including PLC/PRF/5 and A549 cells, but not to mouse myeloma P3×63Ag8U.1 (P3U1) cells (Fig. S3), suggesting that a binding assay using HEV-LP is useful to examine the first step of receptor-binding of HEV to the target cells. Among the cell lines examined, the human hepatoma cell line Huh7, exhibited a greater ability to bind to HEV-LP than the cell lines PLC/PRF/5 and A549. Therefore, Huh7 cells were used for the following binding experiments of HEV-LP.

Figure 12:
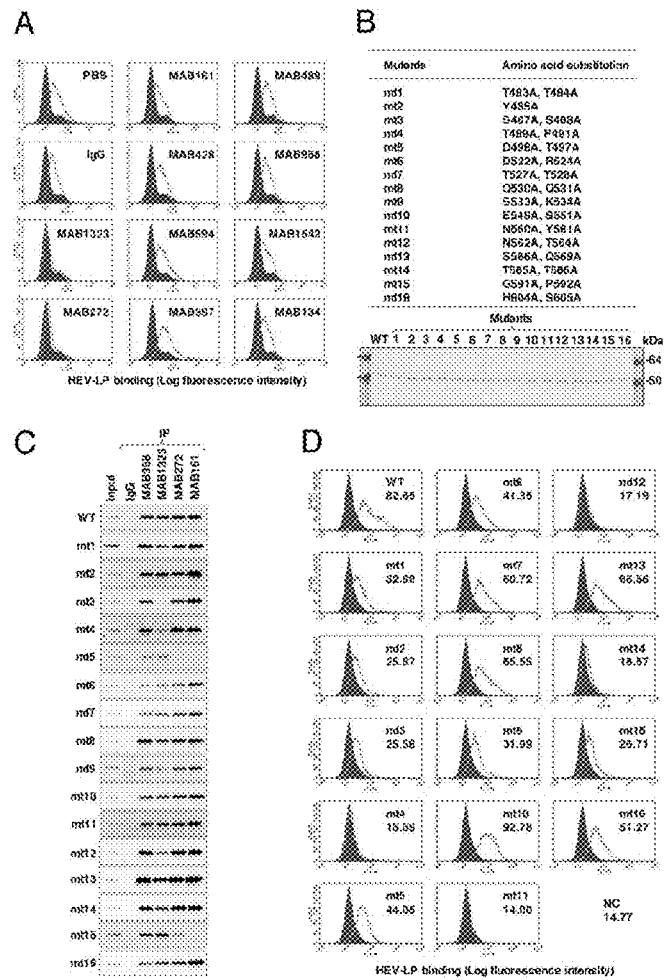
FIG. 12. Characterization of monoclonal antibodies and mutant HEV-LPs. (A) Neutralization of binding (NOB) of HEV-LP to Huh7 cells by monoclonal antibodies to HEV-LP. After preincubation of HEV-LP (10 μg/mL) with each of the monoclonal antibodies (20 μg/mL) for 1 h at 37° C., the mixture was inoculated into Huh7 cells and incubated for 1 h at 4° HEV-LP (lined area) bound to cells was detected by flow cytometry. The filled area indicates mock-incubated cells. (B) Construction of HEV-LP mutants. Sixteen HEV-LP mutants, in which the surface amino acid residues of the P domain were substituted, were constructed. The protein bands of 100 ng each of the purified wild-type and mutant HEV-LPs were visualized by Coomassie brilliant blue staining after SDS/PAGE. (C) Reactivities of NOB antibodies with the mutant HEV-LPs. Immunoprecipitation analyses of a series of HEV-LPs by NOB (MAB1323 and MAB272) or non-NOB antibodies (MAB358 and MAB161). Immunoprecipitated HEV-LPs were detected by an anti-HEV capsid rabbit polyclonal antibody. (D) Binding capability of the mutant HEV-LPs to Huh7cells. Wild-type or mutant HEV-LPs (10 m/mL) were incubated with Huh7 cells for 1 h at 4° C., and then HEV-LP (lined area) bound to cells was detected by flow cytometry. The filled area indicates mock-incubated cells. The MFI is shown in each panel.

Three-Dimensional Mapping of Epitopes for NOB Antibodies. We examined the ability of the 10 newly produced anti-HEV-LP monoclonal antibodies to inhibit the binding of HEV-LP to Huh7 cells (FIG. 12A). Two of the monoclonal antibodies, MAB1323 and MAB272, exhibited NOB of HEV-LP to Huh7 cells and recognized the P domain by immunoblotting using the GST (GST)-fused HEV capsid proteins. However, further truncation of the C-terminal 28 or N-terminal 24 amino acids from the GST-fused P domain abrogated the binding with the antibodies, indicating that it is difficult to determine the epitopes of the antibodies in more detail using a series of truncated mutants of the P domain. A competitive enzyme-linked immunosorbent assay (ELISA) suggested that MAB1323, MAB272, and MAB161, but not MAB358, which was used as a detector in the binding assay, recognized the same or adjacent epitopes (Fig. S5). The P domains of rNV and feline calicivirus were suggested to be involved in the binding to the receptor molecules (Bhella D et al., *J Virol*, 82:8051-8058 (2008); Bu W, et al. *J Virol*, 82:5340-5347 (2008); Choi J M et al., *Proc Natl Acad Sci USA*, 105:9175-9180 (2008)), and we therefore hypothesized that the P domain of HEV-LP might also be involved in the cell binding. To examine this possibility, we prepared 16 HEV-LP mutants in which 1 or 2 amino acid residues at the surface of the P domain were substituted (FIG. 12B). The density fractionation assay indicated that all of the mutant proteins formed HEV-LP in the manner of the wild-type capsid protein. MAB358, which recognized an epitope on the M domain, was capable of precipitating all of the mutants (FIG. 12C). MAB1323 exhibited no interaction with mt3 and a weak precipitation of mt4 and mt12. Both MAB272 and MAB161 exhibited no or weak precipitation of mt5 and mt15, whereas MAB272 but not MAB161 exhibited NOB of HEV-LP to Huh7 cells (FIGS. 12A and C). The substituted amino acids of these mutants are illustrated in the 3D structure of the capsid dimer (FIG. 13A), and these results suggest that the NOB antibodies MAB1323 and MAB272 recognize the peripheral region of the apical surface and the horizontal region of the P domain above the M domain at the 3-fold axis, respectively.

Figure 13:
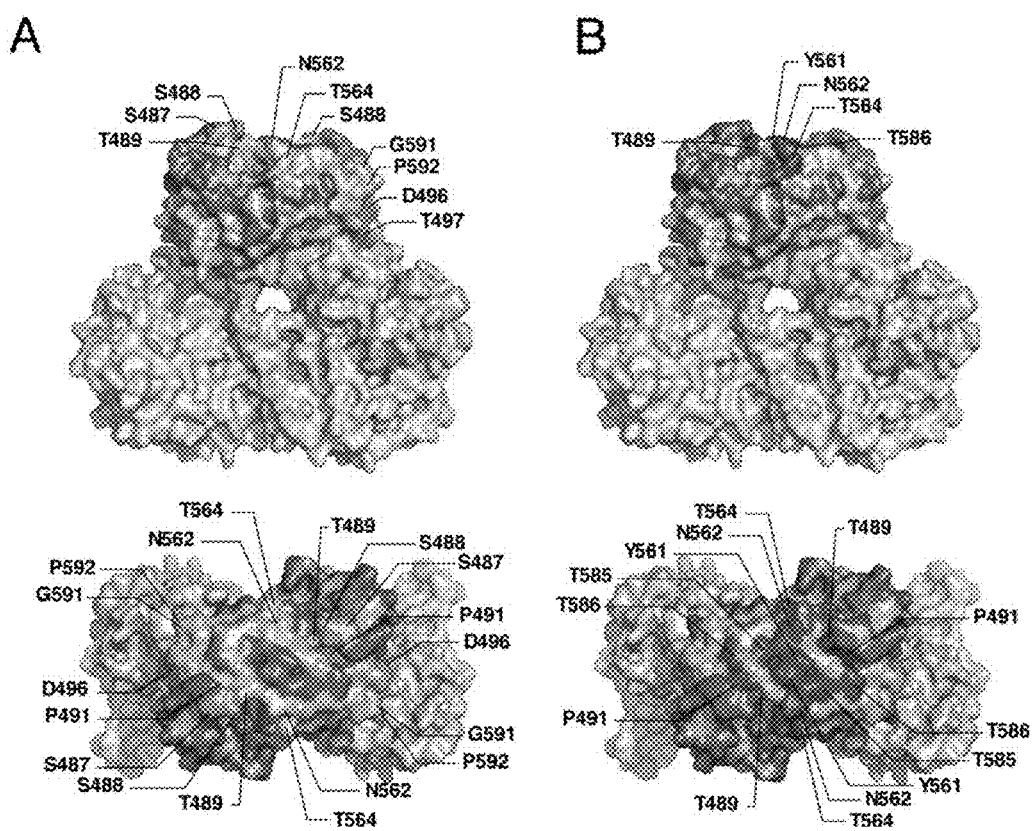
FIG. 13. Amino acid residues involved in the recognition by NOB antibodies and in the binding to Huh7 cells. Surface diagrams of the capsid protein dimer from a lateral (Upper) or top (Lower) view. (A) Amino acids in HEV-LP involved in the complete loss or reduction of reactivity to MAB1323 and MAB272 are shown. (B) Amino acids in HEV-LP responsible for binding to Huh7 cells are shown. The substitutions in the P domain of HEV-LP that exhibited no effect on the reactivity with NOB antibodies or the binding to Huh7

Three-Dimensional Mapping of a Region Crucial for Binding to the Target Cells. To determine the region important for binding to the cell surface, the mutant HEV-LPs substituted into the P domain were also used in the assay of binding to Huh7 cells (FIG. 12D). The wild-type HEV-LP bound to Huh7 cells with a geographic mean fluorescence intensity (MFI) of 82.65. Among the mutants examined, mt4, mt11, mt12, and mt14 exhibited significantly low MFI values of less than 20. Similar results were obtained using A549 cells. The amino acid residues required for cell binding were mapped in the central flexible region of the apical surface as shown in FIG. 13B. This region is partially overlapped with epitopes of MAB1323 (FIG. 13A) and other neutralizing antibodies reported by Schofield et al. (Schofield D J et al., *J Virol*, 74:5548-5555 (2000)) as shown in Fig. S7. These results suggested that the apical center region of the P domain is involved in the association with not-yet-identified cellular receptor(s).

Discussion

The expression of the truncated HEV capsid protein (amino acids 112-608) in insect cells resulted in assembly of HEV-LP, which retains an antigenicity similar to that of the native HEV particles (Li T C, et al., *J Virol*, 71:7207-7213 (1997); Li T C, et al., *Virology*, 349:222-229 (2004)). This particle with a T=1 symmetry has a diameter of 270 Å, which is smaller than the 320-Å diameter of the native virion detected in the fecal specimens of patients (Bradley D, et al., *J Gen Virol*, 69:731-738 (1988)). It has been reported that the interior cavity of HEV-LP is too small to accommodate a viral RNA of 7.8 kb in length (Xing L, et al., *Virology*, 265:35-45 (1999)) and that the particles show no evidence of nucleotide contents (Li T C, et al., *J Virol*, 71:7207-7213 (1997); Xing L, et al., *Virology*, 265:35-45 (1999)). Therefore, native HEV particles are suggested to be composed of a larger number and/or a larger size of capsid proteins than HEV-LP. In some cases of plant viruses with a T=3 symmetry, the capsid proteins assembled into particles with a T=1 symmetry by deletion of the N-terminal basic region (Hsu C, et al., *Virology*, 349:222-229 (2006); Kakani K et al., *J Virol*, 82:1547-1557 (2008)) or amino acid substitutions either in the N-terminal region or in the linker domain between the N-terminal region and S domain (Kakani K et al., *J Virol*, 82:1547-1557 (2008)), suggesting that the N-terminal basic region plays an important role in switching of the transition from T=3 to T=1 symmetry. In addition, expression of the NV capsid protein in insect cells resulted in production of not only T=3 large particles but also small particles thought to have the T=1 symmetry (White L J, Hardy M E, Estes M K, *J Virol*, 71:8066-8072 (1997)). Based on many similarities of the capsid structures and their packaging of structurally related viruses, the native HEV particles are suggested to possess a T=3 surface lattice. The flexibility of the proline-rich hinge linking the M and P domains could allow the capsid protein dimer to switch conformations between the A/B and C/C subunits found in T=3 viruses. Although structure of the native HEV may be slightly different from that of the HEV-LP, the data obtained in this study by using HEV-LP should provide useful information to understand the structure of viral particle, life cycle, and pathogenesis of HEV. The S domain shares the jellyroll fold with some other icosahedral viruses (Prasad B V, et al., *Science*, 286:287-290 (1999);Chen R et al., *Proc Natl Acad Sci USA*, 103:8048-8053 (2006); Morgunova E, et al., *FEBS Lett*, 338:267-271 (1994); Hogle J M, Chow M, Filman D J, *Science*, 229:1358-1365 (1985); Tsao J, et al., *Science*, 251:1456-1464 (1991)). It was found that the capsid proteins with substitutions of Tyr-288 positioned at the center of the pentamer structure built in interS domain-interaction failed to assemble into HEV-LP. Alignment analysis of amino acid sequences using data available in GeneBank showed that Tyr-288 is completely conserved within 5 genotypes of HEV. Furthermore, residues corresponding to Tyr-288 of the HEV capsid protein are found in the structures of rNV (Phe-118), SMSV (Tyr-330), and CARMV (Phe-145), although the positions of these aromatic residues are different. Tyr-288 of HEV and Tyr-330 of SMSV located in the H-I loop and Phe-110 of rNV in the D-E loop are exposed at the outside surface of the particles, whereas Phe-145 of CARMV located in the D-E loop is exposed at the interior of the particle. These data suggest that the aromatic side chains of these residues are involved in hydrophobic interactions with those of the next subunits, assuring stable assembly of the particles. During entry into cells, rearrangement of the virion structure is required for release of the genome from the shell. However, the entry and uncoating mechanisms of HEV remain unknown. Because the center of the pentamer is the thinnest region of the particle and takes a channel-like structure (Xing L, et al., *Virology*, 265:35-45 (1999)), this region might also be important for uncoating and release of the viral RNA. It has been proposed that the 5-fold axis of poliovirus is involved in the genomic RNA translocation via conformational change of the virion initiated by binding to the receptor molecules (Belnap D M, et al. *J Virol*, 74:1342-1354 (2000); Bubeck D, Filman D J, Hogle J M, *Nat Struct Mol Biol*, 12:615-618 (2005)).

The first step in viral entry into a target cell is binding to the cellular receptors. The human hepatoma PLC/PRF/5 and lung epithelial A549 cell lines, which are highly susceptible to persistent HEV-infection (Tanaka T et al., *J Gen Virol*, 88:903-911 (2007)), are likely to express functional HEV receptors on the cell surface. However, HEV-LP had reduced binding to these cells compared to the other cell lines examined. Therefore, the human hepatoma cell line Huh7, which also exhibited a susceptibility to HEV infection (He S, et al., *J Gen Virol*, 89:245-249 (2008); Graff J, et al., *J Virol*, 82:1185-1194 (2008)) and readily bound to HEV-LP, was mainly used in this study. It has been reported that the P domains of noroviruses and the feline calicivirus were involved in the binding to the putative receptors, histo-blood antigens (Bu W, et al. *J Virol*, 82:5340-5347 (2008); Choi J M et al., *Proc Natl Acad Sci USA*, 105:9175-9180 (2008)) and the feline junctional adhesion molecule (Bhella D et al., *J Virol*, 82:8051-8058 (2008)), respectively. The peptide of the HEV capsid protein (amino acids 368-606), which consists of a part of the M and an entire P domain, was shown to be capable of binding to several cell lines (He S, et al., *J Gen Virol*, 89:245-249 (2008)), suggesting that the P domain of HEV is also involved in the binding to the cell receptors. Indeed, the mutational analyses in this study indicated that the central flexible region of the top of the P domain of HEV-LP plays a crucial role for binding to Huh7 and A549 cells. This is consistent with a recent study by Graff et al. in which an N562Q mutant of HEV lost infectivity to culture cells and rhesus macaques despite the production of viral particles (Graff J, et al., *J Virol*, 82:1185-1194 (2008)). Interestingly, a possible N-glycosylation site, Asn-562-Thr-Thr, is mapped in this region. N-glycosylation is an unusual posttranslational modification for nonenveloped viruses, except for rotaviruses (Jayaram H, Estes M K, Prasad B V, *Virus Res*, 101:67-81 (2004)). The mutant capsid mt12, which has substitutions of Asn-562 and Thr-564 to alanine, exhibited the same migration as the wild-type protein in SDS/PAGE, suggesting that the HEV-LP produced in insect cells was not glycosylated at Asn-562. Lack of N-glycosylation in the capsid protein has also been reported in mammalian cells infected with HEV (Graff J, et al., *J Virol*, 82:1185-1194 (2008)), whereas some portion of the capsid protein was glycosylated and transported to the cell surface upon overexpression in mammalian cells (Zafrullah M et al., *J Virol*, 73:4074-4082 (1999)). N-glycosylation of the HEV capsid at Asn-562 may have a negative effect on the receptor-binding, whereas it may play a positive role in other functions, including pathogenesis. The biological significance of the glycosylation of HEV capsid protein remains to be studied.

Although there is currently a lack of sensitive and reliable assays to determine the neutralizing activity of anti-HEV antibodies, the assay of NOB of HEV-LP binding to the target cells is thought to be a suitable alternative method. Measurement of the reactivity of a panel of mutant HEV-LPs revealed that the epitopes of MAB1323 and MAB272 antibodies are mapped in the peripheral region of the apical surface and the horizontal region of the P domain dimer, respectively. These results further support the notion that the P domain of HEV-LP is important for the binding to cells. MAB1323 is suggested to directly inhibit the interaction between HEV-LP and cellular receptors through binding to the apical surface, whereas MAB272 may have an allosteric effect, inducing conformational change of the P domain through binding to the horizontal region. A number of monoclonal antibodies are capable of neutralizing in vitro and in vivo infection of HEV (Emerson S U, et al. *J Gen Virol*, 87:697-704 (2006); He S, et al., *J Gen Virol*, 89:245-249 (2008); Meng J, et al., *Virology*, 288:203-211 (2001); Takahashi M, et al., *Arch Virol*, 153: 657-666 (2008); Schofield D J et al., *J Virol*, 74:5548-5555 (2000); Schofield D J et al., *Vaccine*, 22:257-267 (2003)), and many of them recognize conformational epitopes of the capsid protein, as seen in the MAB1323 and MAB272 antibodies prepared in this study. Monoclonal antibodies against linear epitopes located in amino acids 578-607 of a genotype 1 capsid protein (Schofield D J et al., *J Virol*, 74:5548-5555 (2000)) were overlapped with a part of the putative receptor-binding domain and the epitope of MAB272, supporting the data of the present study. On the other hand, monoclonal antibodies against the linear epitopes located in amino acids 423-438 and amino acids 423-443 in the M domain of a genotype 1 capsid protein neutralized binding of a peptide derived from the capsid protein to cells and HEV-infection (He S, et al., *J Gen Virol*, 89:245-249 (2008)), suggesting the importance of the M domain in the binding step.

In summary, we have determined the crystal structure of HEV-LP produced in insect cells and demonstrated its structural characteristics in comparison with the structurally related animal and plant viruses. This study will provide useful information for elucidation of the molecular mechanisms of HEV-life cycles and for the development of prophylactic and therapeutic measures for hepatitis E.

Materials and Methods

Expression, Purification, and Crystallization of HEV-LP. The recombinant baculovirus encoding the ORF2 of the HEV genotype 3, 2712 strain was expressed in insect cells. HEV-LP was purified as described previously (Xing L, et al., *Virology*, 265:35-45 (1999)) and crystallized by the hanging-drop vapor-diffusion method. Details are reported in SI Materials and Methods.

Data Collection and Phase Determination. x-ray diffraction data were collected at 100 K on beamlines BL17A at the Photon Factory (KEK). The statistics of X-ray diffraction data collection are summarized in Table 1. The solved 3D structure of HEV-LP was submitted to the Protein Data Bank under the PDB accession code of 2ZTN. Details are reported in SI Materials and Methods.

TABLE 1

Data collection and processing statistics for HEV-LP

| Data collection | |
| --- | --- |
| Space group | P2₁2₁2₁ |
| Cell dimensions | |
| a, b, c, Å | 336.8, 349.4, 359.5 |
| X-ray wavelength, Å | 1.0000 |
| Resolution, Å | 50-3.55 (3.68-3.55) |
| $R_{merge}$* | 0.131 (0.498) |
| I/σI | 9.8 (3.2) |
| Completeness, % | 99.9 (99.8) |
| Redundancy | 5.6 (5.2) |

TABLE 1-continued

Data collection and processing statistics for HEV-LP

| Refinement | |
| --- | --- |
| Resolution range, Å | 20-3.56 |
| No. reflections | 494, 466 |
| $R_{work}/R_{free}$ | 30.5/30.9 |
| No. atoms | |
| Protein | 215, 400 |
| B factors | |
| Protein rmsd | 94.9 |
| Bond length, Å | 0.009 |
| Bond angle, ° | 1.355 |

Values in square brackets refer to the highest-resolution shell.
*$R_{merge}$* = $\Sigma_{hkl} \Sigma_i |I(hkl)_i - <I(hkl)>|/\Sigma_{hkl} I(hkl)$, where $I(hkl)_i$ is the ith measurement of the intensity of reflection hkl and $<I(hkl)>$ is the mean intensity of reflection hkl.

Example 3

Structural Characterization of Predominant Antigenic Region on HEV Capsid Protrusion Domain Hepatitis E virus (HEV) is a human pathogen that causes acute liver failure. When expressed in insect cell with deletion of 52 amino acid from the C-terminus and 111 amino acids from the N-terminus, the capsid protein can self-assemble into T=1 virus like particle (VLP) that retains the antigenicity of native HEV virion. Here, using cryo-electron microscopy and image reconstruction, we determined that the anti-HEV monoclonal antibodies bound to the protruding domain of the capsid protein, with 60 copies of Fab fragment per VLP. The molecular docking of HEV crystal structure revealed that the binding site of the antibody Mab224 covered three PORF2 surface loops at the rim of the surface plateau. This antibody binding site is separated from the potential location of the inserted B-cell tag, an epitope of 11 amino acids fused to the C-terminal end of the PORF2 protein, as it determined with the cryo-EM structure of chimeric HEV VLP. Therefore, the T=1 HEV VLP is a robust delivery candidate that induces effectively antibodies against both HEV and the foreign epitope.

Hepatitis E virus (HEV), a causative viral agent of acute liver failure in human, is primarily transmitted via fecal-and-oral route thus resistant to low pH and digestive enzymes associated with stomach and digestive tracts. The infection of HEV can result in epidemic outbreaks in many tropic and subtropics countries. It is found that more than 50% of reported acute viral hepatitis cases are attributed to HEV in adult population in India (Arankalle, V. A. et al., *Proc Natl Acad Sci USA* 91:3428-32 (1994)) and 90% of jaundice hepatitis cases in the city of Kathmandu, Nepal in 1996 (Clayson, E. T. et al., *Nepal. J Infect Dis* 176:763-6 (1997)). In India, 101 outbreaks were confirmed by serological analysis in the state of Maharashtra during 2002-2007 (Deshmukh, T. M. et al., *Vaccine* 25:4350-4360 (2007)). The life risk of HEV infection in India is greater than 60% (Worm, H. C. *Drugs* 64:1517-1531 (2004)). Sporadic cases have also been reported between outbreaks in HEV-endemic regions as well as in non-endemic areas. Although some of these cases were associated with travel to endemic regions, many cases involved patients without such a travel history. Accumulating evidence suggests that sporadic infection occurs through zoonotic routes, and hepatitis E cases also prevalent in well-developed countries, including the United States (Purcell, R. H. et al., *J Hepatol* 48:494-503 (2008)). The overall death rates of HEV during outbreaks range from 1 to 15% in general and the highest mortality occurs in pregnant women, with fatality rates of up to 20% (Patra, S. et al., *Ann Intern Med* 147:28-33 (2007)). More over, HEV superinfection is documented to cause high rate of hepatic decompensation (Kumar, A. S. et al., *J Hepatol* 46:387-394 (2007)) and progression of acute hepatitis E to chronical liver disease is also reported in the organ-transplant recipients (Kamar, N. et al., *N Engl J Med* 358:811-817 (2008)).

The HEV virion is composed of a single-stranded RNA molecule of 7.2 kB in size and an icosahedral capsid reported to be 32-34 nm. The HEV capsid protein of 660 amino acids (ORF2 protein) is encoded by the second open reading frame and is responsible for most capsid-related functions, such as assembly, host interaction, and immunogenicity. Recombinant ORF2 protein can induce antibodies to prevent HEV infection in non-human primates (Li, T.-C. et al., *Vaccine* 22:370-377 (2004); Purcell, R. H. et al., *Vaccine* 21:2607-15 (2003); Tsarev, S. A. et al., *Vaccine* 15:1834-1838 (1997)). Four major antigenic domains were predicted to be located in the C-terminal 268 amino acids of ORF2 proteins (Meng, J. et al., *Virology* 288:203-211 (2001)), one of which was experimentally identified as the neutralization epitope on the Sar-55 ORF2 capsid protein (Schofield, D. J. et al., *J Virol* 74:5548-5555 (2000)). A truncated ORF2 peptide containing residues 459-607 of ORF2 protein presents the minimal peptide needed to induce anti-HEV neutralizing antibody (Zhou, Y. H. et al., *Vaccine* 23:3157-3165 (2005)), suggesting that the HEV neutralizing epitope is conformation-dependent. Currently, there are 1,600 genomic sequences of HEV available at the International Nucleotide Sequence Database Collaboration, which are grouped into four genotypes. Notably, only a single known serotype is recognized and the antibodies from any one of the four genotypes broadly cross-reactive with genotype-1 HEV virus, suggesting that the immunodominant domain of HEV is highly conserved. (Emerson, S. et al., *J Gen Virol* 87:697-704 (2006)).

Like other hepatitis viruses, HEV is unable to propagate in large quantities in current cell culture systems. Development on HEV preventive strategies rely on recombinant protein derived from the HEV capsid protein. When expressed in insect cell, the recombinant ORF2 protein self-assembles into virus-like particles (VLPs) after deletion of 52 residues from the C-terminus and 111 residues from the N-terminus (PORF2) (Li, T. C. et al., *J Virol* 71:7207-7213 (1997)). Our previous structural analysis of recombinant HEV-VLP by cryo-electron microscopy (cryo-EM) provided a basic understanding of the quaternary arrangement of PORF2, where the reconstructed VLP displayed a T=1 icosahedral particle composed of 60 copies of truncated PORF2 (Xing, L. et al., *Virology* 265:35-45 (1999)) and the essential assembly element of PORF2 protein contained amino acids 125-600 (Li, T.-C. et al., *J. Virol.* 79:12999-13006 (2005)). Recently, crystal structures were reported for genotype-3 T=1 VLP (Yamashita, T. et al., *Proc Natl Acad Sci USA* 106:12986-12991 (2009)) and genotype-4 T=1 VLP (Guu, T. et al., *Proc Natl Acad Sci USA* 106:12992-12997 (2009)), which revealed that PORF2 is composed of three domains. Although these VLPs (270 Å in diameter) is smaller than the native HEV virion (320-340 Å), this HEV-VLP can induce anti-HEV antibody when orally administered to experimental animals (Li, T. et al., *Vaccine* 19:3476-3484 (2001)).

There is a need of structural information on HEV antigenic epitopes for the development of preventive strategies. Here, we present a series of experiments using cryo-EM and three-dimensional reconstruction to identify the antigenic structure. Our results indicate that the antibody-binding footprint covered the lateral side of the P domain and separated from the location of the inserting B-cell tag.

Materials and Methods

Production and Purification of Anti-HEV Monoclonal Antibodies

Eight-week-old female BALB/c mice were immunized at 0 and 4 weeks by intraperitoneal inoculation with HEV VLPs (100 ug/ml). Four weeks later, a final boost of equal volume of antigen was administered. Three days after the final boost, mouse spleen cells were fused with P3U1 mouse myeloma cells using polyethylene glycol 1500 (50% [w/v]) (Boehringer Mannheim, Germany) as essentially described previously (Adler, B. et al., *Pathology* 15:247-250 (1983)). Supernatant from microplate wells positive for hybridoma growth was screened by ELISA using the recombinant HEV VLPs as antigen. Hybridomas secreting specific antibodies to HEV were subcloned three times by limiting dilution, after which they were considered to be monoclonal. Antibodies in the supernatants were isotyped using the Mouse Monoclonal Antibody Isotyping kit (Amersham, Little Chalfont, Buckinghamshire, U.K.) in accordance with the manufacturer's protocol. Hybridomas were grown in bulk in stationary flasks (Nunc, Roskilde, Denmark) using PRMI-1640 with 15% FCS. Supernatant was harvested and antibodies were purified using HiTrap protein G affinity columns (Pharmacia Biotech AB, Uppsala, Sweden) and stored at −80° C. Among all the antibodies, Mab224 used in our analysis is immunoglobulin G1 (IgG1) isotype.

Preparation of Fab Fragments

Papain cleavage was used to prepare isolated Fab fragments. A reducing L-cystein buffer was used to activate papain, and the MAb224 was mixed with papain at a molar ration of 100:1. The mixture was incubated overnight at 30° C. The reaction was quenched by adding iodacetamide and product was analyzed on SDS-PAGE. The Fab fragments were purified using a Protein-A column according to the manufacturer's instruction. The Fc fragments and uncleaved Mab224 were trapped in the column due to the affinity to protein-A while the Fab fragments were collected in the flow-through fractions.

Preparation and Purification of the HEV VLPs

The production and purification of HEV VLPs were performed according to the protocol described earlier (Li, T. C. et al., *J Virol* 71:7207-7213 (1997); Niikura, M. et al., *Virology* 293:273-280 (2002)). Briefly, the DNA fragments containing the N-truncated ORF2 protein (for wild VLP), and chimeric ORF2 protein (for VLP/C-tag) were cloned with baculovirus transfer vector pVL1393 to yield pVLORF2. The recombinant baculoviruses were produced from Sf9 insect cells (Riken Cell Bank, Tsukuba, Japan) and then infected Tn5 insect cell at a M.O.I.>5. The infected insect cells were incubated in EX-CELL™ 405 medium (JRH Biosciences, Lenexa, Kans.) for 6 days at 26.5° C. The culture medium was collected after removal of cell debris by centrifugation at 10,000 g for 90 min. The supernatant was spun down at 30,000 rpm for 2 h in a Beckman SW32 Ti rotor and pellet was resuspended in 4.5 ml EX-CELL™ 405. The pellet contained HEV VLP and was further purified within CsCl density gradient. The white virus-band was collected and diluted 4 times with EX-CELL™ 405 to remove CsCl by centrifugation (2 h in a Beckman TLA 55 rotor at 45,000 rpm). The VLPs were re-suspended in 100-500 μl of 10 mM potassium-MES buffer and stored at 4° C. To construct chimeric VLP/C-tag, the recombinant baculoviruses was prepared by inserting B-cell tag epitope from glycoprotein D of herpes simplex virus "QPELAPEDPED" (SEQ ID NO:7) after residue 608 (Schofield, D. J. et al., *Vaccine* 22:257-267 (2003)). The VLP/C-tag is prepared and purified with the protocol described above.

Preparation of VLP-Fab Complexes for Cryo-Electron Microscopy

The VLP/Fab complexes were prepared by incubating Fab fragments with VLP at a molar ratio exceeding 1:300 at 4° C. overnight. Unbound Fab fragments were removed by running the sample through a short gel-filtration column containing Sephacryl-300. The fractions containing VLP/Fab complexes were identified based on reading of OD280 nm. The Fab binding occupancy was roughly estimated by SDS-PAGE, in which the purified VLP/Fab complexes were loaded on an acrylamide gel (gradient 8-25%) and electrophoresis was run on a Phast™ system (Pharmacia) under constant-voltage condition. The integrity of particles was checked by electron microscopy (EM) after negatively stained with 2% uranyl acetate (UA).

Cryo-electron Microscopy

The sample preparation and cryo-EM data collection were followed a well-established procedures described previously (Xing, L. et al., *Virology* 265:35-45 (1999)). Briefly, a drop containing 3.5 µl of sample was applied on a glow-discharged homemade holey-carbon grid, blotted with a piece of filter paper to remove the extra liquid and quickly plunged into liquid ethane cooled by liquid nitrogen. The frozen-hydrated specimen grid was then transferred into a FEI CM-120 electron microscope with a Gatan 626DH cryo-holder which kept specimen at the low temperature environment (−178° C.) for the subsequent data collection. Micrographs were recorded under low-dose condition (<10 e-/$Å^2$) on Kodak SO163 films at a magnification of 45,000× with the defocus range from 1000 to 3000 nm. Micrographs were visually selected based on the criteria of suitable particle concentration, optimal ice thickness and minimal specimen drift. Only those micrographs fulfilling these criteria were analyzed.

Image Processing

Selected micrographs were digitized using a Heidelberg Primescanner D8200 (Heidelberg, Germany) at a 14 µl scanning step size, corresponding to 3.11 Å per pixel at specimen space. Particles were manually picked using Robem (v2.14), and centered by cross-correlating each of them against the circular average image. The astigmatism and the defocus value of each micrograph were evaluated by the superimposed the power spectra from all picked particles within the micrograph. The images used for the structural determination have their first zero approximately located within the range of 17-20 $Å^{-1}$. The self-common lines algorithm was used to yield the initial models for VLP/C-tag, VLP/Mab224 and VLP/Mab4, respectively (Crowther, R. A. *Philos Trans R Soc Lond B Biol Sci* 261:221-230 (1971)). The refinement on particle origin and orientation was carried out iteratively using polar Fourier transformation algorithm (PFT) (Baker, T. et al., *J. Struct. Biol.* 116:120-130 (1996)). Three-dimensional reconstructions were computed by combining a set of particles with the orientations evenly distributed in an icosahedral asymmetric unit, with the Fourier-Bessel algorithm while superimposing of 5-3-2 icosahedral symmetry. To examine the reliability of the three-dimensional reconstruction, the dataset was evenly divided into two parts and computed two three-dimensional reconstructions. The resolution was estimated using Fourier shell correlation (FSC) by assessing the agreement between these two reconstructions in the Fourier space; a coefficient value of 0.5 was used as the criteria to estimate the effective resolutions of VLP/C-tag, VLP/Mab224, and VLP/Mab4 at 17.5 Å, 18.5 Å, and 24 Å respectively.

The electron density map was displayed in the isosurface mode, which builds a surface barrier to contour the density about a certain threshold to provide the concise surface details on the density map. The contour level was chosen at the value corresponding to the 100% mass of the particle volume. The surface presentations of the cryo-EM density maps was prepared with the program Chimera (Pettersen, E. F. et al., *J Comput Chem.* 25:1605-1612 (2004)).

Fitting the Crystal Structure into Cryo-EM Density Maps

Manually fitting was carried out by translational and rotational movement of the PORF2 crystal structure into the cryo-EM density maps using program 0 (Jones, T. A. et al., *Acta crystallogr. Sect. A* 47:110-119 (1991)) To get the best fit, the coordinates of PORF2 subunit was treated as a rigid body. To optimize the fitting results, symmetry-related molecules were generated and judged by the crashes between subunits. The fitting was evaluated based on the cross correlation coefficient (cc value) between the cryo-EM density and the density computed from the fitted PORF2 coordinates. The fitting was considered as stable when the cc value reaching 80%. The figures on fitting were prepared using the program PyMOL (DeLano, W. L. *DeLano Scientific*, Palo Alto, Calif., USA (2002)) and the surface stereographic projection of the HEV VLP was prepared with the program RIVEM (Xiao, C. et al., *J Struct. Biol.* 158:181-186 (2007)).

Results

Binding of Antibody Mab224 Relies on the Presence of Residues 601-608 Protein

The binding of monoclonal antibody Mab224 to PORF2 was characterized with a Western Blot assay because no cell culture system is currently available to test the ORF2 escape mutants. A series of C-terminally truncated PORF2 proteins were separated using 10% SDS-PAGE under reducing condition, and blotted with Mab224 (FIG. 1A). Mab224 recognized PORF2-derived peptides containing regions of 112-660, 112-608, 112-602 and 112-601. In contrast, the peptides comprising residues 112-600, 112-596, and 112-589 were non-reactive with Mab224. These data suggest that residue Leu601 is critical for Mab224 binding with the PORF2 protein. The lower molecular weight bands detected by the Mab224 are degraded ORF2 proteins that contain the binding sequence of the Mab224.

Two-dimensional Electron Cryo-micrographs

On cryo-electron micrographs, both chimeric HEV particles and Fab-conjugated VLP complex had circular profiles with spiky densities extending from the surface (FIG. 1C). They appeared as empty particle and similar to the morphology we observed previously with the HEV native VLPs (Li, T.-C. et al., *J. Virol.* 79:12999-13006 (2005); Xing, L. et al., *Virology* 265:35-45 (1999)), indicating that RNA moiety is absence from these VLPs. The sizes of both VLPs were approximately 27 nm without taking into account the extra densities extending further from the surface of VLP/Mab224 (FIG. 1C, right).

Binding Footprints of the Antibodies

The cryo-EM structure of VLP/Mab224 was reconstructed from 615 images and displayed T=1 icosahedral symmetry with 60-subunits per particle. There are 30 dimeric protruding spikes located at each icosahedral two-fold axis (FIG. 14A). Sixty Fab fragments were observed around each VLP particle and jutted from the lateral sides of the P domain. The Fab density was measured as ~57 Å high from the surface of the spike. The density corresponding to Fab fragment was approximately equal in magnitude to that of the HEV VLP, indicating that most or all of the 60 binding sites had been occupied by a Fab molecule. Using the density map of HEV VLP (Xing, L. et al., *Virology* 265:35-45 (1999)), the density corresponding to VLP capsid was removed from the cryo-EM map, producing a Fab difference density map that was used to pinpoint the binding site of Mab224 antibody (footprint).

Figure 14:
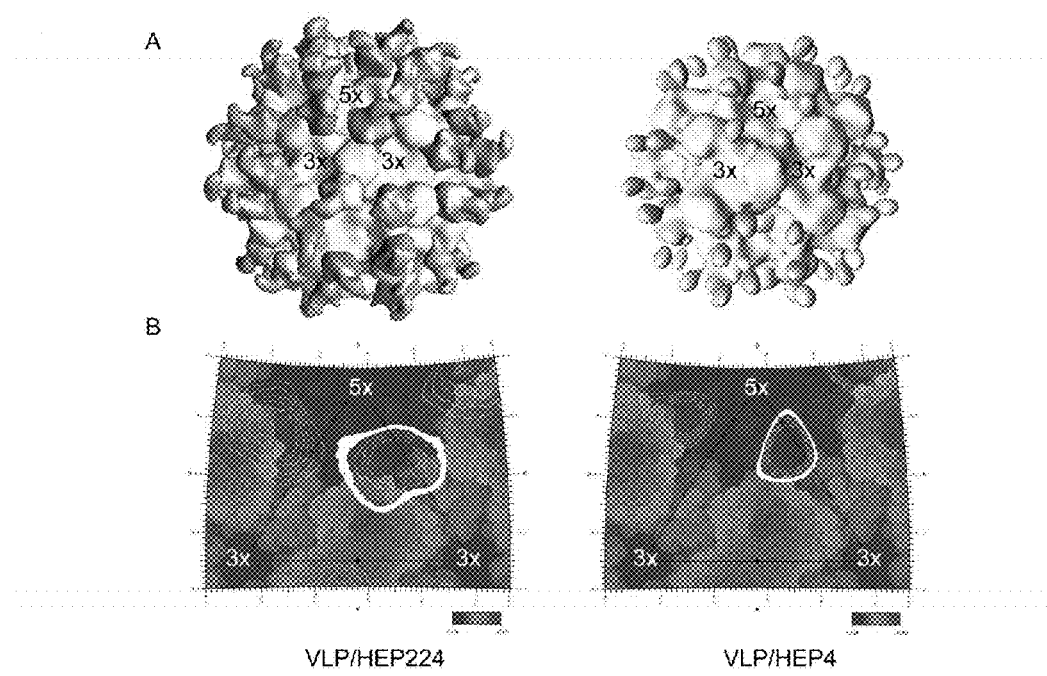
FIG. 14. The cryo-EM structure of HEV T=1 VLP in complexed with the Fab fragments. (A) Surface presentation of VLP/Mab224 (left) and that of VLP/Mab4 (right) viewed along one of the icosahedral twofold axis. One fivefold axis and two adjacent threefold axes are marked with corresponding number. In both reconstructions, sixty copies of Fab fragment attached to the later side of HEV VLP; however, the density of Mab4 Fab fragment appears weaker than that of Mab224 Fab fragment. (B) The viral surface is shown as a stereographic projection overlapped with line drawn an icosahedral asymmetric unit. The fivefold, threefold and twofold axis are marked with corresponding numbers. The Fab density is projected as white circles on the viral surface.

Meanwhile, we determined the structure of HEV VLP in complexed with a neutralizing antibody, Mab4 by combining 234 individual images. By in vitro immunoprecipitation, Mab4 is found to precipitate native HEV virion and the recombinant PORF2 peptide, but does not react with the peptides missing amino acids 597-607 (Schofield, D. J. et al., *Vaccine* 22:257-267 (2003)). The three-dimensional reconstruction of VLP/Mab4 complex showed sixty copies of Fab fragment per HEV VLP, indicating one Fab fragment per PORF2 subunit. Unlike the complex of Mab224, the density corresponding to Mab4 was about one third in magnitude to that of the capsid (FIG. 14A), suggesting that only 30-40% of the binding sites were occupied by the Fab fragments. Moreover, the Fab difference map indiates that the Fab fragment of Mab4 appeared to contact with those residues at the spike stem region, as a result, the density above the spike surface represented only the Fc domain (FIG. 14A). Both Mab224 Fab fragment and Mab4 Fab fragment extends along the long axis of protruding P domain and appeared no steric hindrance with the neighboring Fab molecules at the regions around five-fold axis and that around three-fold axes. The density profile of bound Fab fragments appeared 90° different at radius corresponding to the spike surface (135 Å). The long axis of Mab224 extends toward neighboring spike, while the long axis of Mab4 pointed to the fivefold axis (FIG. 14B).

Figure 15:
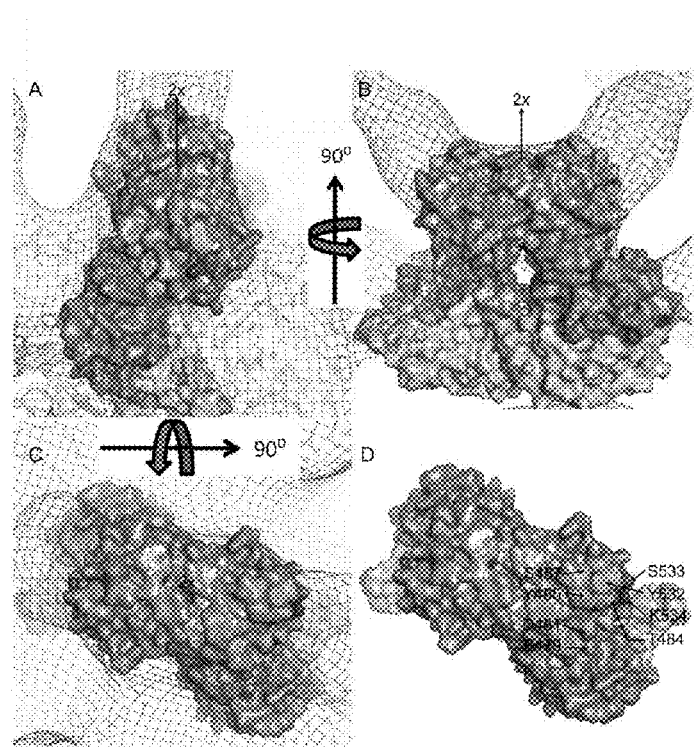
FIG. 15. The binding site of Mab224 antibody. (A) The cryo-EM density map of VLP/Mab224 was fitted with the crystal structure of PORF2 and viewed along a bound Fab molecule. One PORF2 dimer is presented as solid surface and the neighboring dimers are drawn as ribbon mode. (B) The side view of a PORF2 dimer fitted into the cryo-EM density map. (C) A PORF2 dimer viewed along the twofold axis overlapped with the cryo-EM density map. (D) The top view of a PORF2 dimer viewed along the twofold axis. The amino acids in PORF2 responsible for binding to Mab224 are labeled. The PORF2 dimer is presented as solid surface.

To further analysis the binding interface of Fab and HEV VLP, we docked the crystal structure of genotype-1 PORF2 into the cryo-EM density map of VLP/Mab224. The crystal structure of genotype-1 PORF2 was composed of three domains and in good agreement with those of genotype-3 and genotype-4 PORF2 (PDB accession number 2ZTN and 3HAG, respectively) (Xing, manuscript in preparation). The coordinates fitted very well with the cryo-EM density map without any adjustment. The Fab fragment of Mab224 interacted with the residues at side of the ORF2 spike rather than those residues on the plateau surface of the spike (FIG. 15A). The contact footprint does not overlap with the dimeric interface of the PORF2 spike. As we expected, Mab224 is a conformational antibody, whose binding site covers three surface loops: the AB loop (470-493), the CD loop (539-569) and the EF loop (581-595) (FIG. 15B). The residues E479, D481, T484, Y485, S487 from the AB loop and residues Y532, S533, and K534 from the CD loop were in close contact with the Fab molecule.

Structure of HEV Chimeric VLP

The PORF2 fusion protein was constructed to incorporate a B-cell tag of 11 amino acids to the C-terminus of PORF2 (FIG. 1c), from which the chimeric HEV VLP (VLP/C-tag) was assembled. A total of 782 images of individual particles were used to reconstruct the final three-dimensional model of VLP/C-tag. In agreement with the previously published cryo-EM structure of VLP, the surfaces of VLP/C-tag can also be divided into two distinct layers, an icosahedral shell and a protruding spike (FIG. 16A). The spike projects outward from the icosahedral shell and composed of a PORF2 dimer. The distance between each two-fold axis was ~76 Å, measured between the top surfaces of two adjacent P domains, which is consistent with the results measured in the VLP obtained from Tn5 insect cells and that from Sf9 insect cells. No significant RNA density was found within the chimeric VLP/C-tag.

The crystal structure fit very well with the density map of VLP/C-tag (FIG. 16B), indicating that the C-terminal insertion of 11 amino acids inhibits neither the dimer-dimer interactions nor the formation of T=1 VLP. When superimposing the density maps at the contour covering 100% protein mass, we found that the radii of the S domain were roughly the same in both VLP/C-tag and VLP/Mab224 maps and the height of protruding spike appeared similar. No significant density difference was observed on the surface of spike plateau from the docking (FIG. 17), suggesting that the inserted B-cell tag is flexible and less ordered. However, there appeared extra density at lateral side of the spike and underneath the Mab224 binding site (FIG. 17A), which may corresponding to the inserted peptides.

Discussion

The HEV T=1 VLP is a recombinant virus-like particle that induces anti-HEV antibody in non-human primates (Li, T.-C. et al., *Vaccine* 22:370-377 (2004)). It can also be used as antigen carrier to deliver foreign epitopes through oral administration (Niikura, M. et al., *Virology* 293:273-280 (2002)) and DNA vaccines (Takamura, S. et al., *Gene Ther* 11:628-635 (2004)). Therefore, the structural analysis on antibody recognition sites is essential for developing VLP based antiviral strategies. For this purpose, we determined the structure of HEV VLP in complexed with antibody Mab224 (VLP/Mab224) and antibody Mab4 (VLP/Mab4) as well as the structure of chimeric HEV VLP carrying a B-cell tag at PORF2 C-terminus (VLP/C-tag). The docking of PORF2 crystal structure provides us the spatial information on HEV antigenic domain and structural guidance to better design the insertion of foreign epitopes.

Structure of the Neutralization Epitopes

Antigenic properties and neutralization mechanism in HEV are difficult to be characterized due to the fact of lacking adequate replication systems in cell cultures. Therefore, our understanding of HEV immunology are mainly based on the studies using recombinant proteins expressed in *Escherichia coli* (*E. coli*) and recombinant proteins or HEV-VLPs in insect cells. All the evidences indicated that the C-terminal region of PORF2 participates in the immune response of HEV and suggested that the neutralization epitope of HEV is conformational. Later, the minimum peptide required to induce HEV neutralizing antibody was identified to 148 residues of PORF2, from amino acids 459-607 (Zhou, Y. H. et al., *Vaccine* 23:3157-3165 (2005)). This peptide region coincides with the P-domain revealed in the crystal structures of PORF2. Our cryo-EM structures revealed that the Fab fragment attached entirely with the spikes, thus experimentally demonstrated that the P domain carries primarily the HEV antigenicity. Mab4 is a chimpanzee antibodies against the ORF2 protein isolated against with phage display from a coda library of chimpanzee (Schofield, D. J. et al., *J Virol* 74:5548-5555 (2000)). It binds to native HEV virion and the recombinant PORF2 peptides containing amino acids 597-607 (Schofield, D. J. et al., *Vaccine* 22:257-267 (2003)). We did fitting with the structure of HEV/Mab4, however, the density of Mab4 is too weak to provide conclusive binding orientation of the Mab4, although the density corresponding to the Fab fragment did cover the location of amino acid 606 (data not shown). It is not clear why Mab224 appeared non-reactive with the peptides lacking amino acids 601-608 on Western Blot, however, the binding site of Mab224 is consistent with the critical antigenic residues determined earlier with mutagenesis. It is found that the point mutations of charged residues E479, K534 to alanine as well as the hydrophobic amino acids Y485 and I529 to alanine would selectively abrogate the reactivity with the neutralizing antibodies (Li, S. et al., *PLos Pathog.* 5:e1000537 (2009)). Another set of mutants suggested the same region as antibody recognition residues spreading over the loops of AB, CD and EF (Yamashita, T. et al., *Proc Natl Acad Sci USA* 106:12986-12991 (2009)). This neutralization site is partially overlapped with the receptor binding site, where the bound antibody create spatial hindrance to prevent HEV VLP from attachment to the cell surface (Yamashita, T. et al., *Proc Natl Acad Sci USA* 106: 12986-12991 (2009)). The antibodies used in both experiments are with neutralizing activity; therefore, the monoclonal antibody Mab224 is most likely a neutralizing antibody because its binding site is part of HEV dominant neutralization surface.

Insertion Sites for Foreign Epitopes

Figure 16:
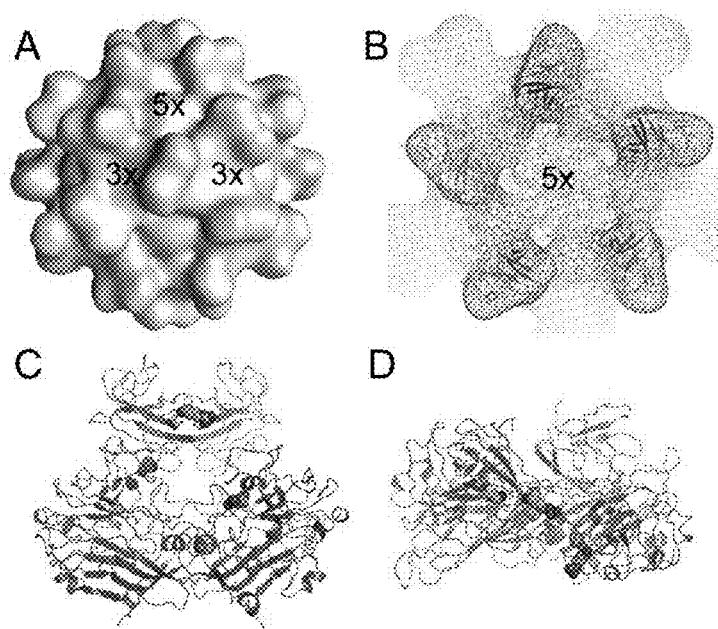
FIG. 16. The structure of the chimeric HEV VLP carrying a B-cell tag. (A) Surface presentation of VLP/C-tag viewed along an icosahedral twofold axis. (B) The cryo-EM density map of VLP/C-tag (mesh) was fitted with the crystal structure of PORF2 decamer (Ribbon). (C) Ribbon representation of PORF2 dimer. The four selected internal insertion sites are marked as sphere mode representing the element. (D) The top view of the PORF2 dimer showing the location of the internal insertion sites.
Figure 17:
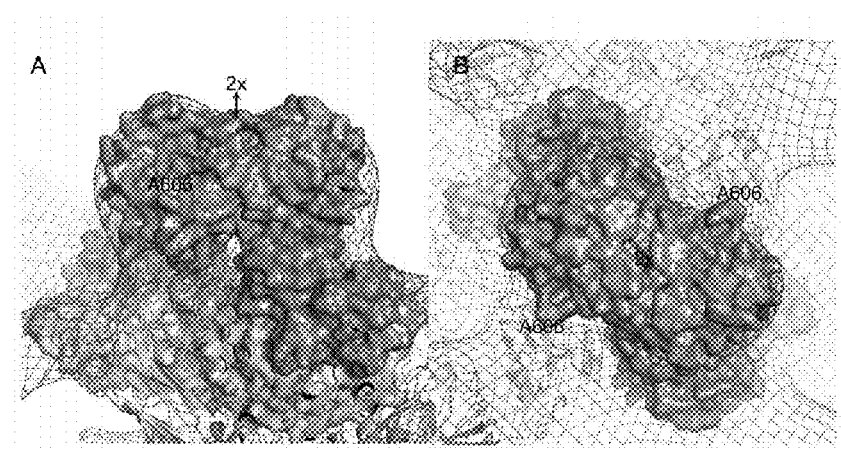
FIG. 17. Location of the C-terminal insertion relative to the Mab224 binding site. The side view (A) and the top view (B) of the fitted PORF2 dimer (surface presentation) overlapped the cryo-EM density map of VLP/C-tag (mesh). The C-terminal residue A606 is marked. The ribbon pres with their respective topology diagrams (Right). The β-strands are labeled from A" to F", following the nomenclature of SMSV.

Virus-like particles (VLPs) are one of the robust cargoes to carry simultaneously small molecules, peptide antigenic epitopes, as well as DNA vaccines of heterogonous sources in targeting other diseases because they are highly organized capsules that mimic the overall structure of virus particles. This approach relies on excellent structural information of VLPs that allows rational design on where the foreign epitopes are conjugated. Six insertion sites were previously selected on PORF2 without knowing the crystal structure. They are the N- and the C-termini and four internal sites. The internal sites are after residues A179, R366, A507, and R542. The fusion proteins carrying insertion at sites A179 and R336 failed completely in VLPs production and those carrying insertion at A507 and R542 greatly reduced VLP production without affecting peptide expression (Niikura, M. et al., *Virology* 293:273-280 (2002)). The crystal structure revealed that these internal insertions are at the wrong spatial positions. The residue A179 is located in the S1 domain in the middle of α-helix while the completeness of the α1 helix is necessary for the integrity of S1 domain thus the interaction with its twofold related neighboring subunit (FIG. 16C). R366 is located in the S2 domain and favors electrostatic interaction with the residue E386 from its threefold related neighboring subunit (FIG. 16D). Although located at P domains, the side chain of R542 is within the dimeric interface and guides the hydrophobic interaction of two monomers (FIG. 16D). Insertion after R542 may misalign the orientation two P domains that weaken the dimeric interaction of PORF2 protein. The role of residue A507 in the P-domain is to maintain the P domain orientation by fixing the angle to the long proline-rich hinge (FIG. 16C). None of the four residues are exposed on the surface of VLP, although some of them are at the surface of individual PORF2 subunits (FIG. 16). Therefore, insertion of a foreign sequence at these sites induces no interference to the expression of individual protein, but does bring in hindrance to the assembly of HEV VLPs. The crystal structure revealed that the C-terminus is exposed on the surface of VLP and N-terminal is pointing toward the VLP center. Therefore, insertion at these two sites does not inhibit the assembly of VLP; however, the C-terminus is more suitable to tether bulky foreign antigenic sequences, as it exposed on the VLP outer surface (FIG. 17).

The cryo-EM structure of the chimeric HEV VLP/C-tag suggested the location of the B-cell tag at the lateral site of the spike, not far from the residue A606 (C-terminal end) (FIG. 17A). This density saturated beneath the binding site of Mab224, but overlapped with the potential binding site of Mab4. As a result, the insertion of B-cell 11 amino acids may open partially the HEV antigenic site to host immune system. This explains why the infected mouse can develop antibodies against both HEV and the foreign epitope after oral administrated with the chimeric VLP/C-tag.

In conclusion, insertion of foreign epitope on the C-terminus of PORF2 does not intervene with the accessibility of HEV antigenic domain. Therefore, the chimeric HEV VLP is able to induce antibodies against both HEV and the target disease. As recombinant ORF2 VLP is currently under phase II clinic vaccine trial (26), the T=1 HEV VLP will play an important role in oral delivery.

Example 4

Structural Basis for the RNA-Dependent Assembly Pathway of Hepatitis E Virion-Sized Particles Hepatitis E virus (HEV) induces acute liver failure in human with high fatality rate in pregnant women. There is a need for anti-HEV research to understand the assembly process of HEV native capsid. Here, we produced a large virion-sized and a small T=1 capsid by expressing the HEV capsid protein in insect cells with and without the N-terminal 111 residues, respectively, for comparative structural analysis. The virion-sized capsid demonstrates a T=3 icosahedral lattice and contains RNA fragment in contrast to the RNA-free T=1 capsid. However, both capsids shared common decameric organization. The in vitro assembly further demonstrated that HEV capsid protein had intrinsic ability to form decameric intermediate. Our data suggest that RNA-binding is the extrinsic factor essential for the assembly of HEV native capsids.

Hepatitis E virus (HEV), the causative agent of acute hepatitis in human, is primarily transmitted through contaminated water and generally results in epidemic outbreaks in many developing countries. Sporadic cases have also been reported between outbreaks in HEV-endemic regions as well as in non-endemic areas and these cases are transmitted through zoonotic route. The overall mortality rates of HEV during outbreaks range from 1 to 15% in general and the highest mortality occurs in pregnant women, with fatality rates of up to 30% (Naik, S. R. et al., *Bull World Health Organ* 70, 597-604 (1992)).

HEV consists of a non-enveloped icosahedral capsid and a single-stranded, positive-strand RNA genome of ~7.2 kb that encodes three open reading frames (ORFs) (Tam, A. W. et al., *Virology* 185, 120-131 (1991)). The capsid protein, encoded by the ORF2, is composed of 660 amino acids and responsible for most capsid-related functions, such as virion assembly, host interaction, and immunogenicity. Like other hepatitis viruses, HEV is unable to propagate in currently available cell culture system and the research of HEV relies largely on the recombinant HEV capsid proteins (Schofield, D. J. et al., *Vaccine* 22, 257-267 (2003); Li, T.-C. et al., *Vaccine* 22, 370-377 (2004); Purdy, M. A. et al., *J Med Virol* 41, 90-94 (1993); Riddell, M. A. et al., *J Virol* 74, 8011-8017 (2000)). Virus-like particle (VLP) was obtained when the truncated HEV capsid protein was expressed in insect Tn5 cells with deletion of 52 residues from the C-terminus and 111 residues from the N-terminus (PORF2) (Li, T. C. et al., *J Virol* 71, 7207-7213 (1997)). Our previous structural analysis of this HEV-VLP by cryo-electron microscopy (cryo-EM) provided a basic understanding of the quaternary arrangement of PORF2, where the reconstructed VLP displayed a T=1 icosahedral particle composed of 60 copies of PORF2 (Xing, L. et al., *Virology* 265, 35-45 (1999)). The essential element of PORF2 protein for T=1 VLP assembly includes amino acids 125-600 (Li, T.-C. et al., *J. Virol.* 79, 12999-13006 (2005)). Recently, the structural information was further refined by the crystal structures of genotype-3 T=1 VLP (Yamashita, T. et al., *Proc Natl Acad Sci USA* 106, 12986-12991 (2009)) and genotype-4 T=1 VLP (Guu, T. et al., *Proc Natl Acad Sci USA* 106, 12992-12997 (2009)), which revealed the tertiary structure of PORF2 to the level of amino acids. However, the T=1 VLPs used in these experiments were much smaller than that of the native virion, which has a diameter of 320-340 Å, as determined by immuno-EM (Balayan, M. et al., *Intervirology* 20, 23-31 (1983)). There is still a need to investigate the assembly pathway of HEV capsid.

We previously hypothesized that HEV virion could be made of 180 copies of the capsid protein (Xing, L. et al., *Virology* 265, 35-45 (1999)). To test this hypothesis, we screened for HEV genotype expression and successfully produced a virion-sized VLP from the HEV genotype-3 ORF2 protein after deleting 52 residues from C-terminus. This VLP allowed us to investigate the molecular interactions that govern HEV virion assembly.

Experimental Procedures
Production of HEV-VLPs and in Vitro Disassembly and Reassembly HEV-VLPs were produced and purified according to the protocol described previously (Li, T. C. et al., *J Virol* 71, 7207-7213 (1997)). Briefly, the recombinant baculovirus is constructed to encode genotype-3 HEV-ORF2 protein from residue 14 to 660 (Li et al., manuscript in preparation). Tn5 cells were infected with recombinant baculovirus at an M.O.I of five and cultured for 6 days. The supernatant was collected and the VLP was purified by multiple ultracentrifugations, followed by separation on a CsCl density gradient. The final pellet was resuspended in 10 mM potassium-[2-(N-morpholino)ethanesulfonic acid] (MES) buffer, pH 6.2. A homemade dialysis device was used in the disassembly and reassembly experiments, because it allowed dialysis with a small amount of sample (20-40 µl). Purified VLP was disrupted by dialysis against buffer containing EDTA (10 mM) and DTT (20 mM) at different pHs. After VLP dissociation, 150 mM NaCl in Tris-HCl buffer (pH 7.5) was added, and sample was examined under the electron microscope after one-hour incubation in the presence of the divalent ion $Ca^{2-}$ (20 mM).

Scanning Transmission Electron Microscopy Analysis of HEV-VLPs

Scanning TEM was performed at the Brookhaven National Laboratory STEM facility, with TMV as an internal control. The mixture of VLP and TMV was quickly frozen in liquid nitrogen, and then maintained at −150° C. during data collection to eliminate contamination and reduce mass loss. The specimen was scanned by a 40 keg electron beam of 0.25 nm in size, and images were collected with a preamp gain of 10 for both large and small angle detectors (Wall, J. S. et al., *Methods Cell Biol.* 53, 139-164 (1998)). The image was recorded with a pixel size of 10 Å and was analyzed with the PCMass29 program (Brookhaven National Lab http://www-.biology.bnl.gov/stem). After normalizing the background, the mass of the VLPs was selected with the MSV shell model provided by the program. Mass measurements for TMV and HEV-VLPs were always performed from the same image. The HEV-VLP mass was measured in MDa (mass per particle) and the TMV mass was measured in KDa/Å (mass per unit length) (Wall, J. S. and Simon, M. N., *Methods Mol Biol.* 148, 589-601 (2001)).

Cryo-electron Microscopic Structure Determination of HEV T=3 VLP

Figure 26:
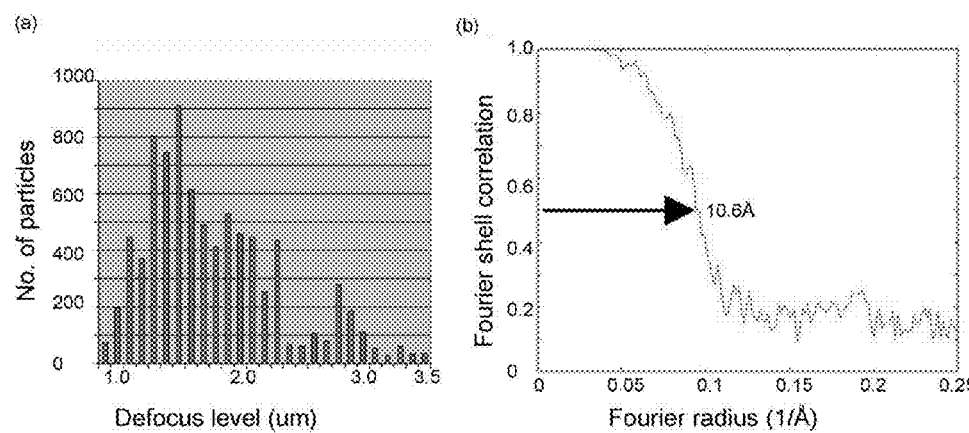
FIG. 26. Technical data for cryo-EM reconstruction of a large HEV-VLP. (a) Distribution of cryo-EM with a defocus level of 0.7-3.5 µm. (b) Fourier shell correlation indicating that the resolution of the final density map is 10.6 Å (cutoff of 0.5).

The collection of cryo-EM data for image reconstruction was performed on a JEOL JEM-2100F TEM operating at 200 kV according to the procedure described in detail previously (Xing, L. et al., *Virology* 265, 35-45 (1999)). Briefly, a 3 µl solution containing E330K capsid or reassembled ORF2 complex was placed on holey carbon film-coated copper grids, and then quickly plunged into liquid ethane after the removal of excess solution. The VLPs were embedded into a thin layer of vitrified ice and transferred into the EM using a Gatan 636 cryo-transferring system. The specimen was observed under 50,000× magnification and the area of interest was recorded on a TVIPS CCD camera (TemCam-F415). The micrographs were recorded with a pixel size of 2.0 Å at a specimen space and defocus level of 0.7-3.5 Å (FIG. 26a). Digital images with no stigmatism or drift were selected for later image processing. Images of individual HEV T=3 VLP were then boxed out and processed with an established software package for icosahedral particles (Baker, T. S., and Cheng, R. H. (1996) *J Struct Riot* 116, 120-130; Ji, Y. et al., *J Struct Biol* 154, 1-19 (2006)). In total, 7720 individual images were included in the process, and their defocus levels were distributed mainly within 1.0-2.5 Å.

To correct CTF (contrast transfer function) effect, we applied phase-flipping on each image with an in-house program. The density maps were initially reconstructed by combining 1812 individual images to an effective resolution of 14 Å. Next, amplitude correction was applied during map reconstruction while new data was added. The final density map was reconstructed by combining images of 4348 individual particles, and the final resolution was assessed as 10.6 Å by Fourier Shell Correlation with a cutoff of 0.5 (FIG. 26b).

Docking of the T=1 crystal structure into the T=3 cryo-EM density map was first done manually with the program O (Jones, T. A. et al., *Acta crystallogr. Sect. A* 47, 110-119 (1991)), and then refined with the Situs software package (Chacon, P. and Wriggers, W., *J Mol Biol* 317, 375-384 (2002)). The PORF2 monomer was treated as a rigid body during the initial fitting and refinement processes.

X-ray Crystallographic Structure Determination of T=1 HEV-VLP

Crystallization of the VLPs was performed according to a previously described method (Wang, C. Y. et al., *Acta Crystallogr. Sect. F Struct. Biol. Cryst. Commun.* 64, 318-322 (2008)). Crystals were directly flash-frozen in liquid nitrogen and x-ray diffraction experiments were performed. All x-ray experiments of the HEV-VLP crystals were performed at SPrin-8 in Hyogo, Japan. Particle orientation in the unit cell was determined with a self-rotation function, (Blow, D. M. et al., *J Mol Biol* 8, 65-78 (1964)) and the particle position was determined by a translation search with the cryo-EM structure as the model. The asymmetric crystal unit contains one particle; as a result, 60-fold non-crystallographic symmetry (NCS) averaging was enforced. The cryo-EM structure (Xing, L. et al., *Virology* 265, 35-45 (1999)) was used to obtain the initial phases of Data I, and generated the envelope (mask) used for NCS averaging. The phases were refined by real space electron density averaging with icosahedral symmetry elements and solvent flattening. The resolution was gradually extended to 8.3 Å (R-factor=0.21, correlation coefficient [CC]=0.92). This structure was used for the phasing of Data II, and the phases were refined and extended to a 3.8-Å resolution (the overall R-factor and CC were 0.18 and 0.97, respectively).

Figure 27:
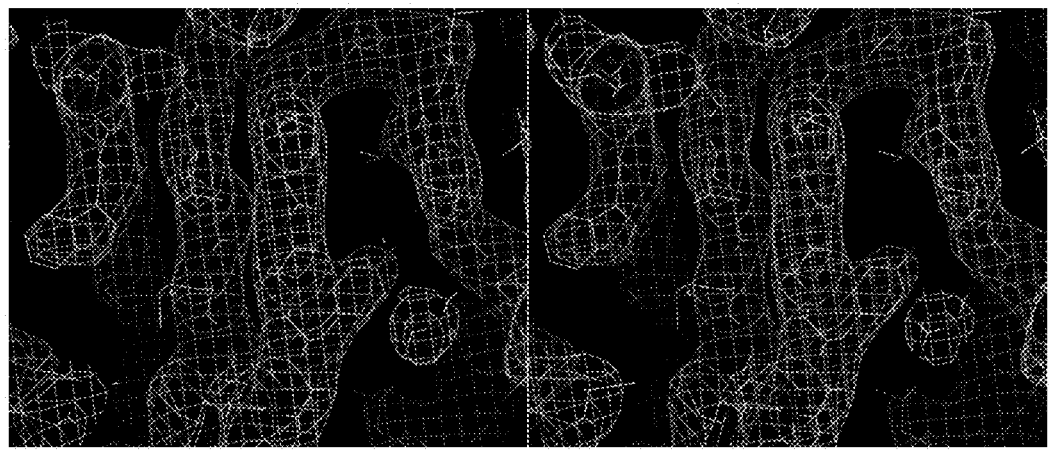
FIG. 27. Stereoimage of the T=1 VLP electron density map with modeled amino acid residues in the S1 domain.

Sixty icosahedrally related S-subunits were treated as identical and strict NCS constraints were applied during refinement. The data with resolution range of 20-3.8 Å was used in the refinement (Table 2 and FIG. 27). Further positional and B-factor refinement, followed by manual revision of the mode, resulted in an R-factor of 0.242 ($R_{Free}$=0.245) with reasonable stereochemistry (root mean square [rms] deviations in bond lengths and bond angles were 0.010 Å and 1.68°, respectively). Because of the high NCS, the R-factor and $R_{Free}$-factor were almost identical. After refinement, the stereochemistry of the structure was checked with Procheck (Laskowski, R. A. et al., *J Biomol NMR* 8, 477-486 (1996)): 98.1% of the nonglycine residues were within the most favored and the additional allowed regions of the Ramachandran plot, and none of the residues were in the additional regions. Atomic structure representations were generated using MolScript (Kraulis, P., *J Appl. Crystall.* 24, 946-950 (1991)) and Raser3D (Merritt, E. A. and Murphy, M. E. P., *Acta Crystall. Sec D* 50, 869-873 (1994)).

Results

Scanning Transmission Electron Microscopy (STEM)

Figure 18:
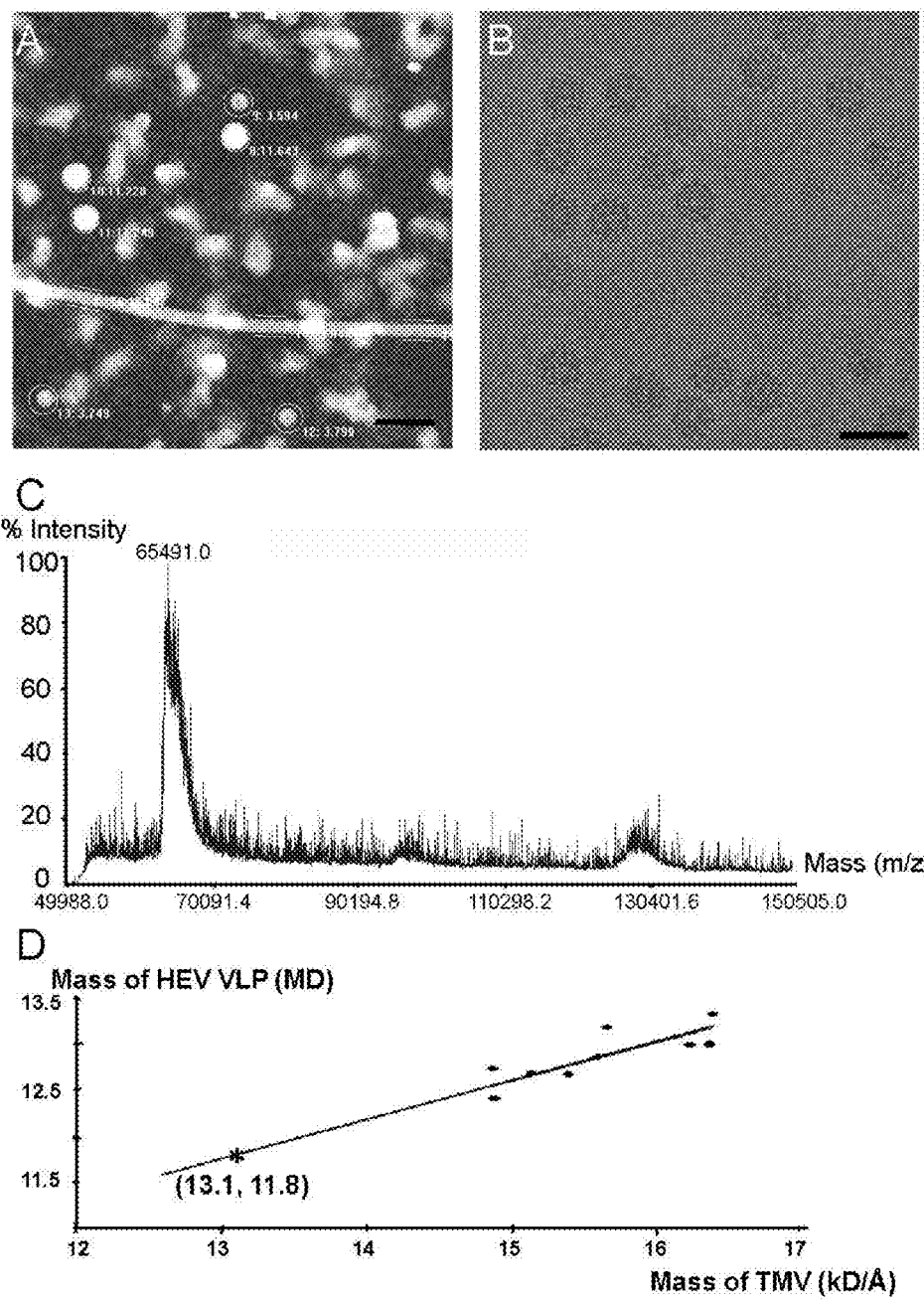

The virion-sized HEV-VLP was recovered when the genotype-3 ORF2 sequence was expressed in insect cells. This VLP projected as spherical image with a diameter of ~40 nm, larger than the T=1 VLP (27 nm in diameter) (FIG. 18a). In cryo-electron micrographs, the images of HEV-VLP are decorated with spike-like features and are homogenous in contrast (FIG. 18b).

To determine the composition of the large HEV-VLP, we performed mass measurements by using STEM, a technique measures the amount of electrons scattered from the objects, such as VLPs, on an EM grid. A mixture of purified large and small HEV-VLPs was freeze-dried onto EM grids for STEM mass measurement. Tobacco mosaic virus (TMV) with a known mass-to-length ratio was used as an internal standard. The HEV-VLPs appeared as spherical projections with white contrast on the dark-field STEM images (FIG. 18a). White cloud-like objects were present in the background, which might be the broken VLPs during sample preservation. The mean mass of large VLP and TMV in the images was measured to generate a plot of the mean TMV mass per unit length versus mean VLP mass per particle (FIG. 18a). A first-order fit was calculated and the mass of the large HEV-VLP was determined to be 11.8 MDa (FIG. 18d). The mass of the genotype-3 ORF2 protein, which was recovered from the large VLP, was measured as 65.5 KDa by mass-spectrometry (FIG. 18c). Therefore, the HEV large VLP contains 180 copies of ORF2 proteins, suggesting that the large HEV-VLP is a T=3 icosahedral particle (T=3 VLP).

Three-dimensional Reconstruction of the HEV Virion-sized Particle

Figure 19:
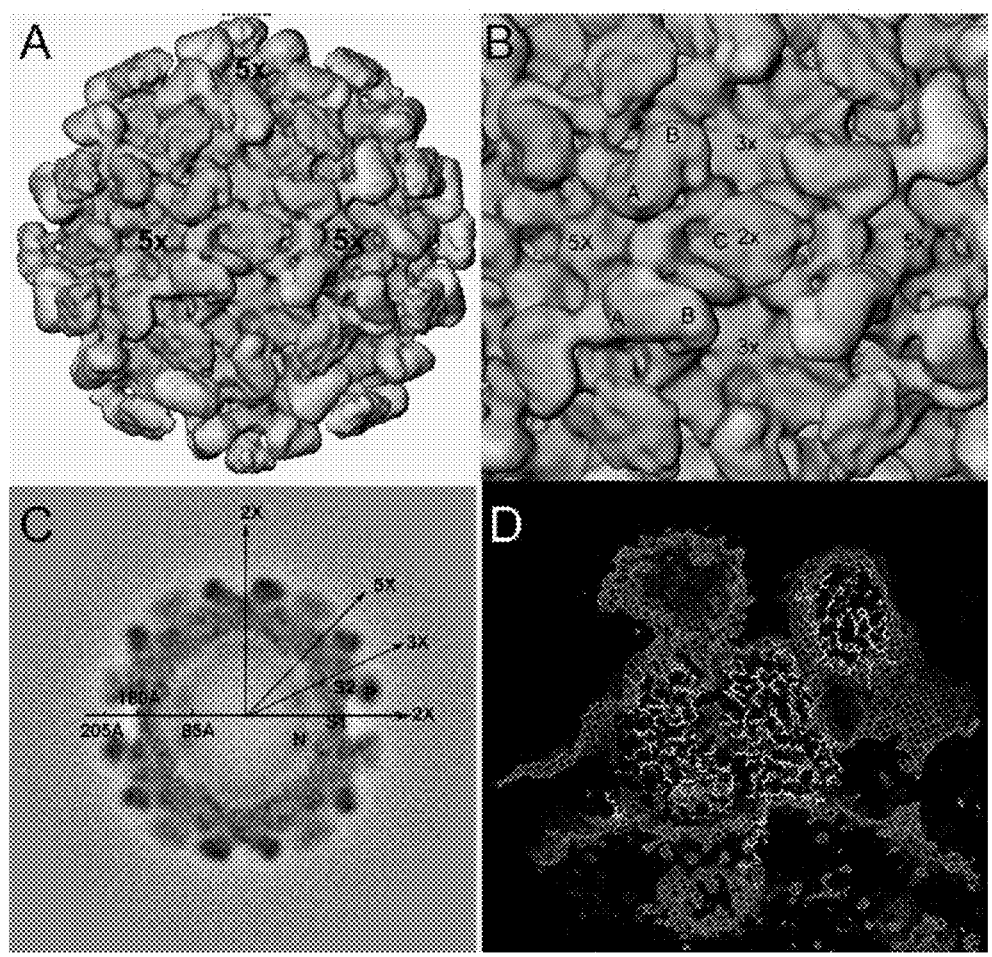

The cryo-EM structure of the large HEV-VLP revealed 90 protruding spikes on a complete icosahedral shell (FIG. 19a), which is consistent with the T=3 icosahedral symmetry and the results of the STEM mass measurements. The VLP had an overall diameter of 410 Å and a central cavity of 170 Å in radius as measured from the three-dimensional density map (FIG. 19c). The single-layer capsid contained 180 copies of ORF2 protein, which were grouped into three unique monomers according to their geometric environments. While monomers A and B formed dimeric spikes (A-B dimers) around each of the fivefold axes, two 2-fold related C monomers formed a spike (C-C dimer) at each of the icosahedral twofold axes (FIG. 19b). The surface lattices of ORF2 proteins in large HEV T=3 VLP was similar to the capsid arrangement of caliciviruses. Compared to the A-B dimer, the morphology of the HEV C-C dimer was less well-defined, perhaps due to flexibility in the angle of protruding domain toward icosahedral shell.

The density map of the T=3 VLP displayed four discrete domains, designated from the outside inward as P, S2, S1, and N, on a section 52 Å from the equatorial plane (FIG. 19c). The density profile of the P, S2, and S1 domains displayed less variation from that observed in T=1 HEV-VLP and the docking of the crystal structure of the T=1 PORF2 protein to the density map of T=3 HEV-VLP showed a very good agreement between the two structures (FIG. 19d). The docking positioned N-terminal tail of the PORF2 protein at the capsid inner surface aligned well with the density linker in T=3 VLP (FIG. 19d). The linker density served as a tag to connect the N domain with the icosahedral capsid, indicating the location of the N-terminal 111 amino acids of the ORF2 protein in T=3 HEV-VLP.

Crystal Structure of the Genotype-1 T=1 HEV-VLP

Figure 20:
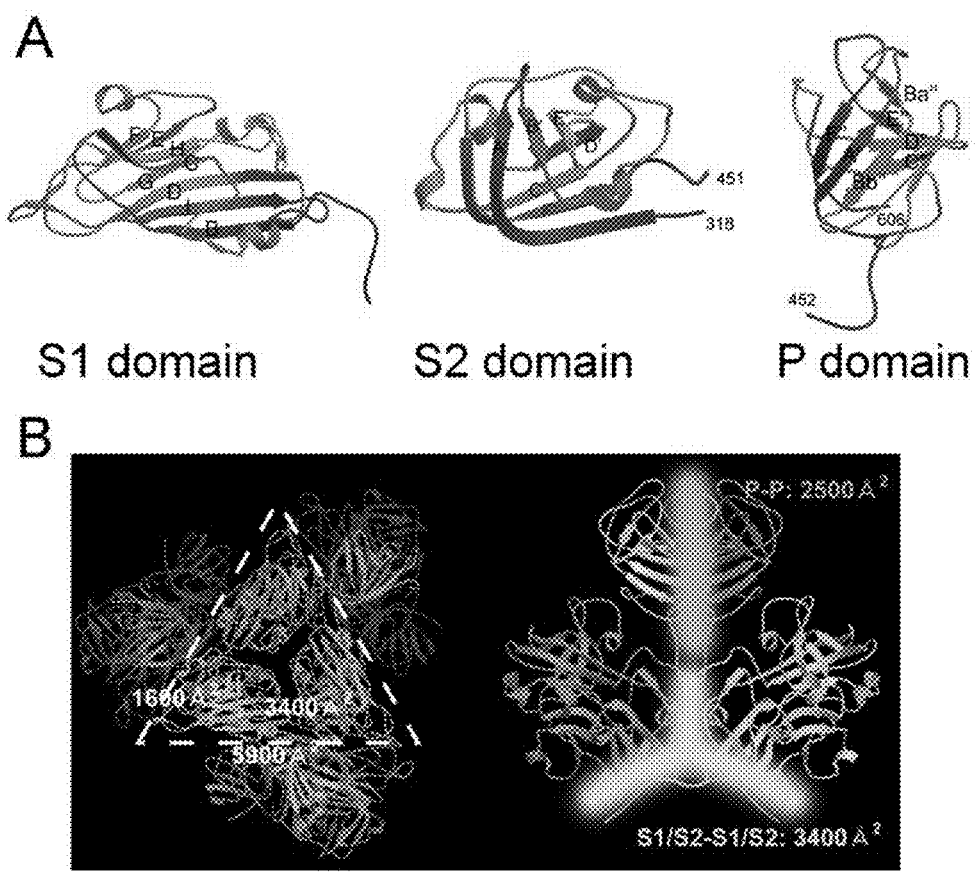
Figure 25:
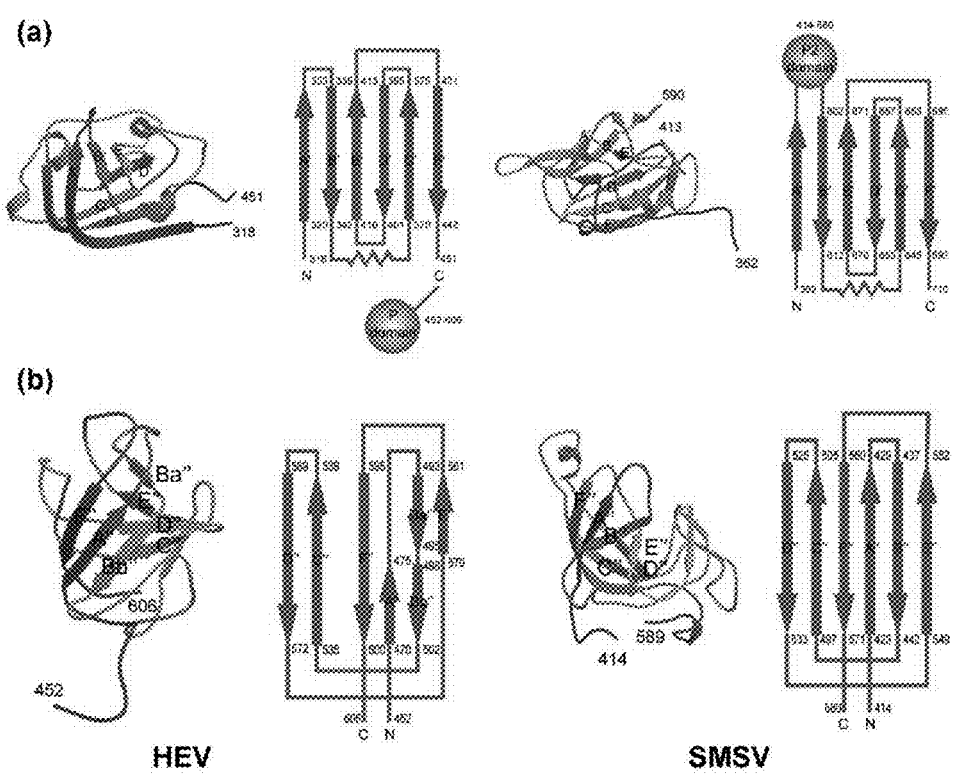

The crystal structure of the truncated genotype-1 capsid protein (PORF2, containing residues 112-608) can be separated into three domains, S1, S2, and P, with a less resolved region covering residues 555-560. The S1 domain formed by residues 118-317 folds into a classical eight-stranded β-barrel with a jelly roll motif (FIG. 20a), as observed in many T=3 viral capsid proteins (Rossmann, M. G. and Johnson, J. E., *Ann Rev Biochem* 58, 533-573 (1989); Harrison, S. C., *Curr Opin Struct Biol* 11, 195-199 (2001)). Uniquely, three additional short α-helices were observed in the S1 domain between strands E and F and strands G and H. The capsid shell was mainly stabilized by inter-subunit interactions between the S1 domains. The folded S2 domain, consisting of residues 318-451, was a twisted antiparallel β-sheet with an α-helix between the B' and C' strands (FIG. 20a). The P domain, composed of residues 452-606, folded into a β-barrel composed of antiparallel β-sheets, F"A"Bb" and Ba"E"D"C" (FIG. 20a), and were connected with the S2 domain through a long proline-rich hinge (PTPSPAPSRP (SEQ ID NO:8) of residues 452-461) (FIG. 20a). Although both the S2 and P domains existed above the S1 domain, the protruding spikes in the HEV cryo-EM map contain only P domain density, which is a clear difference to those caliciviruses (FIG. 25). The PORF2 dimers have the largest buried surface area (BSA) between monomers (5,900 Å$^2$) mainly due to between P domains (FIG. 20b). The BSA is 3,400 Å$^2$ and 1600 Å$^2$ for the two adjacent PORF2 subunits around threefold axis and fivefold axis, respectively (FIG. 20b). Moreover, the BSA of third molecule around threefold axis (9,500 Å$^2$) is much wider than that around fivefold axis (4,700 ↑$^2$).

Figure 24:
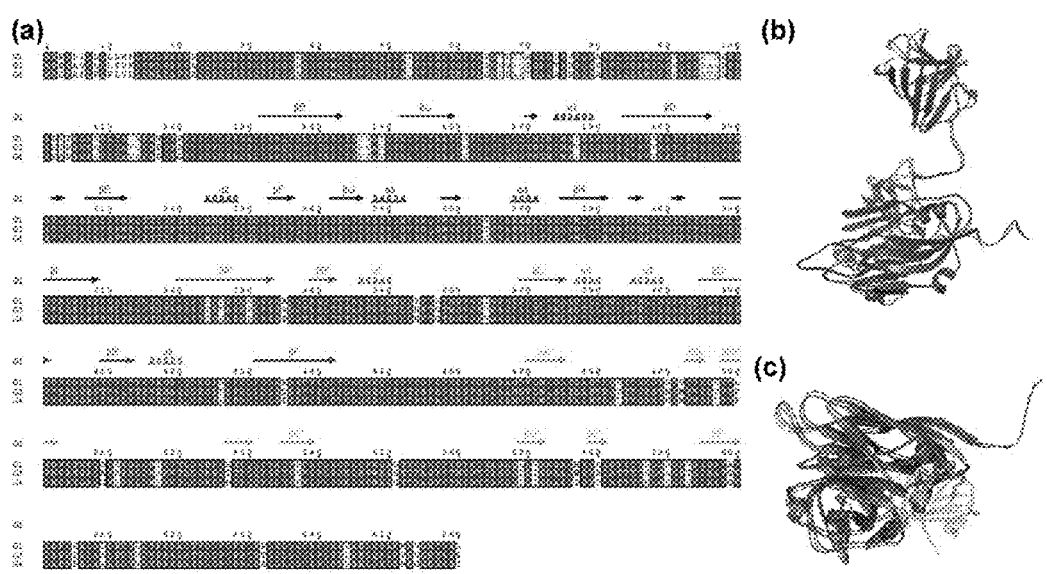

Sequence alignment of genotype-1 PORF2 with those of genotype-3 (Yamashita, T. et al., *Proc Natl Acad Sci USA* 106, 12986-12991 (2009)) and genotype-4 (Guu, T. et al., *Proc Natl Acad Sci USA* 106, 12992-12997 (2009)) revealed that the S1 domain is the most conserved region among HEV genotypes, while greater divergence was seen in the N-terminal region (FIG. 24a). Among the solved structures, genotype-3 appeared flexible at the N-terminal end and was 11 amino acids shorter than the others (FIG. 24b). Because amino acids 118-129 play an important role in bridging the N- to S1-domain in T=3 VLP and serve as docking registers, we used the crystal structure of genotype-1 to decipher the T=3 cryo-EM density map.

Consistent Interdimeric Interactions Between T=3 and T=1 HEV-VLPs

Figure 21:
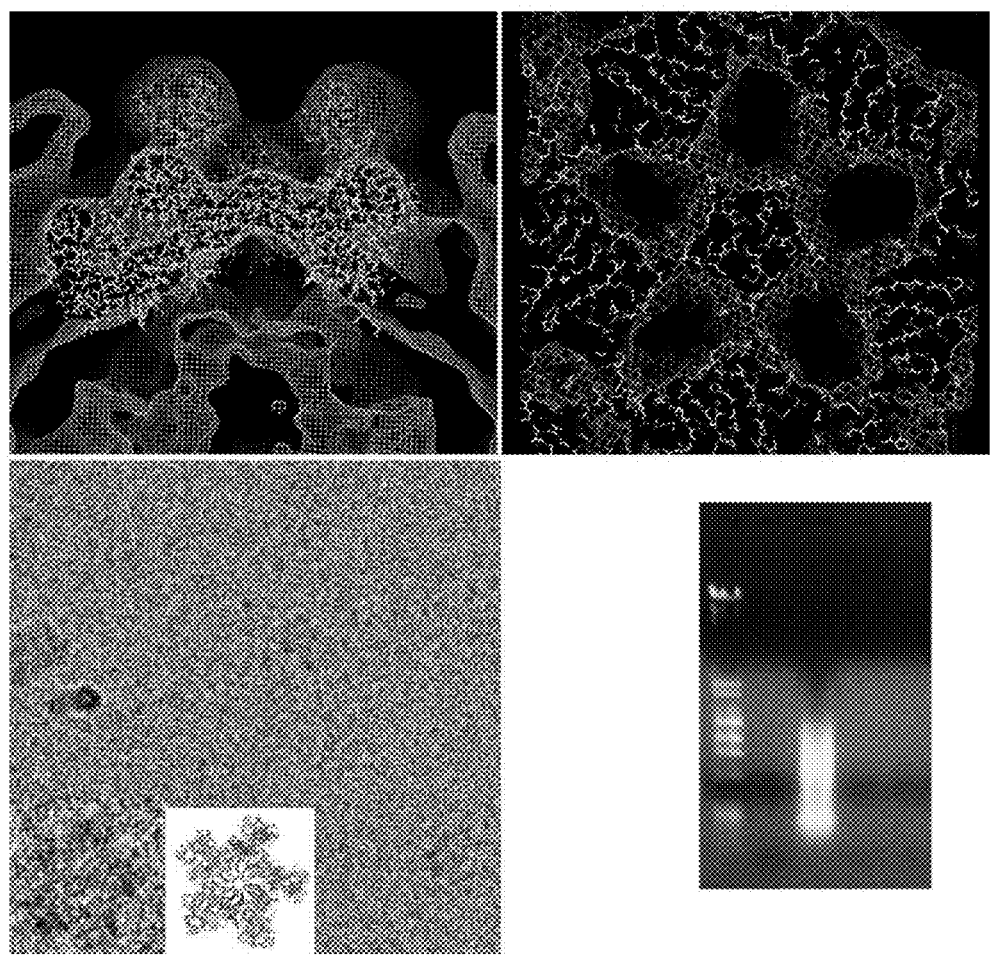
Figure 22:
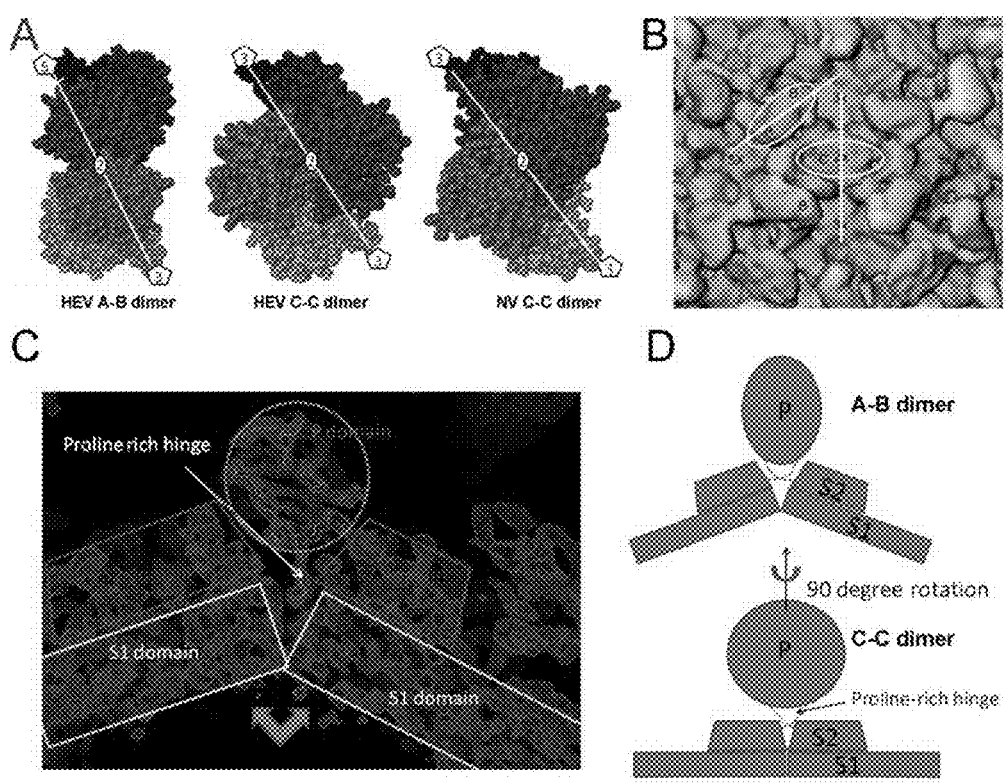

To understand the mechanism of ORF2 protein transition between T=1 and T=3 assemblies, we docked the T=1 decamer and hexamer into the T=3 cryo-EM density map. The decamer of T=1 VLP consisted of 10 adjacent PORF2 monomers corresponding to five dimers around a fivefold axis, while the T=1 hexamer corresponded to three adjacent dimers around a threefold axis. Unlike the hexamer, the coordinates of the PORF2 decamer fitted very well with the curvature of the T=3 density map at the fivefold vertex (FIG. 21a) and with the domain separation (FIG. 21b). The curvature of T=3 capsid at threefold axis did not agree with the coordinates of the PORF2 hexamer, as one of the dimers appeared sticking out of the cryo-EM density map (data not shown). Besides, the orientation of the P domain of the C-C dimer relative to its S2/S1 domains was 90° different to that of the A-B dimer (FIG. 22). This suggests that the molecular interactions among A-B dimers in the T=3 icosahedron are consistent with the dimer-dimer interactions in the T=1 icosahedral assembly, while the interaction between A-B dimer and C-C dimer is unique to the T=3 assembly.

In Vitro Reassembly of the ORF2 Protein

In order to understand the role of ORF2 decamer in T=3 VLP assembly, we analyzed the self-assembly process of HEV-VLP in vitro. A combination of chelating (EDTA) and reducing (DTT) agents was found to disassemble T=3 VLP in a high alkaline environment (pH 10) without denaturating the ORF2 protein (data not shown). Addition of 20 mM $CaCl_2$ into the disassembly solution led to the association of the ORF2 dimers into star-shaped complexes, and no refolded VLP was found (FIG. 21c). When we examined the star-shaped complexes, we found that the distance between two opposite vertices was ~18 nm, close to the diameter of TMV (FIG. 21c). This size was consistent with that measured from PORF2 decamers. Thus, the star-shaped complexes resembled not only the appearance but also the size of the ORF2 decamer (a pentamer of dimers). Although the overall BSA around threefold axis is larger than that around fivefold axis, we did not find any complexes that could fit with PORF2 hexamer.

The in vitro disassembly-and-reassembly suggested that other factors than ORF2 protein contribute to T=3 VLP assembly. Considering the electropositivity of the ORF2 N-terminal 111 amino acids, we performed nucleic acid extraction from both the T=3 and the T=1 VLPs. Electrophoresis results demonstrated the presence of nucleic acids in the T=3 extract, while the T=1 VLP extract was negative for nucleic acids (FIG. 21d). The extracted nucleic acids were sensitive to RNase treatment and resistant to DNase treatment, confirming that the T=3 VLP encapsidated RNA fragment during assembly while the T=1 VLP is free of RNA fragment. This result is consistent with the VLP profiles observed from the cryo-electron micrographs.

Discussion

Hepatitis E virus is a human pathogen that causes acute liver failure. Like other hepatitis viruses, HEV cannot be propagated with currently available cell culture techniques. The capsid protein of genotype-3 HEV can be expressed in insect cells as PORF2 protein, including amino acids 112-608 that self-assemble into T=1 VLP, and as ORF2 protein, including amino acids 1-608 that form T=3 VLP.

The crystal structures of PORF2 revealed three functional domains, S1, S2, and P, and the function of each domain constrained its sequence flexibility. The S1 domain formed an icosahedral shell that served as the base for arranging S2 and P domains; hence, the subunit surface should be highly conserved among genotypes. Sequence alignment agreed very well with this function, identifying the S1 domain as the most conserved region among HEV genotypes (Zhai, L. et al., Virus Res 120, 57-69 (2006)). The P domain serves as the putative binding site for both neutralizing antibody and cellular receptor (He, S. et al., J Gen Virol 89, 245-249 (2008)) and contains 19 divergent amino acids across four genotypes (FIG. 24a). Only nine of these amino acids were exposed at the surface of the P domain. Inspection of the binding footprint of antibodies on the cryo-EM density map indicated that only one amino acid was buried within the antibody-binding interface (Wang et al., manuscript in preparation). This explains why the HEV serotype is non-divergent despite sequence variation among HEV genotypes. The direct correlation between sequence variability and domain functionality may be necessary for the HEV capsid to carry multiple functions and to ensure error-free assembly. It also explains why the transition of HEV-VLP from the T=3 to T=1 lattice does not disturb its antigenicity, and why T=1 VLP can be disassembled and reassembled in vitro to carry foreign antigenic epitopes (Niikura, M. et al., Virology 293, 273-280 (2002)) or DNA plasmids (Takamura, S. et al., Gene Ther 11, 628-635 (2004)).

The T=3 HEV-VLP has a similar morphology to that of calicivirus; however, the crystal structures of PORF2 revealed a distinctive S2 domain arrangement, although the folding of the HEV S2 domain HEV is similar to the folding of the P1 domain in caliciviruses (FIG. 25). In HEV, the P domain is located at the C-terminal end of the S2 domain, while the P2 domain of caliciviruses is inserted into the P1 domain at the region between the A' and B' strands (Chen, R. et al., Proc Natl Acad Sci USA 103, 8048-8053 (2006); Prasad, B. V. V. et al., Science 286, 287-290 (1999)). Furthermore, the S2 domain of HEV interacts strongly with the S1 domain and connects to the P domain via a long proline-rich hinge, while the P1 domain in caliciviruses is a subdomain of the protrusion spike (FIG. 25). This seems to have an impact on VLP stability: the spike of the HEV C-subunits appeared weakly defined compared to that in the A-B dimer, while the spike of the Norwalk virus (NV) C-subunit appeared rigid and similar to that in the A-B dimer in the cryo-EM structure (Prasad, B. V. V. et al., J Mol Riol 240, 256-264 (1994)). Additionally, deletion of the N-terminal positively charged amino acids from the NV capsid protein does not induce T=1 VLP because the NV capsid protein only contains a short N-terminal tail of 20 amino acids (Bertolotti-Ciarlet, A. et al., J. Virol. 76, 4044-4055 (2002)).

The HEV C-C dimer is profoundly different from the HEV A-B dimer in the orientation of the P domain relative to the S2/S1 domain (FIG. 22). Conformational difference between A-B dimer and C-C dimer has been reported earlier on tomato bushy stunt virus (TBSV) and other T=3 viruses. In TBSV, binding of RNA plays an important role to differentiate the C-C dimer from the A-B dimer. The N-terminal arm of the C-C dimer is well-ordered and interacts with the RNA genome, while the A-B dimer is disordered and free from RNA interactions (Timmins, P. A. et al., Structure 2, 1191-1201 (1994)). In Flock House Virus, the C-C dimeric contact acquires a flat conformation to accommodate the RNA duplex, while the A-B dimer is in a bent conformation and involves no RNA (Fischer, A. and Johnson, J. E., Nature 361, 176-179 (1993)). The different orientation observed between HEV C-C dimer and the A-B dimer may result from the difference on RNA occupancy. The A-B dimers do not interact with RNA and have a bent conformation. As a result, the angled contact of the S2/S1 domains accommodated the proline-rich hinge within the V-shaped cleft, similar to that in the T=1 VLP, thus solidifies the orientation of the P domain (FIG. 22c). In contrast, the contact with the RNA led the C-C dimer to a flat conformation that pushes the hinge out of the cleft. Thus the P domain in the C-C dimer is flexible and could take a 90° rotation from the orientation in the A-B dimer (FIG. 22d).

Figure 23:
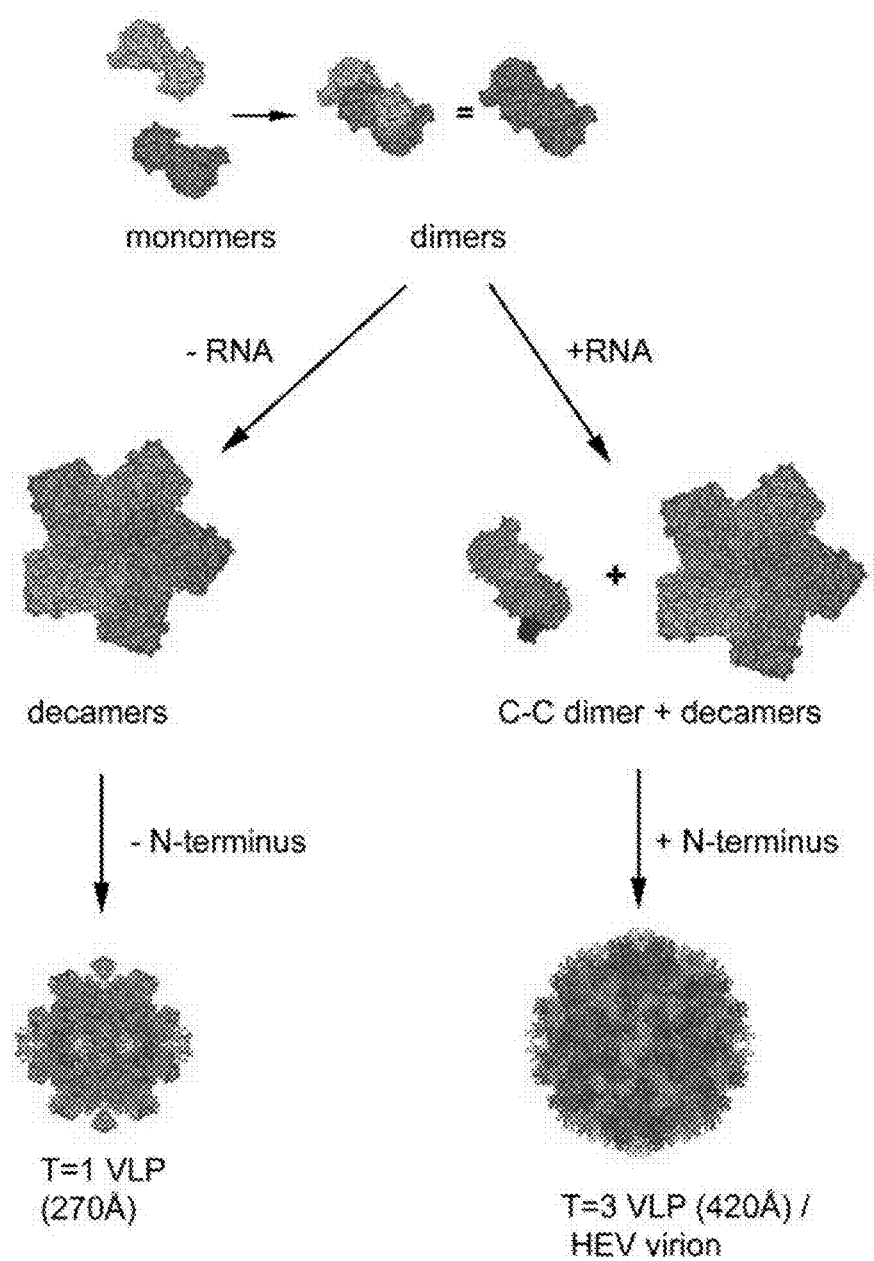

It is suggested by molecular simulation that T=3 icosahedral capsid assembly utilizes a mechanism in which preformed aggregates of intermediates combine in contrast to the formation of the T=1 icosahedral capsid that includes the addition of predominately monomers (Ngyyen, H. D. et al., J Am Chem Soc. 131, 2606-2614 (2009)). The ORF2 decamer is therefore the assembly intermediates of T=3 HEV capsid and located at each of the fivefold vertex. The appearance of a hexameric ring at icosahedral threefold positions is the critical step in T=3 capsid assembly and depends on the C-C dimer. The in vitro disassembly-and-reassembly also indicates the involvement of extrinsic factor than the ORF2 protein in the assembly of T=3 VLP and the C-C dimer is in a flat conformation that is concomitant with RNA binding. The induction of C-C conformation has been reported with bacteriophage MS2, where the complete assembly of capsid requires the presence of synthetic RNA fragment (Stockley, P. G. et al., *J Mol Biol* 369, 541-552 (2007)). Therefore, the interaction of RNA with the N-terminal end of ORF2 is the driving force leading the C-C dimer to the flat formation and ultimately full capsid formation through the integration of 30 copies of C-C dimers with 12 copies of A-B decamers (FIG. 23).

The existence of the N-terminal 111 amino acids prevents ORF2 proteins from forming T=1 VLP. The capsid of T=1 VLP encloses a central cavity with a volume allowing maximum 55 additional residues on each copy of PORF2 protein, if the average protein density is considered to be 1.30 g/ml. The central cavity of HEV T=3 VLP is about 340 Å in diameter, which is sufficient to accommodate both the HEV genome and ORF2 N-terminal domains. By characterizing the size and the N-terminal sequence of the encapsidated RNA, we found that the T=3 HEV VLP selectively encapsidated the RNA fragment that encodes the sequence of ORF2 protein (Li, manuscript in preparation). Thus, it is very possible that the native HEV capsid is T=3 icosahedron. There, the encapsulated genomic RNA may play a direct role in the assembly of HEV infectious virion. However, our data demonstrated here that HEV was different from caliciviruses in its assembly pathway, protein domain arrangement, and genome organization, although both viruses are T=3 icosahedral particles with dimeric spikes. Hepatitis E virus showed a high similarity to some plant viruses in its assembly pathway and its utilization of a long electropositive N-terminal domain. Although the evolutionary origin for such similarities requires further investigation, our data place HEV structure in a unique position, deviating from that of human caliciviruses and approaching that of T=3 small plant viruses.

TABLE 2

Data collection and refinement statistics (Molecular Replacement)

|  | Crystal 1 | Crystal 2 |
| --- | --- | --- |
| Data collection | | |
| No. Crystals | 1 | 2 |
| Space group | $P2_12_12_1$ | $P2_12_12_1$ |
| Cell dimensions | | |
| a, b, c (Å) | 337.00, 343.00, 346.00 | 337.00, 347.00, 354.00 |
| α, β, γ (°) | α = β = γ = 90° | α = β = γ = 90° |
| Resolution (Å) | 70.0-8.30 (8.60-8.30) | 70.0-3.80 (3.94-3.80) |
| $R_{sym}$ or $R_{merge}$ | 0.136 (0.500) | 0.136 (0.626) |
| I/σI | 8.3 (2.2) | 6.3 (1.0) |
| Completeness (%) | 87.6 (89.4) | 68.4 (24.8) |
| Redundancy | 3.0 (3.0) | 3.4 (1.4) |
| Refinement | | |
| Resolution (Å) | | 20.00-3.80 |
| No. reflections | | 275,008 |
| $R_{work}$/$R_{free}$ | | 0.242/0.245 |
| No. atoms | | |
| Protein | | 3.659 |
| Ligand/ion | | 0 |
| Water | | 0 |
| B-factors | | |
| Protein | | 140.7 |
| Ligand/ion | | |
| Water | | |

TABLE 2-continued

Data collection and refinement statistics (Molecular Replacement)

|  | Crystal 1 | Crystal 2 |
| --- | --- | --- |
| R.m.s deviations | | |
| Bond lengths (Å) | | 0.010 |
| Bond angles (°) | | 1.7 |

Example 5

Engineered Nucleopeptide Capsid of Acute Hepatitis E Virus Possesses Functional Modularity as Oral Vaccines Hepatitis E virus (HEV) is a water-borne viral agent and primarily transmitted via fecal-and-oral route thus resistant to low pH and digestive enzymes associated with stomach and digestive tracts. The infection of HEV causes acute hepatitis in human with a mortality rate up to 30% in pregnant women (Naik, S. R. et al., *Bull World Health Organ,* 70 (5), 597-604 (1992)). Currently, there are 1,600 genomic sequences of HEV available at the International Nucleotide Sequence Database Collaboration (Khuroo, M. S. & Khuroo, M. S., *Curr Opin Infect Dis,* 21, 539-543 (2008)), which are grouped into four genotypes (Jameel, S., *Expert Rev Mol Med,* 1999, 1-16 (1999)). Notably, only a single known serotype is recognized, suggesting that the immuno-dominant domain of HEV is highly conserved. The major capsid protein ORF2, encoded at the second open reading frame, is reported most immunogenic and is responsible for the induction a protective humoral immune response((Li, T. et al., *Vaccine,* 22, 370-377 (2004); Purdy, M. A. et al., *J Med Virol,* 41 (1), 90-94 (1993); Riddell, M. A., Li, F., & Anderson, D. A., *J Virol,* 74 (17), 8011-8017 (2000)). Recombinant HEV capsid protein (PORF2) covering amino acids 112-608 can self-assemble into virus like particle when expressed in insect cells (Li, T. C. et al., *J Virol,* 71 (10), 7207-7213 (1997)). Although HEV virion is a non-enveloped icosahedral particle with a diameter of 320-340 Å as shown by immuno-electron microscopy (Balayan, M., Andiaparidze, A., Savinskaya, S., & et. al., *Intervirology,* 20, 23-31 (1983)), self assembled virus-like particles have a diameter of 270 Å determined from its three dimensional reconstruction. The HEV-VLPs possesses HEV native immunogenicity and is capable of inducing anti-HEV systemic and mucosal antibodies when orally administered to non-human primates (Li, T. et al., *Vaccine,* 22, 370-377 (2004)). Although the HEV-VLP was determined as T=1 icosahedral particle composed of 60 copies of PORF2 proteins, detailed structural information about amino acids arrangement is still necessary to better utilize HEV VLP either as derict mucosal vaccine against hepatitis E or as delivery carrier to activate immune response at mucosal surface.

Figure 28:
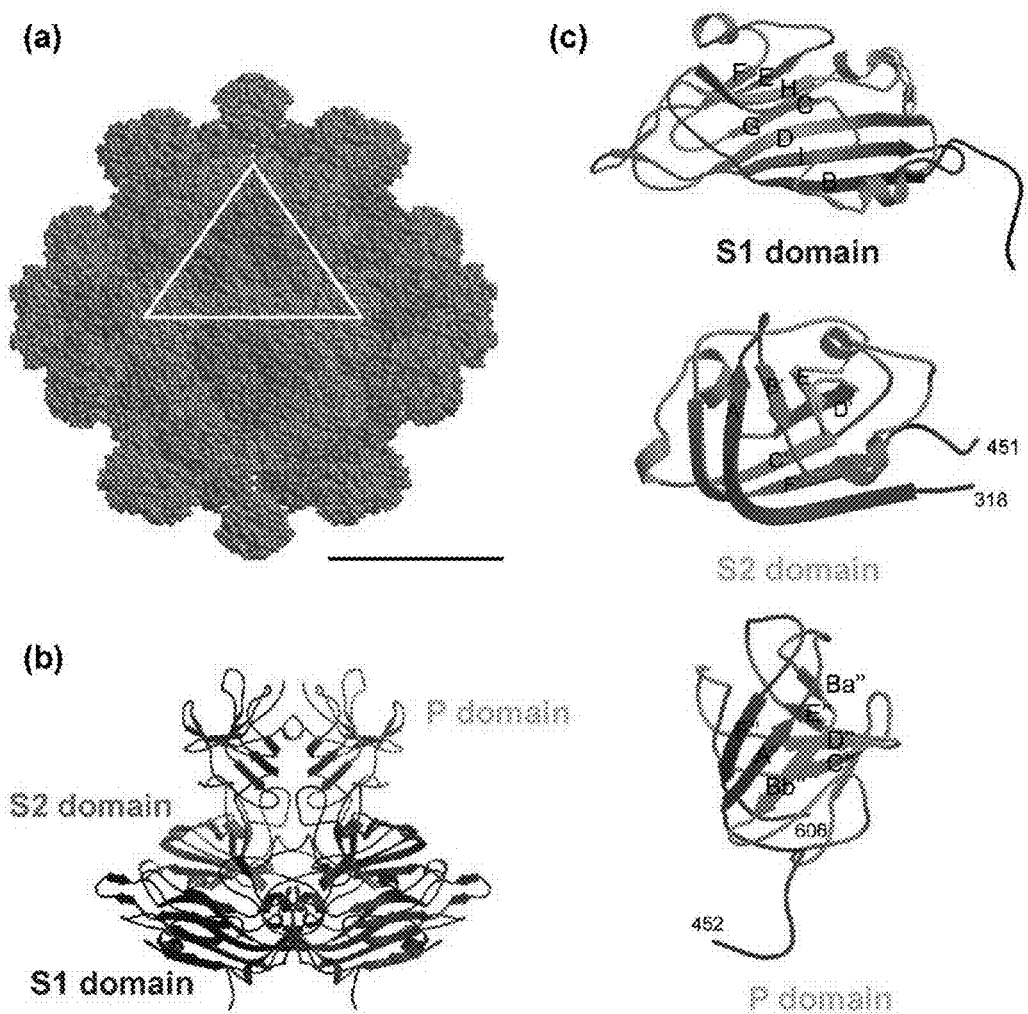
FIG. 28. Overall strucuture of genotype 1 HEV-VLP. (a) A CPK model of the capsid structure viewed down an icosahedral two-fold axis. The white triangle circulates an icosahedral face. Bar=100 Å. (b) Ribbon representations of the dimer structure of the HEV-VLP capsid protein. (c) A ribbon representation of the Si domain. The β-strands are labeled from B to I, following the nomenclature of caliciviruses. (d) A ribbon representations of the S2 domain. The β-strands are labeled from A' to F'. (e) A ribbon representations of the P domain. The β-strands are labeled from A" to F".
Figure 29:
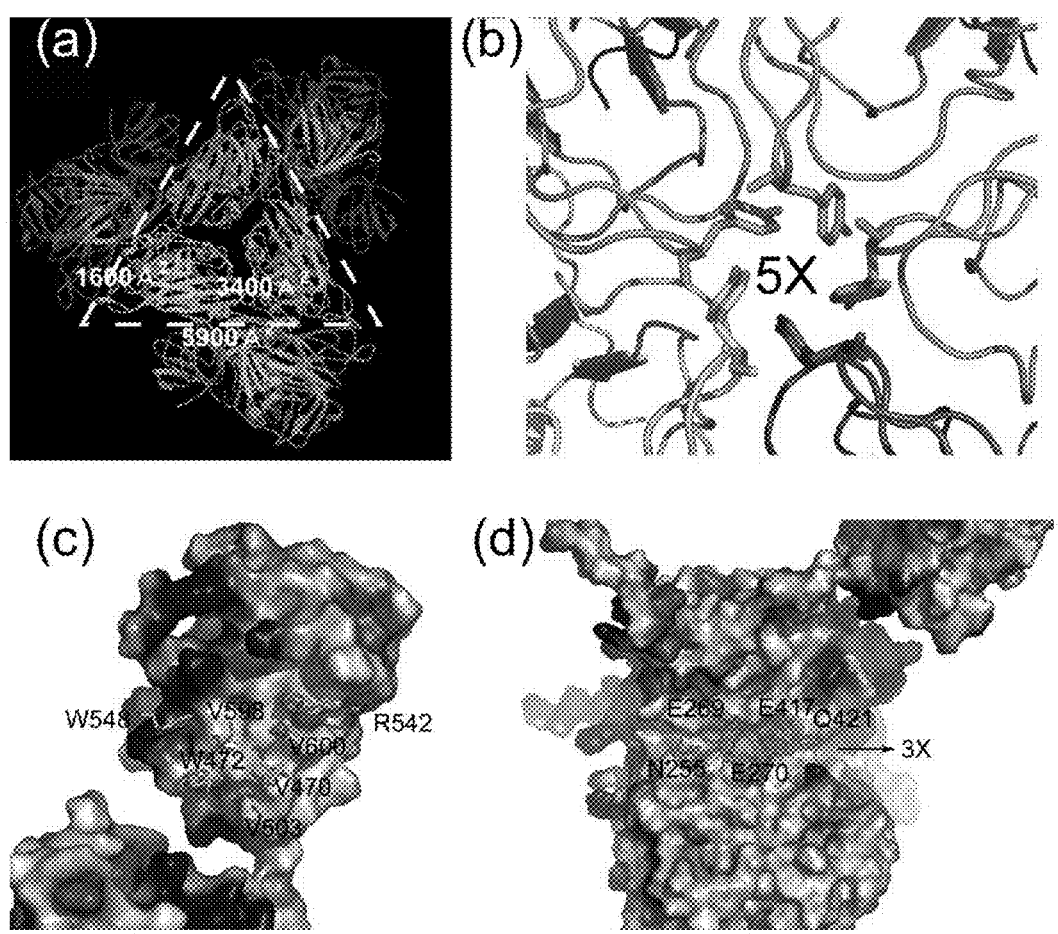
FIG. 29. ORF2 Intersubunit interactions. (a) Surface areas that buried at the interface between the subunits are shown. The white triangle circulates the area of an icosahedral face. (b) A ribbon representation showing the contact at icosahedral fivefold with five Y288 highlighten as stick mode. (c) P domain dimeric interface. The surface electron potential of one P domain is shown. The interacting hydrophobic amino acids from the other subunit are shown as sticks. (d) The density voided channel at threefold position. The surface electron potential of two threefold-related subunits is shown at background to reveal the inner surface. The sticks shows the critical negatively charged amino acids of the third subunit around threefold axis.

To acquire in-depth the structural insight of HEV capsid configuration, we determined the crystal structure of HEV-VLP derived from genotype 1 capsid protein to 3.8 Å resolution by molecular replacement techniques, as initially phased by with a 30 Å cryo-EM density map (Xing, L. et al., *Virology,* 265 (1), 35-45 (1999)) (Table S1). As seen in the cryo-EM structure, the HEV-VLP contains 30 large protruding spikes at each of icosahedral twofold axis (FIG. 28*a*). The structure of the capsid protein can be separated into three domains, S1 domain, S2 domain, and P domain, with a less resolved region covering residues 555-560 (FIG. 28*b*). The S1 domain, formed by residues 118-317, folds into a classical eight-stranded β-barrel with a jelly roll motif, as seen in many T=3 viral capsid proteins (Rossmann, M. G. & Johnson, J. E., *Ann Rev Biochem*, 58, 533-573 (1989); Harrison, S. C., *Curr Opin Struct Biol*, 11, 195-199 (2001)). These eight β strands, denoted B-I, are organized into two antiparallel β-sheets, with two α-helices between the strands C and D and strands E and F (FIG. 28c). Uniquely, three additional short α-helixes were observed in the S1 domain between the strands E and F and strands G and H. The capsid shell appears to be mainly stabilized by the inter-subunit interactions between the S1 domains. The folding of S2 domain, consisting of residues 318-451, is a twisted antiparallel β-sheet and a α-helix between B' and C' strands (FIG. 28c). S2 domain is raised mainly around the 3-fold axis (FIG. 28c), and interacts strongly with the underneath S1 domain, with a buried surface area (BSA) of ~3,200 Å2 (FIG. 29a). Both the S2 and the P domains exist above the S1 domain, however, the protruding spikes in the cryo-EM map include solely the P domain density. The P domain, composed of residue 452-606, folds into a β-barrel composed of antiparallel β-sheets, F"A"Bb" and Ba"E"D"C" (FIG. 28c) and connects with the S2 domain through a long proline-rich hinge (PTPSPAPSRP (SEQ ID NO:8) of residues 452-461) (FIG. 28c). This HEV capsid protein demonstrates a clearly difference in the spatial domain organization and the sequence of the three domains and a strong similarity in the folding of each individual domain to the capsid proteins of caliciviruses reported to date (Prasad, B.V.V. et al., *Science*, 286 (5438), 287-290 (1999); Chen, R. et al., *Proc Natl Acad Sci USA*, 103, 8048-8053 (2006)).

The subunit interface at each of the twofold axis demonstrates the largest BSA on monomers (5,900 Å²) mainly due to the contacts at P domains (FIG. 29a). This interface buries a group of non-polar amino acids involves strong hydrophobic interactions. The side chain of amino acids of Val 470, Trp472, Val 503, Val598 and Val600 from one subunit is embraced by the hydrophobic surface patch from its dimeric partner (FIG. 29b). This hydrophobic contact is protected by a rim of polar interactions on each site, including a hydrogen-bond made between residue Trp548 of one subunit and residue Arg542 from its twofold partner. Thus the PORF2 dimer is stable in solution and the dimerization was reported to be consistent with the presence of amino acids 585-610 (Li, X., Zafrullah et al., *J Biomed Biotechnol*, 1 (3), 122-128 (2001)). Further mutagenesis analysis confirms that the dimeric interactions is in association with the presence of six hydrophobic amino acids residues, Ala597, Val598, Ala599, Val600, Lue601, and Ala602 (Li, S. et al., *Vaccine*, 23 (22), 2893-2901 (2005)). In the crystal structure, these residues located at P domain either at the dimeric interface or within the hydrophobic core of the β-barrel. In addition, the S1 domains arranges hydrophobic residues at the dimeric interface, particular the βB-strand and α1-helix, as an additional force to stabilize HEV dimer. Therefore, the capsid protein dimers are likely the building block in the assembly of HEV-VLP and insertion at these interface region would inhibit the formation of HEV-VLP.

To assemble ORF2 dimers into an icosahedral shell, 30 copy of PORF2 dimers have to be positioned following the strict fivefold and threefold symmetry where large surface area of each dimer is buried in during the assembly. As a result, the surface of S1 domain is only accessible at region around fivefold axis thus the fivefold connection involves the residues solely from S1 domain with 4,700 Å2 buried surface area. The fivefold apex is surrounded by a ring of five Try288 residues with their aromatic side chain pointing towards the center (FIG. 29c). The connection around threefold axis invovles both S1 and S2 domains with 9,500 Å2 buried surface area (FIG. 29a). A density voided cavity was observed at threefold axis where residues Gln421 from S2 domain and Asn255 from S1 domain were observed to occupy the outermost and innermost amino acids, respectively. The wall of this hollow is highly negatively charged and contains three amino acids Glu269, Glu270 and Glu417 (FIG. 29d). At current resolution, we are unable to detect any electron density for metal ion in the structure. However, HEV-VLP can be disassembled in an environment containing both EDTA and DTT, while reassembled by addition of calcium ion. The calcium-ion dependent stability suggests the existence of divalent ion in the capsid, although the exact location of the divalent ion requires further systemic analysis, for example derivatizing crystals with samarium. As the "energy landscape" of macromolecular assembly has been suggested to take stepwise process, in which the larger interface is most likely conserved in evolution (Levy, E. D. et al., *Nature*, 453, 1262-1265 (2008)). The BSA of dimer-dimer contact suggests a possible assembly route of PORF2 dimer through hexamer (trimer of dimers) around threefold axis because it conducts large BSA compared to the decamer (pentamer of dimers) around fivefold axis.

Sequence alignment of capsid protein from the four genotypes of HEV revealed that the S1 domain is the most conserved region, while S2 domain is hyper variable among genotypes (Zhai, L., Dai, X., & Meng, J., *Virus Res*, 120, 57-69 (2006)). The heavy involvement of S1 domain in sealing the VLP capsid with low solvent accessibility may keep this domain region of protein sequence more conserved among genotypes. There are 9 divergent residues in S2 domain and all of them locate at the solvent-exposing surface, however, none of the known HEV antigenic epitope was located at the S2 domain.

Figure 30:
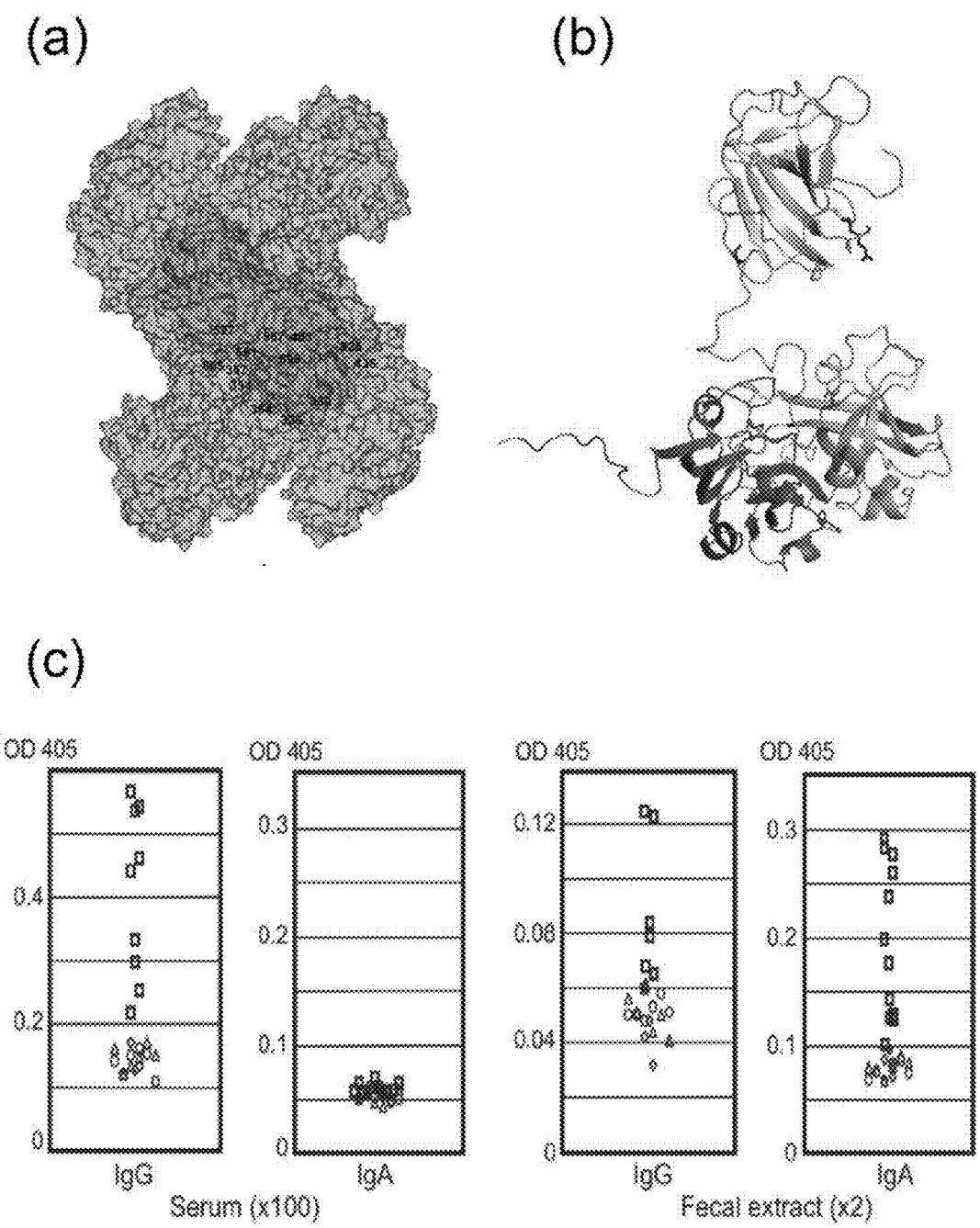
FIG. 30. HEV-VLP structure demonstrates its cargo ability for delivery of heterogenous epitopes. (a) Surface representation of a dimer and the surrounding dimers showing the specific residues for the HEV genotype 1 (G1) among HEV genotypes (G1, G3 and G4) as viewed from the outside of the shell. The specific residues in the S2 and P domains of the dimer are labeled. (b) Previous insertion sites are failed because they interfere with either dimeric or dimer-dimer interactions. Two insertion sites are located at 51 domain and S2 domain respectively. Two other sites are located at dimeric interface of the P domain. (c) Humoral response to the chimeric epitope. Mice were given three oral immunizations with one of the following: chimeric HEV-VLP carrying HIV P18 epitope (P-VLP/P18, square), chimerically-synthesized HIV P18 epitopes peptide (triangles), or HEV-VLP (circle). No treatment controls are shown by diamonds. Sera and fecal suspension (200 mg/ml) were diluted (1:100 and 1:2 respectively) and the specific antibodies to the chimeric epitope were evaluated in ELISA using synthetic peptide as the antigen.

The P domain is highly exposed and serves as the binding sites for neutralizing antibody (He, S. et al., *J Gen Virol*, 89 (1), 245-249 (2008)). The neutralization epitope of HEV is reported to be conformational (Schofield, D. J. et al., *Vaccine*, 22 (2), 257-267 (2003); Meng, J. et al., *Virology*, 288, 203-211 (2001) and the peptide including residues 459-607 of the capsid protein is then identified as the minimal structure to induce anti-HEV neutralizing antibody (Zhou, Y. H., Purcell, R., & Emerson, S., *Vaccine*, 23, 3157-3165. (2005)). This region coincides with the P-domain revealed in our structure and does not involved in the formation of icosahedral shell. The results of sequence alignment revealed 19 divergent residues at P domain and 9 of them on the VLP surface (FIG. 30a). Strikingly, only one of them locates within the antibody binding interface, which is further confirmed by cryo-EM structure of antibody-conjugated HEV-VLP (manuscript in preparation). There has been only one HEV serotype reported so far, regardless the fact of four existing genotypes. The divergent amino acids of four genotypes are located exterior on the surface of the anigenic domain. Modularization of PORF2 protein by assigning assembly function to the S1 domain and immunogenicity to the P domain essures HEV-VLP preserving its native antigenic conformation even the VLP is smaller than the native virion. Alternatively, making mutation or engineering of P domain will not affect the assembly of HEV-VLP.

Four insertion sites were previously selected after residues A179, R366, A507, and R542 according to the conveniece of restriction enzyme. These fusion proteins failed in VLPs production (Niikura, M. et al., *Virology*, 293 (2), 273-280 (2002)) due to the wrong spatial positions of these residues. The residue A179 is located in the S1 domain in the middle of α1 helix. This helix is necessary for the integrity of S1 domain and the interaction with its twofold related neighboring subunit. R366 is located in the S2 domain and favors electrostatic interaction with residue E386 from its threefold related neighboring subunit. Although located at P domains, the side chain of R542 is within the dimeric interface and guides the hydrophobic interaction of two monomers. Deletion of R542 may misalign the orientation two P domains that weaken the dimeric interaction of PORF2 protein. The role of residue A507 in the P-domain plays an important role in maintaining P domain orientation by fixing the angle to the long proline-rich hinge. None of the four residues are exposed on the surface of VLP, although some of them are at the surface of individual PORF2 subunits (FIG. 30b). Therefore, insertion of a foreign sequence at these sites induces no interference to the expression of individual protein, but does bring in hindrance to the assembly of HEV VLPs. The crystal structure revealed that the C-terminus is exposed on the surface of VLP and is suitable to tether bulky foreign antigenic sequences, as it showed in the previous report (Niikura, M. et al., *Virology*, 293 (2), 273-280 (2002)). To create a mucosal vaccine against HIV infection, a HIV immunogenic epitope P18 was inserted to the C-termini of PORF2 protein.

The infection of human immunodeficiency virus (HIV) is a major health problem that results in an estimated 2.7 million new infections and 2 million deaths in 2007. Mucosal vaccine is particular rubust in targeting the initial infection and replication of HIV because the majority of primary infections of HIV occur at mucosal site (Miller, C. L., McGhee, J. R., & Gardner, M. B., *Lab. Invest.*, 68, 129-145 (1993)). HIV P18 peptide (RIQRGPGRAFVTIGK; SEQ ID NO: 9) is a specific HIV peptide located at the third variable domain of HIV-1 envelope glycoprotein. This domain contains a T helper (Th) and the principal HIV-1 neutralization epitopes. The P18 peptide is immunodominant and able to stimulate HIV-specific CTL response (Achour, A. et al., *J Virol*, 70, 6741-6750 (1996)). Fusion of P18 peptide to the C-terminal end of PORF2 protein did not affected the assembly of HEV-VLP. As a result, the inserted P18 epitope is positioned adjacent to HEV immunodominant epitope and expected to be accessible to the host immune system. Each HEV-VLP will carry 60 copies of P18 epitope, with spacing of 56 Å due to its icosahedral symmetry. Mice were then orally immunized three times at 1 week interval with 50 mg of purified chimeric P18-VLP in the absence of adjuvant. HIV Env-specific IgG antibodies were detected in sera and in intestinal fluid with a level higher than those in mice that had received synthetic P18 peptide (FIG. 30c). Moreover, specific IgA antibodies to HIV env-protein were detected from the mouse intestinal fluid, while the level of IgA antibodies in sera showed no difference to that detected in peptide-immunized mice (FIG. 30c). The control mice immunized with wild type HEV-VLP developed no antibodies specific to the synthetic P18 antigen. This suggests that the chimeric P18-VLP is capable of inducing both systemic and mucosal immunity in mice.

Figure 31:
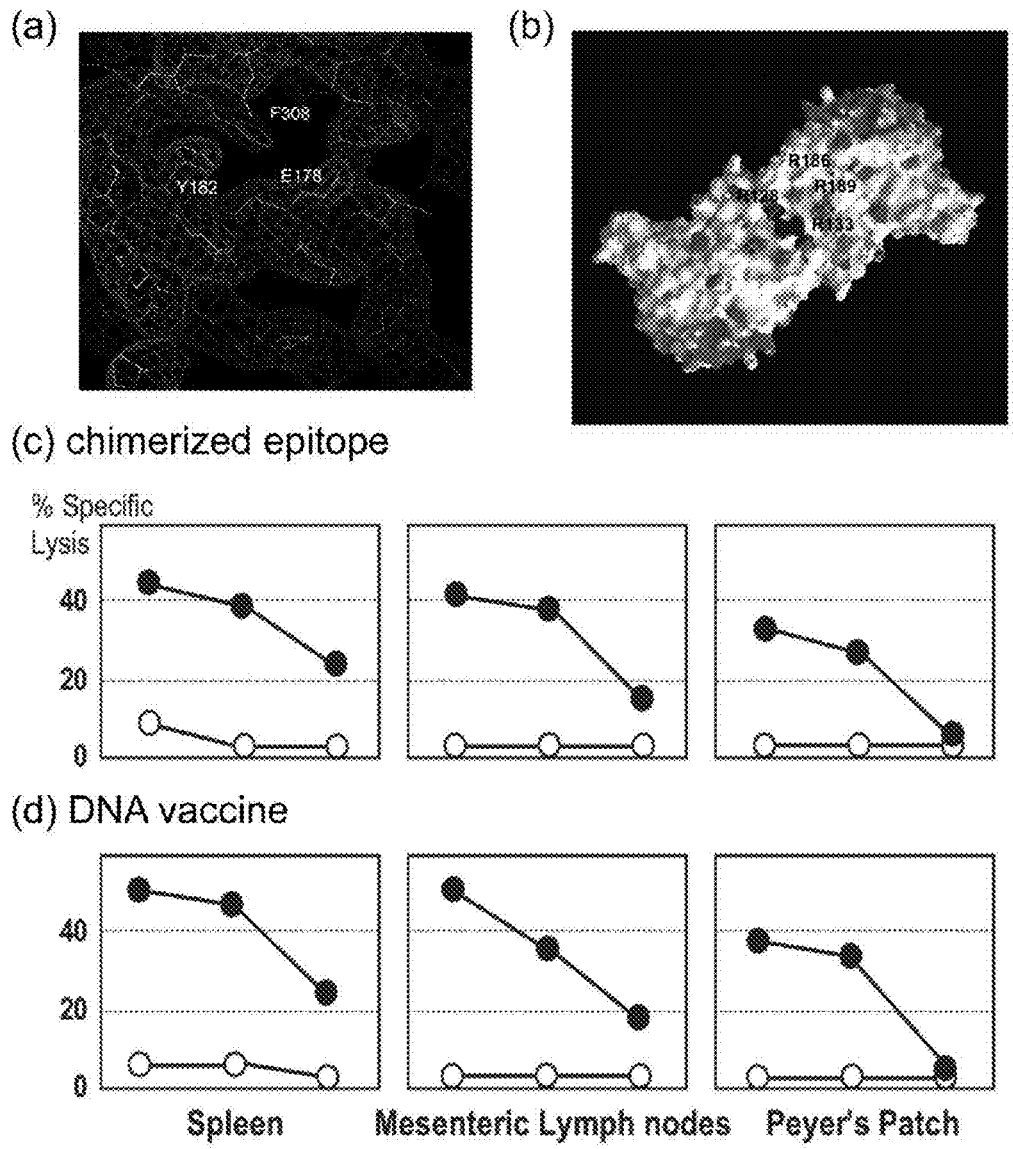
FIG. 31. HEV-VLP is capable of carrying DNA plasmid for gene delivery. (a) A sample electron density map with modeled amino acid residues in the 51 domain. (b) Electron potentials on the surface of the dimer at the icosahedral 2-fold axis, as viewed from the inside of the capsid shell. Positively charged residues around 2-fold axis are labeled. The figure was prepared with Swiss-PDB Viewer. (c), (d) CTL response to the chimeric epitope and encapsulated DNA vaccine. Mice were orally immunized with chimeric HEV-VLP that bore HIV P18 epitope one the surface and an encapsulated DNA vaccine expressing entire Gag protein (P-P18/N-Gag capsule). Specific lysis by CTL in response to either the P18 epitope (c) or Gag protein (d) was evaluated by testing spleen, mesenteric lymph nodes and Peyer's patch cells from immunized animals (closed circles). Control tissues (open circles) were from mice fed with chemically-synthesized P18 epitope peptide (c) or a naked DNA vaccine expressing Gag (d). The effector/target ratios (80/1, 40/1, and 20/1, shown left to right in each panel) were tested.

The chimeric P18-VLP, like the HEV-VLP, contains a cluster four positively charged amino acids in the interior surface of capsid around the icosahedral twofold axis (FIG. 31b), forming a local environment favorite nucleotide interactions. When DNA plasmid was added in the reassembly buffer, the reassembled chimeric VLP can incorporated with the DNA plasmid. We therefore produced a chimeric VLP bearing HIV P18 epitope on the surface and an encapsulated DNA vaccine expressing entire Gag protein (P-P18/NGag capsule) and evaluated its immunogenicity experimentally with mouse. After orally immunizing four times at 1 week interval of P-P18/N-Gag capsule, the mice developed both HIV specific IgG and IgA antibodies in serum and in intestinal fluid with a level higher than those in mice that had received either synthetic P18 peptide or naked DNA plasmid. Strikingly, cytotoxic T lymphocyte (CTL) responses were detected in response to P18 epitope (FIG. 31c) and to HIV gag protein (FIG. 31d) in the spleen, mesenteric lymph nodes and Peyer's patch cells from the mice orally administrated with P-P18/N-Gag capsule. The specific CTL responses did not observed in the same tissue cells from the control animals fed with either synthetic P18 peptide or naked DNA vaccine expressing gag protein developed. This result demonstrates that gene on DNA plasmid could be expressed in epithalial cells in the small intestine after delivery by HEV-VLPs.

The oral delivery of an HIV DNA vaccine for induction of mucosal immune responses is challenged by the difficulties to protect plasmid DNA from gastric environment, although the efficacy can be improved by encapsulating DNA in poly (lactide-coglycolide) microparticles (Kaneko, H. et al., *Virology*, 267, 8-16 (2000)). HEV-VLP, derived from an orally transmissible virus, is composed of 60 copies of PORF2 protein that modularized its three domains for different functions, such as antigenic presenting and VLP assembly. Such structural modularity of capsid protein allows HEV-VLP to retain the transmission and immunogenic properties of the native HEV virion, thus to be incorporated into HEV-permissive epithelial cells in the small intestine. Furthermore, these results demonstrated that our HEV-based P-P18/NGag capsule was capable of taking the advantages of HEV-VLP in going through the mucosal system by not only delivering the antigen to mucosal surface, but also notably inducing the humoral and the cellular mucosal, as well as systemic, immune responses. Since the HEV-VLP itself is under clinical trials as an HEV vaccine in humans (Shrestha, M. P. et al., *N Engl J Med*, 356 (9895-903) (2007)), this delivery system of HEV-VLP provides a facile novel tool of oral vaccine delivery as a non-replicating entity that can induce mucosal immunity without any adjuvant.

Example 6

HEV-VLP Encapsulating a DNA Vaccine

This invention of vaccine platform will not simply deliver an encapsidated a plasmid DNA but will also attach a peptide epitope to the surface of the virus-like particles (VLP) as both adjuvant and booster to maximize the efficacy. This should make feasible the induction of cellular immunity, both helper T cells and, importantly for viral infection, MHC class I-restricted cytotoxic T lymphocytes. This attempt is considered to be potent than the general VLP delivery system when the VLP is used to carry one type of antigen, either peptide or DNA, because the attached antigen functions as both adjuvant and booster to enhance the efficacy of the DNA vaccine. The whole production does not require the handling of potentially deadly influenza virus and significantly shorten production time, thus composed a feature paramount with an ongoing pandemic. The encapsidation of DNA vaccine is done entirely in vitro; therefore M2e conjugated HEV VLP can be produced in advance as an envelope to enclose the DNA plasmid containing RNA segments of the potential pandemic virus that was generated through reverse genetics.

The natural route of infection for HEV is the fecal-oral route, and the structure of HEV-VLPs enables it to survive the low pH of the stomach in order to pass through to the small intestine where infection of the intact virus normally occurs. Thus as a vaccine delivery system, it is able to induce mucosal immunity and even advantageous compared to, for example, certain cholera vaccines which require pre-administration of a buffer. An effective vaccine must be capable of being readily manufactured. The HEV-VLP can be produced from standard cultivation methodologies with a yield of purified HEV-VLPs in the range of 50-100 µg/ml, nearly 100 times greater when compared to other VLPs. The produced capsid is stable at room temperature and can be transported in the absence of cold facility, a critical feature for its potency, particular in the remote low-resource regions. Mucosal surface builds up the front line of defense in human against the entry of infectious microorganisms. This is particular true for the infection of human immunodeficiency virus (HIV) because the majority of HIV primary infection takes place at mucosa. In addition, injected vaccines require the use of sharps (needles) or injectors, both of which have the disadvantages of causing pain (which results in a number of people avoiding immunization), and of creating a biohazard. Because trained personnel are required to administer such vaccines, administration of an injected vaccine is likewise more costly than for an orally administered vaccine, for example. However, the development of mucosal vaccine relies heavily on the efficiency of antigen delivery system, which has to be strong enough to protect antigen against the harsh environment, such as proteolytic enzymes in human digestive tract, and targeting the mucosal surface.

HEV-VLP is able to activate mucosal immunity: Human hepatitis E virus (HEV) is a water-borne non-enveloped virus that transmitted primarily through the contaminated water. The Hepatitis E virus like particle (HEV-VLP) is composed of the truncated ORF2 protein (PORD2) derived from the capsid protein. When expressed in insect cells, the PORF2 protein self-assembles into T=1 icosahedral particle with a high yield (milligram quantities at laboratory scale). We then analyzed its structure with both cryo-electron microscopy and image reconstruction and recently by X-ray crystallography. The VLP consists of 60 copies of PORF2 protein and contains no nucleotide, thus unable to replicate in host cells. Although it is smaller than the native virion (27 nm vs 34 nm), this VLP demonstrated similar morphological features as the native HEV virion: showing protruding spikes on the surface of the icosahedral shell. Additionally, it also retains HEV native antigenicity and capable of inducing antibodies in experimental animals and protection in non-human primate. Taking the advantage of HEV natural infection route, the detection of IgA antibody in both mice and cynomolgus monkeys after oral vaccination demonstrates that HEV-VLP is capable of eliciting mucosal immunity.

Figure 32:
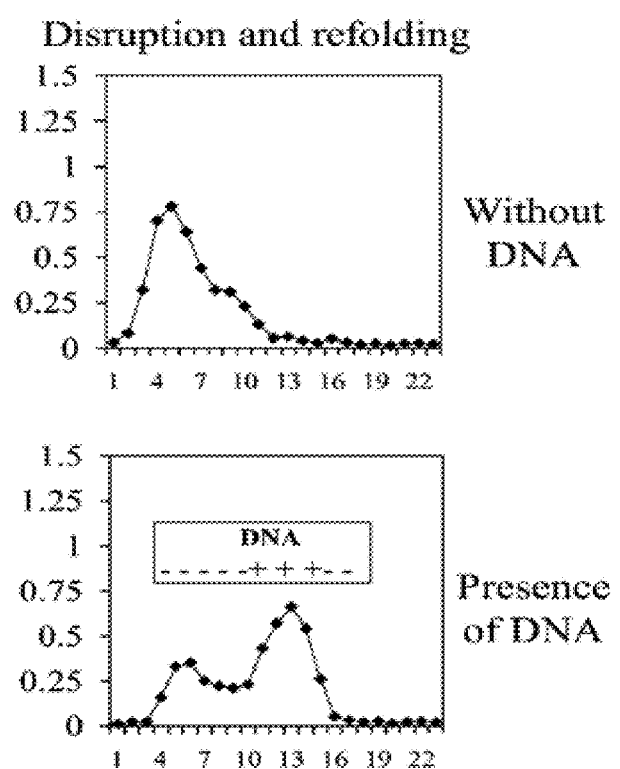
FIG. 32: Separation of DNA-loaded HEV-VLPs from the empty VLPs by CsC1 density gradient.
Figure 33:
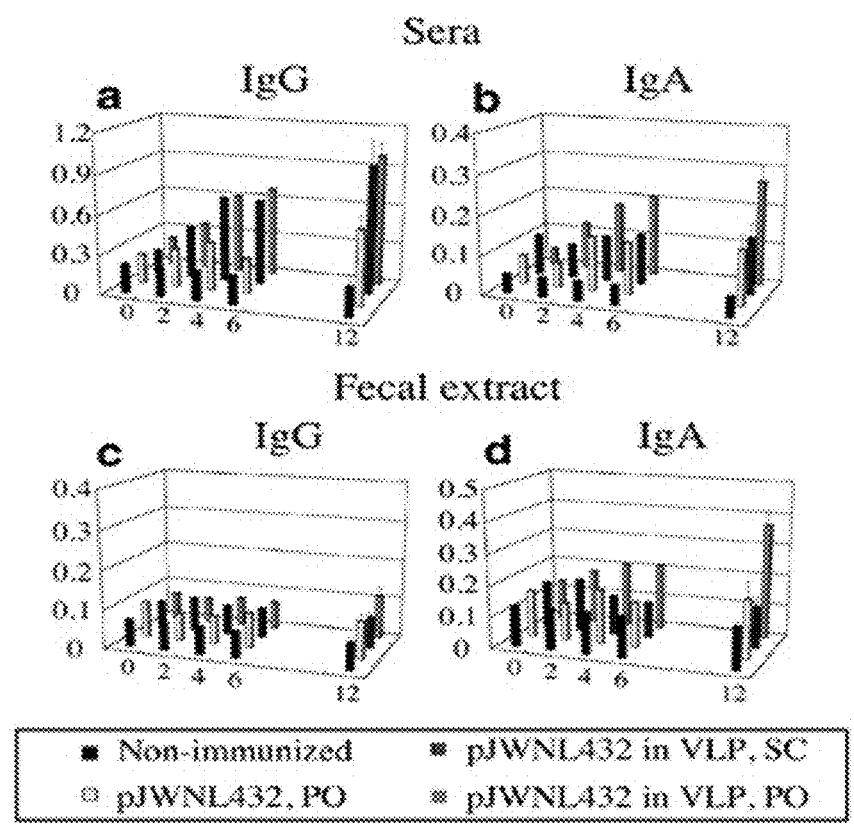
FIG. 33: Level of anti-P18 specific IgG (a, c) and IgA (c, d) antibodies in sera (a, b) and fecal extrat (c, d).
Figure 34:
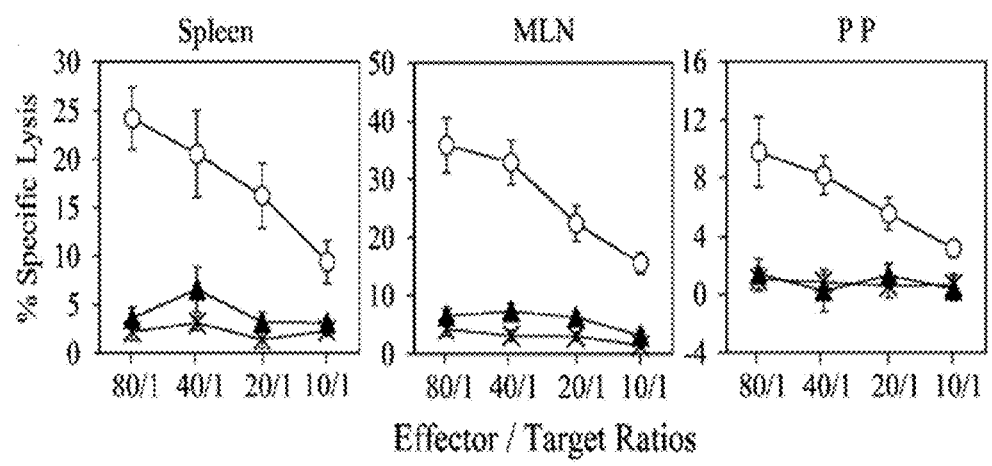
FIG. 34: Spleen, MLN, and PP cells from mice orally received plasmid-loaded VLP (circles) elicited specific CTL responses, while the naked plasmid (triangles) and non-immunized control (cross) did not.

HEV-VLP is able to transfer genes in vitro and in vivo: The structure of HEV-VLP revealed that the inner VLP inner surface contains a dominant positively-charged patch at each of icosahedral two-fold axis, indicating that the VLP retains the intrinsic capacity of encapsidation nucleic acids. Thus this HEV-VLP is able to encapsulate DNA plasmid in vitro during VLP refolding and transfer GFP-gene into the culture cells derived from mice, rabbit, monkey and human. Combination of EGTA and DDT can disassemble the HEV-VLP into free dimers and the disrupted VLPs can be reassembled when calcium ions are supplemented. No significant morphological changes were observed after negative staining To incorporate DNA vaccine, plasmid DNA encoding target gene was mixed with the disrupted VLP before refolding. The plasmid-encapsidate VLP is then separated from the empty VLP by CsCl density gradient (FIG. 32). The fluorescence of GFP-expressing cells was observed under a fluorescence microscope. Although the percentages of GFP transfected cells were not so high (11.2% of NIH3T3 cells, 19.6% of RK-13 cells, 21.0% of COS-7 cells, and 20.1% of HepG2 cells), all of the cell lines tested in the study showed positive reaction, in contrast to the cells that were incubated with plasmid DNA alone or intact HEV-VLP in the presence of plasmid DNA. To test whether HEV-VLP could induce gene transduction in vivo, we reassembled HEV-VLP so it encapsulated plasmid DNA expressing HIV env gp120 of the NL432 strain (pJWNL432). Mice that orally received this VLP were killed two days after immunization and the expression of HIV env protein was found in epithelial cells of the small intestine by immunohistochemistry. These data demonstrated the ability of HEV-VLP as gene carrier for mucosal delivery.

HEV-VLP delivery is able to induce specific mucosal immune responses in mice: Mice were orally and subcutaneously immunized with either HEV-VLP containing pJWNL432 or naked pJWNL432 plasmid four times at 1-week intervals. Sample was collected from mice serum and fecal at different time points after immunization and the level of antibody induction was examined with ELISA, against HEV-VLP, synthetic HIV P18 peptide, and CV-1 cells infected with recombinant Sendai virus expressing HIV gp120 protein of NL432 strain. The serum levels of HIV env-specific IgG antibodies detected in sera from subcutaneously and orally immunized mice are eventually the same, while no IgG was detected in any of the fecal samples. However, the level of IgG are significantly higher in sera of the mice received DNA-loaded VLP than that had received naked DNA ($P<0.05$ at 12 wpi) (FIG. 33). Here, the statistical analysis was performed using Mann-Whitney's U-test and Kruskal-Wallis test.

Importantly, specific IgA against HIV env is only detected at high levels in the sera of mice that had been immunized orally with DNA-loaded VLP but not in the sera of mice that had been immunized subcutaneously ($P<0.05$ at 12 wpi). Such specific IgA was only detected in fecal extracts of the mice that had orally received DNA-loaded VLPs (FIG. 33). These data indicate that HEV-VLP is effectively deliver DNA vaccine to mucosal surface.

HEV-VLP delivery is able to elicit specific CTL responses in mice: One of the significant advantages of DNA vaccine is to stimulate both antibody and T-cell arms of the immune system inducing those that are specialized to kill viruses via cytotoxic or killer T-cells. To exam whether HEV-VLP delivery induces cellular responses; we investigated cytotoxicity by 51Cr-release assay on the effector cells that was collected from spleen, mesenteric lymph nodes (MLN) and Payer's patch (PP) cells at five weeks after first immunization. The P18 peptide is a dominant HIV env CTL and Th cell epitope in BALB/c mice and is restricted to the H-2$D^d$ allele Inhibition of these effector cells by either anti-CD8 or anti-H-2$D^d$ monoclonal antibody was also investigated. The results revealed that the mice can develop HIV-env epitope-specific CTL responses in spleen, MLN, and PP after receiving plasmid-loaded HEV-VLP, which the mice received naked DNA plasmid did not develop such specific CTL responses (FIG. 34). The function of these effectors cells were inhibited by anti-CD8 and anti-H-2$D^d$ monoclonal antibodies. Therefore, oral administration of mice with HEV-VLP encapsidated HIV env DNA vaccine elicited CD8+ and MHC class I-restricted CTL responses both locally and systemically.

Both HIV antigenic epitope P18 and DNA vaccine were delivered using human hepatitis E virus capsid particles. P18 epitope is located in the third variables domain (V3 loop) of the HIV envelope glycoprotein and contains a T helper and the principle HIV neutralization epitopes. Administration of P18 is able to induce anti-HIV CTL responses that appear to play an important role in the control of HIV infection by killing the infected cells. The HIV DNA vaccine is plasmid encoding HIV soluble glycoprotein gp120. The expressed gp120 protein can be selected for presentation at the surface of infected cells by association with major histocompatibility complex class II (MHC II) molecules, thus activate CTL responses. It is known that HIV-specific CTL responses have a critical role in controlling HIV replication because CD8+ T lymphocyte responses emerge during acute infection coincident with initial control of primary viremia. With the structural information achieved lately, we are able to modify HEV capsid protein so as to let such capsid deliver both P18 epitope and gp120 gene simultaneously to the mucosal surface through oral administration. Therefore, the proposed system can stimulate induction of systemic and mucosal antibodies as well as cellular CTL response against HIV infection. HEV-VLP, a highly ordered closure capsid but lacking viral genomic material, retains the overall structure of viral capsid and showed great advantage in delivery of small molecule, antigenic epitopes, and therapeutic gene. In particularly, HEV capsid, as derived from gastroenteric transmitting agents, inherits the natural transmission pathway to target mucosal antigen-presenting cell through oral vaccination. This technology should induce not only antibodies and cellular immunity, but also mucosal immunity (at the site of infection), to play effective role in 1) the induction of anti-HIV antibodies to reduce the virus inoculum, as well as in 2) the activation of cellular responses to facilitate the clearance of HIV-infected CD4 cell.

Example 7

Various Chimeric HEV-VLP Constructs

Various heterologous peptides were inserted into the portion of HEV ORF 2 within a pre-selected region of residues 483-490, residues 530-535, residues 554-561, residues 573-577, residues 582-593, or residues 601-613 of the HEV ORF 2 protein. The heterologous epitopes can be used in these constructs include, but are not limited to, HIV-V3, flu-M2, HSV and reo (diarrhea viruses). Various constructs have been made, including: (1) a HEV-VLP with HIV V3 peptide inserted into the region of residues 483-490; (2) a HEV-VLP with HIV V3 inserted into the region of residues 530-535; (3) a HEV-VLP with HIV V3 peptide inserted into the region of residues 554-561; (4) a HEV-VLP with HIV V3 peptide inserted into the region of residues 582-593; and (5) a HEV-VLP with HIV V3 peptide, or a flu-M2 peptide, or a herpes simplex virus peptide, inserted into the region of residues 601-613.

Example 8

Spatial Configuration of Hepatitis E Virus Antigenic Domain

Hepatitis E virus (HEV) is a human pathogen that causes acute hepatitis. When an HEV capsid protein containing a 52-amino acid deletion at the C-terminus and a-111 amino acid deletion at the N-terminus is expressed in insect cells, the recombinant HEV capsid protein can self-assemble into a T=1 virus-like particle (VLP) that retains the antigenicity of the native HEV virion. In this study, the inventors used cryo-electron microscopy and image reconstruction to show that anti-HEV monoclonal antibodies bind to the protruding domain of the capsid protein at the lateral side of the spikes. Molecular docking of the HEV VLP crystal structure revealed that the Fab224 covered three PORF2 surface loops at the top part of the spike. The inventors also determined the structure of a chimeric HEV VLP and located the inserted B-cell tag, an epitope of 11 amino acids coupled to the C-terminal end of the recombinant ORF2 protein. The binding site of Fab224 appeared distinct from the location of the inserted B-cell tag, suggesting that the chimeric VLP could elicit immunity against both HEV and an inserted foreign epitope. Therefore, the T=1 HEV VLP is a novel delivery system for displaying foreign epitopes at the VLP surface in order to induce antibodies against both HEV and the inserted epitope.

Introduction

Hepatitis E virus (HEV) is a causative agent of acute hepatitis in humans and is primarily transmitted via the fecal-oral route. HEV is thus resistant to the low pH and digestive enzymes associated with the stomach and gastrointestinal tract. HEV regularly causes epidemics in many tropical and subtropical countries. In India, 101 outbreaks were confirmed by serological analysis in the state of Maharashtra in the last 5 years (Deshmukh et al., 2007, Vaccine 25:4350-4360), and in India, the lifetime risk of HEV infection exceeds 60% (Worm and Wirnsberger, 2004, Drugs 64:1517-1531). Sporadic cases have also been reported in HEV-endemic regions, as well as in non-endemic areas. Although some of these cases were associated with travel, many cases involved patients without history of travel to HEV endemic regions. Accumulating evidence suggests that sporadic infection occurs through a zoonotic route and is not limited to developing countries. Seroprevalence suggests hepatitis E infection may also be prevalent in the United States (Minuk et al., 2007, CAn J Gastroenterol. 21:439-442), France (Bendall et al., 2008. J Med Virol 80:95-101), and Japan (Mushahwar, 2008, J Med Virol 80:646-658). The overall mortality rate of HEV infection during an outbreak generally ranges from 1 to 15% and the highest mortality occurs in pregnant women, with fatality rates of up to 30% (Naik et al., 1992, Bull World Health Organ 70:597-604).

The HEV virion is composed of a 7.2 kB single-stranded RNA molecule and a 32-34 nm icosahedral capsid. The HEV genome contains three open reading frames (ORFs). The capsid protein, encoded by the second open reading frame (ORF2) located at the 3' terminus of the genome, comprises 660 amino acids and is responsible for most capsid-related functions, such as assembly, host interaction, and immunogenicity. Recombinant ORF2 proteins can induce antibodies that block HEV infection in non-human primates (Li et al., 2004, Vaccine 22:370-377; Tsarev et al., 1997, Vaccine 15:1834-1838). Four major antigenic domains were predicted to be located within the C-terminal 268 amino acids of ORF2 protein, one domain was experimentally identified as a neutralization epitope in the Sar-55 ORF2 capsid protein (Schofield, et al., 2000, J Virol 74:5548-5555; Schofield et al., 2003, Vaccine 22:257-267). However, the minimal peptide needed to induce anti-HEV neutralizing antibodies contains residues 459-607 of the ORF2 protein (Zhou et al., 2005, Vaccine 23:3157-3165), which is much longer than a linear antigenic epitope, suggesting that the neutralization epitope is conformational. Therefore, the detailed structure of HEV capsid protein is required in order to understand the organization of HEV epitopes.

Currently, there are 1,600 HEV genomic sequences available through the International Nucleotide Sequence Database Collaboration. They are classified into four genotypes, which vary by geographic distribution and host range (Khuroo et al., 2008, Curr Opin Infect Dis 21:539-543). In contrast, only a single serotype has been identified, suggesting that the immuno-dominant domain of HEV is highly conserved among genotypes. Antibodies from any one of the four genotypes cross-react with the capsid protein of genotype-1 (Emerson et al., 2006, J Gen Virol 87:697-704).

Like other hepatitis viruses, HEV does not propagate well in currently available cell culture systems. Hepatitis E preventive strategies so far rely on the use of ORF2-derived recombinant protein (Maloney et al., 2005, Vaccine 23:1870-1874). When expressed in insect cells, truncated recombinant ORF2 protein (PORF2) with 52 residues deleted from the C-terminus and 111 residues deleted from the N-terminus, self-assembles into virus-like particles (VLPs) (Li et al., 1997, J Virol 71:7207-7213). The inventors' previous structural analysis of recombinant HEV VLP by cryo-electron microscopy (cryo-EM) provided the first understanding of the quaternary arrangement of PORF2.

The essential assembly element of PORF2 protein contained amino acids 125-600 (Li et al., 2005, J. Virol. 79:12999-13006) and the reconstructed VLP displayed a T=1 icosahedral particle composed of 60 copies of truncated PORF2 (Xing et al., 1999, Virology 265:35-45). Recently, crystal structures were reported for genotype-1 T=1 VLP (Xing et al., 2010, J Biol Chem 285:33175-33183), genotype-3 T=1 VLP (Yamashita et al., 2009, Proc Natl Acad Sci USA 106:12986-12991), and genotype-4 T=1 VLP (Guu et al., 2009, Proc Natl Acad Sci USA 106:12992-12997), revealing that PORF2 is composed of three domains: S-domain, M-domain and P domain. The T=1 icosahedral shell is composed of 60 copies of S-domains, while the M-domain binds tightly to the S-domain and interacts with two threefold-related M-domains to form a surface plateau at each of the three-fold axes. Two P domains are tightly associated as a dimeric-spike that protrudes from each of the icosahedral twofold axes. As a result, on a low resolution cryo-EM density map, the HEV T=1 VLP appears as an icosahedral particle with 30 spikes (Xing et al., 1999, supra).

Although these VLPs are smaller (270 Å in diameter) than the native HEV virion (320-340 Å), oral administration of HEV VLPs to experimental animals can induce anti-HEV antibodies that bind to native HEV (Li et al., 2001, Vaccine 19:3476-3484). When a B-cell tag of 11 amino acids on glycoprotein D of herpes simplex virus was covalently coupled to the C-terminal end of PORF2 (after residue 608), the fusion protein retained the ability of PORF2 to assembly and form chimeric T=1 icosahedral VLP that were capable of eliciting systemic and mucosal antibodies against both HEV capsid protein and the attached B-cell tag (Niikura et al., 2002, Virology 293:273-280). Therefore, the HEV T=1 VLP is a potential carrier for delivering not only HEV antigen but also foreign antigens or anti-viral drugs to the host immune system. However, rational design of HEV-based delivery vectors requires detailed information on HEV VLP structure as well as HEV immunodominant domains.

In this study, the inventors identified antigenic structures using cryo-EM and three-dimensional reconstruction. Our results indicate that the binding footprint of a neutralizing antibody covers the lateral side of the P domain, while a B-cell tag at the C-terminus does not alter the assembly of T=1 HEV VLP.

Materials and Methods

Production and Purification of Anti-HEV Monoclonal Antibody Mab224

Eight-week-old female BALB/c mice were immunized at 0 and 4 weeks by intraperitoneal inoculation with HEV VLPs (100 ug/ml). Four weeks later, a final boost containing an equal volume of antigen was administered. Three days after the final boost, mouse spleen cells were fused with P3U1 mouse myeloma cells using polyethylene glycol 1500 (50% [w/v]) (Boehringer, Mannheim, Germany) essentially as described by Adler and Faine (Adler and Faine, 1983, Pathology 15:247-250). Supernatants from microplate wells positive for hybridoma growth were screened by ELISA using recombinant HEV VLPs as the antigen. Hybridomas that secrete antibodies specific for HEV were subcloned three times by limiting dilution, after which they were considered to be monoclonal. Antibodies in the supernatants were isotyped using the Mouse Monoclonal Antibody Isotyping kit (Amersham, Little Chalfont, Buckinghamshire, U.K.) in accordance with the manufacturer's protocol. Hybridomas were grown in bulk in stationary flasks (Nunc, Roskilde, Denmark) using RPMI-1640 with 15% FCS. Antibodies were purified from cell supernatants using HiTrap protein G affinity columns (Pharmacia Biotech AB, Uppsala, Sweden) and stored at −80° C. Among all of the antibodies that were generated, Mab224, an immunoglobulin G1 (IgG1) isotype was chosen for structural analysis.

Preparation of Fab224 Fragments

Isolated Fab224 fragments were prepared from purified mouse monoclonal antibodies by papain cleavage. A reducing L-cysteine buffer was used to activate the papain, and MAb224 was mixed with papain at a molar ratio of 100:1. The mixture was incubated overnight at 30° C. The reaction was stopped by the addition of iodocetamide, and the product was analyzed by SDS-PAGE. The Fab224 fragments were purified using a 5-ml pre-packed Protein-A chromatography column (Pierce Protein Research) according to the manufacturer's instructions. The Fc fragments and un-cleaved MAbs224 were trapped in the column due to their affinity for protein-A, while the Fab224 fragments were collected in the flow-through fraction.

Production and Purification of Anti-HEV Fab4

The Fab4 was prepared by phage display and purified according to the protocol described previously (Schofield, et al., 2000, J Virol 74:5548-5555). Briefly, chimpanzee 1441 was infected with HEV strain SAR-55. Bone marrow was aspirated from the iliac crest of this animal and antibody κ-chain gene and γ1-chain gene were amplified and cloned into pComb3H phage display vector and pGEM-T cloning vector (Promega) respectively, and transformed into *E coli* XL-1 Blue. The bacteria were then amplified and infected with helper phage VCS M13 at multiplicity of infection of 50 to produce a library displayed on surfaces of phage particles. Phage was panned on SAR-55 ORF2-coated ELISA wells; four rounds of panning were performed. After amplification of the selected library, the phagemid DNA was extracted and the vector was modified to remove the bacteriophage coat protein III-encoding region of the phage. The phagemid DNAs were religated and transformed into *E coli* XL-1 Blue to produce soluble Fabs. The vector pComb3H was constructed to encode a six-histidine tail at the end of the Fab fragment, thus facilitating Fab purification. Fab4 purity was determined by SDS-PAGE, followed by colloidal Coomassie brilliant blue staining Production and Purification of HEV VLPs The production and purification of HEV VLPs were conducted as described (Li et al., 2005, J. Virol. 79:12999-13006; Li et al., 1997, J Virol 71:7207-7213; Niikura et al., 2002, Virology 293:273-280; Xing et al., 1999, Virology 265:35-45). Briefly, DNA fragments encoding the N-truncated ORF2 protein (for wild type VLPs) and the chimeric ORF2 protein (for VLPs/C-tag) were cloned using the baculovirus transfer vector pVL1393 to yield pVLORF2. Insect Sf9 cells (Riken Cell Bank, Tsukuba, Japan) were used to produce recombinant baculovirus. Tn5 insect cells were infected with the recombinant baculoviruses at a multiplicity of infection of 5 and incubated in EX-CELL™ 405 medium (JRH Biosciences, Lenexa, Kans.) for 6 days at 26.5° C. The supernatant was collected after removal of cell debris by centrifugation at 10,000 g for 90 min. The HEV VLPs were pelleted at 100,000 g for 2 h in a Beckman SW32 Ti rotor and resuspended in 4.5 ml EX-CELL™ 405. The VLPs were further purified by centrifugation through a CsCl density gradient (1.31 g/ml) at 110,000g for 24 h at 4° C. in a Beckman SW55Ti rotor. The white virus band was collected and diluted 4 times with EX-CELL™ 405 to decrease the CsCl concentration, and then the VLPs were centrifuged for 2 h in a Beckman TLA 55 rotor at 100,000 g. The VLPs were resuspended in 100-500 µl of 10 mM potassium-MES buffer (pH=6.2) and stored at 4° C. To construct chimeric VLPs/C-tag, recombinant baculoviruses were prepared by inserting the B-cell tag epitope from herpes simplex virus glycoprotein D (QPELAPEDPED) at amino-acid position 608 (Niikura et al., 2002, supra).

Western Blotting

A series of DNA fragments were constructed to encode truncated ORF2 residues 112-660, 112-608, 112-602, and 112-601, 112-600, 112-596, and 112-589, respectively. These recombinant ORF2 genes were inserted into a baculovirus vector and expressed in insect cells using the protocol for VLP production, except that the recombinant proteins were recovered from cytoplasm after lysis of the cell. Recombinant proteins were heated in 4× Laemelli sample buffer and electrophoresed under reducing conditions in a 10% SDS-polyacrylamide gel. After transfer of proteins to a PVDF membrane, the membrane was blocked with TBS buffer (20 mM Tris, pH=7.6, NaCl) containing 0.5% Tween-20 (v/v) prior to overnight incubation with Fab224 fragments at a 1:10 dilution. After extensive wash with TBS buffer containing 0.05% Tween-20 (v/v), alkaline-phosphatase conjugated anti-mouse IgG (Fab specific) was incubated with membrane for 1 hour at room temperature. The blot was then washed and developed with the NBT-BCIP reaction.

Preparation of VLP-Fab Complexes for Cryo-electron Microscopy

The VLP/Fab complexes were prepared by incubating Fabs with VLPs at a molar ratio exceeding 1:300 (VLP vs Fabs) at 4° C. overnight. To reduce the background density in the subsequent structural determination, highly pure VLP/Fab complexes were obtained using a short column containing Sephacryl-300, which resulted in the removal of the unbound Fab from the sample. The fractions containing VLP/Fab complexes were collected based on their optical density readings at a wavelength of 280 nm. The Fab binding occupancy was roughly estimated by performing SDS-PAGE (gradient 8-25%) on the purified VLP/Fab complexes at a constant voltage using the Phast™ system (Pharmacia). The particle morphology of VLP/Fab complexes was examined by negative stain electron microscopy (EM) using 2% uranyl acetate.

Cryo-electron Microscopy

Sample preparation and cryo-EM were performed following previously described, wellestablished procedures (Li et al., 2005, J. Virol. 79:12999-13006; Xing et al., 1999, Virology 265:35-45). Briefly, a drop containing 3.5 µl of the sample was applied to a glow-discharged holey-carbon coated copper grid, blotted with a piece of filter paper for 3 s to remove the extra liquid and quickly plunged into liquid ethane cooled by liquid nitrogen. Samples were frozen in a thin layer of vitrified ice. The grid was then transferred into a Gatan 626DH cryo-holder and kept at a low temperature (−178° C.) during the subsequent data collection. Micrographs were collected under a low-dose condition (<10 e-/Å2) using Kodak SO163 film at a magnification of 45,000× on a FEI CM-120 electron microscope operated at 120 kV, and particles were photographed at a defocus range from 1000 to 3000 nm. Micrographs were visually inspected and selected based on a suitable particle concentration, optimal ice thickness, and minimal specimen drift. Only micrographs fulfilling these criteria were analyzed.

Image Processing

Selected micrographs were digitized using a Heidelberg Prime scanner D8200 (Heidelberg, Germany) at a 14 µm scanning step size, corresponding to 3.11 Å per pixel of specimen space. Particles were manually picked and centered by cross-correlating each one against the circular average image. The astigmatism and defocus value were evaluated by the superimposed power spectra from all particles within a single micrograph. The CTF first zero was approximately within the range of 17-20 Å$^{-1}$ for the data used for the structural determination. The self-common-lines algorithm (Crowther, 1971, Philos Trans R Soc Lond B Biol Sci 261: 221-230) was used to yield the initial models for VLP/C-tag, VLP/Fab4, and VLP/Fab224. The origins and orientations search for each particle was carried out iteratively using the polar Fourier transformation (PFT) algorithm running on an AMD MP1800 MHz dual-processor Linux workstation (Baker and Cheng, 1996, J. Struct. Biol. 116:120-130). Three-dimensional reconstructions were computed by combining a set of particles with orientations that spread evenly in an icosahedral asymmetric unit using the Fourier-Bessel algorithm and by superimposing 5-3-2 icosahedral symmetry. To examine the reliability of the three-dimensional reconstruction, the dataset was evenly divided into two parts at the final refinement step and two three-dimensional reconstructions were computed. The resolution was estimated using Fourier shell correlation (FSC) by assessing the agreement between these two reconstructions in Fourier space. Using a coefficient value of 0.5 as the criteria, the estimated resolution of the three-dimensional reconstructions of VLP/C-tag, VLP/Fab224 and VLP/Fab4 were computed as 17.5 Å, 18.5 Å and 24 Å, respectively.

The three-dimensional reconstructions were rendered and visualized using the Chimera program (Pettersen et al., 2004, J Comput Chem. 25:1605-1612). The contour level was chosen at a value corresponding to 100% of the mass of the PORF2 protein. The electron density map was displayed in the isosurface mode, which builds a barrier to contour the density about a certain threshold.

Fitting the Crystal Structure into Cryo-EM Density Maps

Density of the bound Fab molecule was determined from a difference density map, which was calculated by subtracting the cryo-EM map of unbound HEV T=1 VLP from the density map of the Fab-VLP complex. The cryo-EM map of unbound HEV VLP was published previously (Xing et al., 1999, Virology 265:35-45). Because the cryo-EM data of unbound VLP and Fab-VLP complex were collected with the same FEI CM-120 electron microscope under similar imaging conditions, the difference density map was calculated by direct subtraction of the density of unbound VLP from the reconstruction of Fab-VLP complex after normalizing the contrast between the two maps. The calculated difference map was used as constraint in model fitting. Manual fitting was carried out by translational and rotational movement of the three-dimensional crystal structure of PORF2 protein (PDB code: 2ZZQ) (Xing et al., 2010, J Biol Chem 285:33175-33183) into the cryo-EM density maps using program O (Jones et al., 1991, Acta crystallogr. Sect. A 47:110-119). To obtain the best fit, the atomic model of the PORF2 subunit was treated as a rigid body. The fitting was first manually refined by minimizing the crashes between symmetry-related PORF2 molecules and then evaluated based on the cross correlation coefficient (cc value) between the cryo-EM density and the density computed from the fitted PORF2 coordinates. Fitting was halted when the cc value reached 80%. The figures were prepared using the program PyMOL (DeLano, 2002, The PYMOL molecular graphics system. DeLano Scientific, Palo Alto, Calif., USA), and the surface stereographic projection of the HEV VLP was prepared using the program RIVEM (Xiao and Rossmann, 2007, J Struct. Biol. 158:181-186).

Results

Binding of Antibody Mab224 to PORF2

Figure 35:
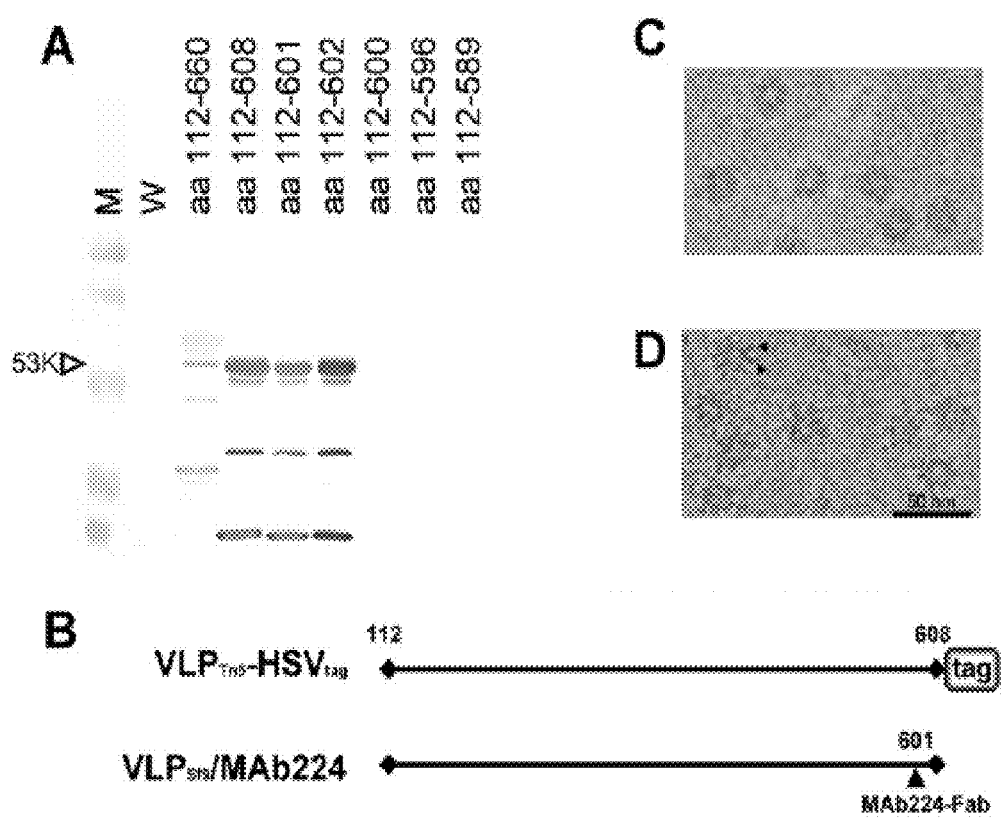
FIG. 35: Characterization of VLP/C-tag and VLP/Fab224. (A) Western blotting assay of the C terminally truncated ORF2 proteins with Fab224. M: molecular weight markers; W: peptides recovered from baculovirus-infected cells. (B) Diagram of the C-terminal markers. (C) Electron micrograph of frozen-hydrated VLP/C-tag and (D) micrograph of frozen-hydrated VLP/Fab224. Black arrows indicate the Fab molecules attached to the VLP. Both particles showed an absence of density in the center. Note the surface spike in VLP/Fab224 appeared as longer thorn-like densities compared to VLP/C-tag. Scale bar presents 50 nm.

Binding of the monoclonal antibody Fab224 to PORF2 was examined via immunoblot analysis. A series of recombinant ORF2 proteins with C-terminal truncations were separated by SDS-PAGE on a 10% gel under reducing conditions and blotted with Fab224 (FIG. 35A). Fab224 recognized both reduced and denatured recombinant ORF2 proteins that contained amino acids 112-660, 112-608, 112-602, and 112-601. In contrast, recombinant ORF2 proteins composed of residues 112-600, 112-596, and 112-589 did not bind to Fab224. These data indicate that residues 597-601 are critical for Fab224 binding to PORF2. Because the recombinant ORF2 proteins were recovered from cell cytoplasm where multiple forms of PORF2 were reported (Li et al., 1997, J Virol 71:7207-7213), the positive bands observed at low molecular weight may be the proteolytic products or degraded forms of ORF2 that contain the Fab224 binding sequence.

Two-dimensional Electron Cryo-micrographs

The chimeric VLPs (FIG. 35C) and the Fab224-conjugated VLP complex (FIG. 35D) showed circular profiles with spike-like densities that extended from the surface. As observed previously (Li et al., 1997, supra; Xing et al., 1999, Virology 265:35-45), they appeared to have a white contrast center, indicating that they are empty particles lacking RNA (data not shown). The sizes of both VLPs were approximately 27 nm without taking into account the extra densities that extended from the VLP/Fab224 surface (FIG. 35D).

Binding Site of Antibodies

Figure 36:
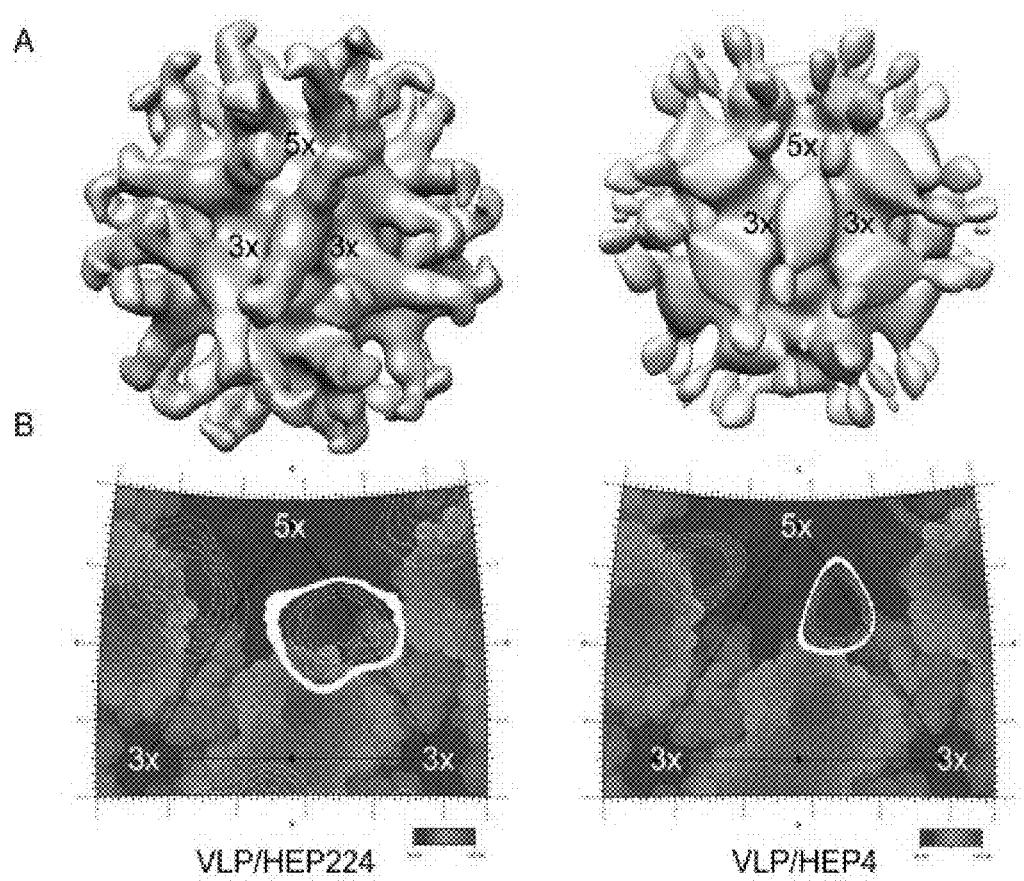
FIG. 36: The cryo-EM structure of HEV T=1 VLP in complex with anti-HEV antibodies. (A) Surface presentation of VLP/Fab224 (left) and that of VLP/Fab4 (right) viewed along one of the icosahedral twofold axes. One fivefold axis and two adjacent threefold axes are marked with the corresponding number. In both reconstructions, 60 copies of Fab are attached to the lateral side of HEV VLP; however, the density of Fab4 molecule appears weaker than that of Fab224 molecule. (B) The viral surface is shown as a stereographic projection overlapped with a line drawing an icosahedral asymmetric unit. The fivefold, threefold and twofold axes are marked with corresponding numbers, while the black triangle encloses the area of an icosahedral asymmetric unit. The surface residues are colored according to the distance from the center of the VLP, with red being the furthest away and blue representing the surface depressions. The Fab density is projected as white circles on the viral surface and the most outer density-layer was drawn as thick white circles.

The cryo-EM structure of HEV/Fab224 was reconstructed from 615 images of individual particles and displayed T=1 icosahedral symmetry with 60 protein subunits that were arranged into 30 dimeric protruding spikes located at each icosahedral two-fold axis (FIG. 36A). Sixty Fab molecules were observed around each VLP particle, bound to the shoulder of the P domain. The Fab density extended ~57 Å radially away from the spike surface. The density corresponding to the Fab was approximately equal in magnitude to that of the HEV VLP, indicating that most or all of the 60 binding sites were occupied by a Fab molecule. The density corresponding to the VLP capsid was removed from the cryo-EM map, producing a Fab differential density map that was used to pinpoint the binding site of the Fab224 antibody (FIGS. 37A and 37B).

In addition, the structure of HEV VLP in complex with the neutralizing antibody Fab4 was determined by combining 264 individual images. Fab4 precipitates both the native HEV virion and recombinant PORF2 peptides but the reaction depends on the presence of amino acids 597-607 (Schofield et al., 2003, Vaccine 22:257-267). Three-dimensional reconstruction of the VLP/Fab4 complex showed 60 Fab molecules bound to each HEV VLP. Unlike the Fab224 VLP complex, the density corresponding to Fab4 was about one third of that of the capsid (FIG. 36A), suggesting that only 30-40% of the binding sites were occupied by the Fab. Moreover, the binding of Fab4 appeared deeper on the side-wall of the protruding domain towards the capsid shell, leaving its Fc domain exposed above the surface of the plateau (FIG. 36A). In contrast, the entire Fab224 stood mainly on the top of the P domain surface. The Fab224 and the Fab4 extend along the long axis of the P domain. In both cases, no steric hindrance of the Fab on the P domain with the neighboring Fab molecules at either the five-fold or the three-fold axes was apparent. The orientation of the Fab relative to the plateau appeared different at a radius of 135 Å. The long axis of Fab224 tilted toward the neighboring spike, while the long axis of Fab4 pointed to the fivefold axis (FIG. 36A).

To further analyze the Fab and HEV VLP binding interface, the crystal structure of genotype-1 PORF2 was docked onto the VLP/Fab224 cryo-EM density map. The genotype-1 PORF2 crystal structure (2ZZQ) is composed of three domains (Xing et al., 2010, J Biol Chem 285:33175-33183), and these domains are in good agreement with those of genotype-3 and genotype-4 PORF2 (PDB accession number 2ZTN and 3HAG, respectively) (Guu et al., 2009, supra; Yamashita et al., 2009, Proc Natl Acad Sci USA 106:12986-12991). The coordinates fitted very well with the cryo-EM density map without any adjustment (CC value=80%). The atoms on the surface of the HEV VLP capsid were plotted and colored according to their radial distance, and overlapped with the density of the Fab at the surface plateau of the protruding spike (FIG. 36B).

Figure 37:
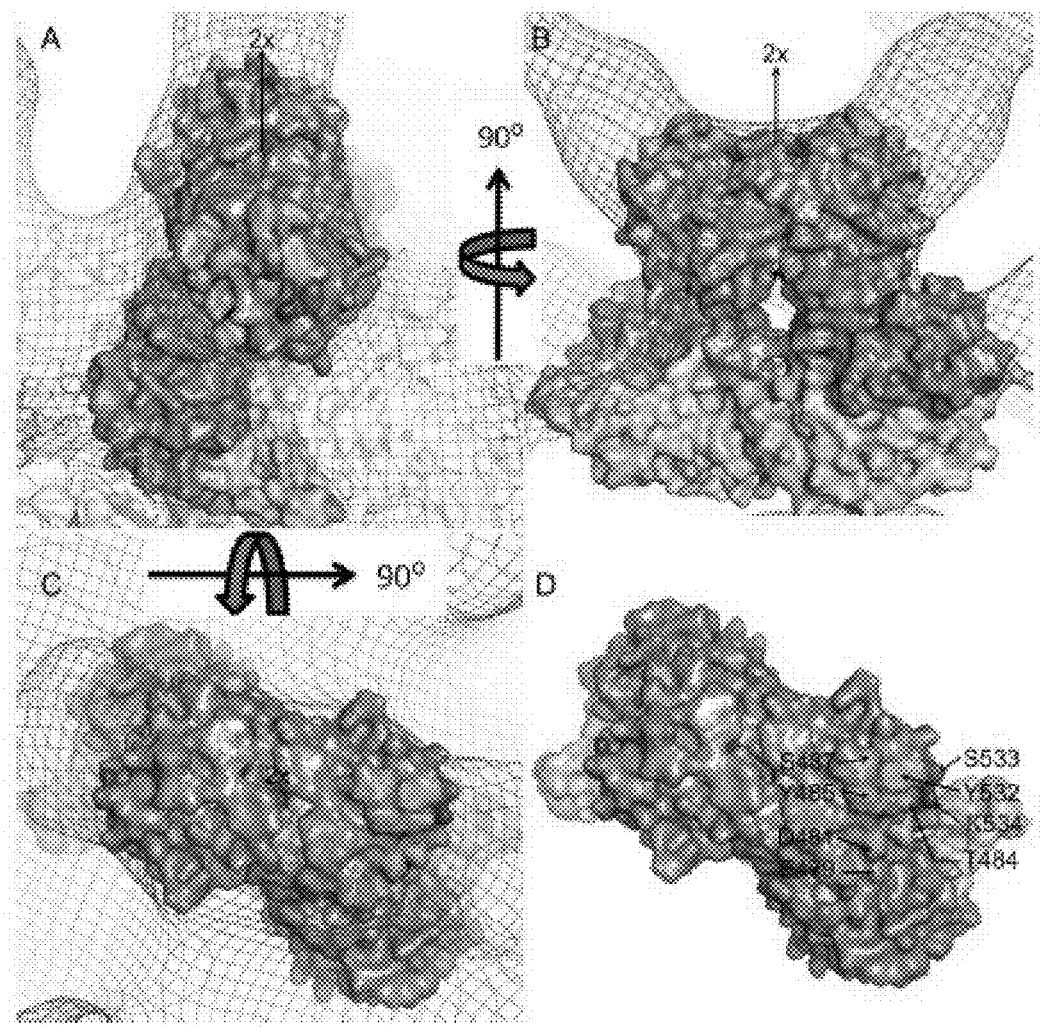
FIG. 37: The binding site of Fab224 antibody. (A) The cryo-EM density map of VLP/Fab224 was fitted with the crystal structure of PORF2 and viewed along a bound Fab molecule. One PORF2 dimer is presented as solid surface and colored as light magenta for S-domain, slate for M-domain and dark grey for P-domain. The neighboring dimers are drawn as ribbon mode and colored wheat. (B) The side view of a PORF2 dimer fitted into the cryo-EM density map. (C) A PORF2 dimer viewed along the twofold axis overlapped with the cryo-EM density map. (D) The top view of a PORF2 dimer viewed along the twofold axis. The amino acids in PORF2 responsible for binding to Fab224 are labeled. The PORF2 dimer is presented as solid surfaceand colored in gray, slate, light magenta for the P domain, the M-domain and the S-domain, respectively. The residues along the Fab binding interface are colored according to the element with green for carbon, blue for nitrogen and red for oxygen.

The Fab224 interacted with the residues at the side of the ORF2 spike rather than with those residues on the spike plateau surface (FIG. 37C). The contact footprint did not overlap with the dimeric interface of the PORF2 spike. As expected, Fab224 recognizes a conformational epitopes and its binding site covers a surface composed of three loops including amino acids 470-493 in loop 1, amino acids 539-569 in loop 2, and amino acids 581-595 in loop 3 (FIG. 37D). Residues E479, D481, T484, Y485, and S487 from the AB loop and residues Y532, S533, and K534 from the CD loop were in close contact with the Fab molecule.

Structure of HEV Chimeric VLP

Figure 38:
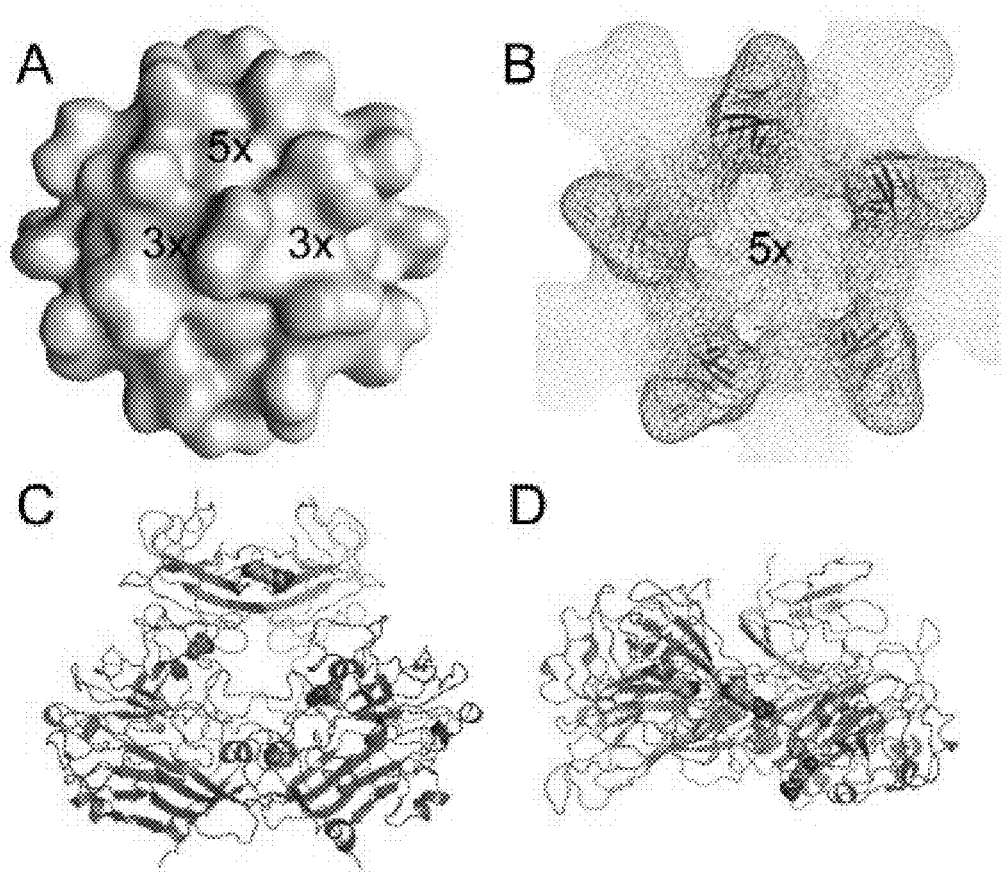
FIG. 38: The structure of the chimeric HEV VLP carrying a B-cell tag. (A) Surface presentation of VLP/C-tag viewed along an icosahedral twofold axis. (B) The cryo-EM density map of VLP/C-tag (mesh) was fitted with the crystal structure of PORF2 decamer (Ribbon). (C) Ribbon representation of PORF2 dimer with one monomer colored as gray and the other colored as pink for 51 domain, blue for M-domain and lime for the P domain. The amino acids prior to the four internal insertion sites are marked in sphere mode with color code representing the element. (D) The top view of the PORF2 dimer showing the location of the non-VLP insertion sites.

Chimeric HEV VLP/C-tag was constructed using a PORF2 fusion protein in which a B-cell tag of 11 amino acids was incorporated into the C-terminus of PORF2 (FIG. 35B). A total of 782 images of individual particles were used to reconstruct the final three-dimensional model of VLP/C-tag. In agreement with the previously published cryo-EM VLP structures, the surface of VLP/C-tag can also be divided into two distinct layers, an icosahedral shell and a protruding spike (FIG. 38A). The spike projects outward from the icosahedral shell and is composed of a PORF2 dimer. The distance between two adjacent spikes was ~76 Å as measured between the centers of surface plateau. These results are consistent with the measurements of VLPs obtained either from Tn5 insect cells (Xing et al., 1999, Virology 265:35-45) or from Sf9 insect cells (Li et al., 2005, J. Virol. 79:12999-13006) and no detectable density was added onto the outer surface of the spike. No RNA density was detected within the chimeric VLP/C-tag.

Figure 39:
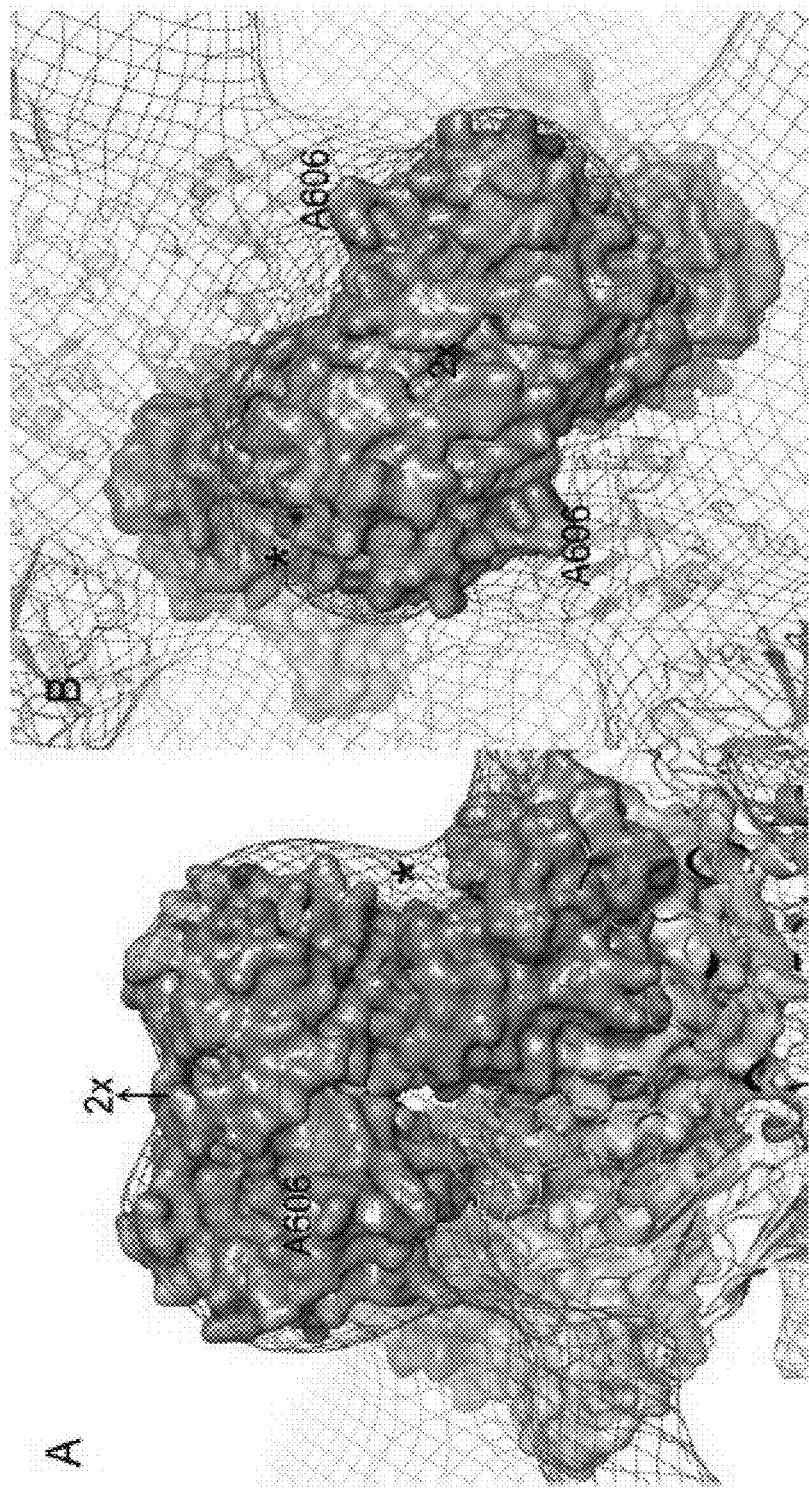
FIG. 39: Fitting of the PORF2 structure into the cryo-EM density map of HEV VLP/C-tag. The side view (A) and the top view (B) of the fitted PORF2 dimer (surface presentation) overlapped with the cryo-EM density map of VLP/C-tag (mesh). The C-terminal residue A606 is located at the side of the protruding spike. One PORF2 dimer is colored as light magenta, slate, and gray for the S-, M- and P-domain on the surface presentation, respectively. The ribbon representation shows the adjacent dimers. The amino acids in PORF2 responsible for binding to Fab224 were colored in green for carbon, blue for nitrogen, and red for oxygen. Asterisks mark the location of the extra density that was not occupied with PORF2 coordinates.

The crystal structure fit very well within the VLP/C-tag density map (FIG. 38B), indicating that the C-terminal 11 amino acids insertion inhibits neither the dimer-dimer interactions nor the formation of T=1 VLP. When the density maps were contoured to cover 100%, the radii of the S domains were roughly the same for both the VLP/C-tag and the VLP/Fab224 maps, and the height of the protruding spikes appeared similar. Density difference was not observed from the docking (FIG. 39), suggesting that the inserted B-cell tag is flexible and less ordered. However, model fitting revealed that coordinates-unoccupied density appeared at the lateral side of the spike and underneath the Fab224 binding site (FIGS. 39A and 39B), which may correspond to the inserted peptide.

Discussion

HEV T=1 VLP is a vaccine candidate that induces protective immunity in non-human primates (Li et al., 2004, Vaccine 22:370-377). It can also be used as an antigen carrier to deliver foreign epitopes through oral administration (Niikura et al., 2002, Virology 293:273-280). Therefore, structural analysis of the antibody recognition sites is essential to suppress the neutralization effect of host vector-specific antibodies. For this purpose, the inventors determined the structure of HEV VLP in complex with antibodies Fab224 (VLP/Fab224), Fab4 (VLP/Fab4), and the structure of chimeric HEV VLP carrying a B-cell tag at the C-terminus of PORF2 (VLP/C-tag). Docking the PORF2 crystal structure provides spatial information on the HEV antigenic domain and structural guidance to better design foreign epitope insertion.

Structure of the Neutralization Epitopes

The antigenic properties of HEV and the mechanisms by which it is neutralized are difficult to characterize due to the lack of adequate cell culture replication systems. Therefore, our understanding of HEV immunology is mainly based on studies using recombinant proteins expressed in E. coli (Riddell et al., 2000, J Virol 74:8011-8017) and recombinant proteins or HEV VLPs generated using the baculovirus expression systems (Li et al., 1997, J Virol 71:7207-7213; Robinson et al., 1998, Protein Expr Purif 12:75-84). Data from these studies indicates that the C-terminal region of PORF2 participates in the immune response against HEV and that the HEV neutralization epitope is conformational. The minimum peptide required to induce HEV neutralizing antibodies corresponds to a region of 148 residues in PORF2, from amino acids 459-607 (Zhou et al., 2005, Vaccine 23:3157-3165). This peptide coincides with the P-domain revealed in the crystal structures of PORF2. The density of the Fab in our cryo-EM structure interfaced entirely with the spikes, thus confirming that the P domain is primarily responsible for HEV antigenicity. Fab4 is a chimpanzee antibody that recognizes ORF2 protein and was isolated using phage display from a cDNA library (Schofield, et al., 2000, J Virol 74:5548-5555). Fab4 binds to native HEV virions and recombinant PORF2 peptides containing amino acids 597-607 (Schofield et al., 2003, Vaccine 22:257-267). The inventors performed fitting with the VLP/Fab4 structure; however, the Fab4 density was too weak to conclusively determine the Fab4 binding site on the surface of HEV VLP. However, the density corresponding to the Fab4 molecule did cover amino acid 606 (data not shown). It is not clear why Fab224 appeared not to interact with peptides lacking amino acids 599-608 in immunoblot analysis. However, the Fab224 binding site is consistent with the critical antigenic residues determined previously using mutagenesis. It was found that double mutations that changed residues E479 and K534 or Y485 and 1529 to alanine selectively abrogated PORF2 reactivity with neutralizing antibodies (Li et al., 2009, PLos Pathog. 5:e1000537). Another set of mutants defined the same region as the HEV antigenic domain, with antibody recognition residues spreading over the AB, CD and EF loops (Yamashita et al., 2009, Proc Natl Acad Sci USA 106:12986-12991). The antibodies used in both experiments were neutralizing antibodies; therefore, the Fab224 binding surface is part of the dominant neutralization site, suggesting that the monoclonal antibody Fab224 is a neutralizing antibody. This neutralization site partially overlaps with the receptor binding site (Yamashita et al., 2009, supra), and antibody binding may create spatial hindrance that prevents HEV VLPs from attaching to the cell surface.

Insertion Sites for Foreign Epitopes

Because they are highly organized capsids that mimic the overall structure of virus particles, VLPs are a robust means by which to simultaneously carry small molecules, peptide antigenic epitopes, and DNA vaccines from heterogeneous sources to target disease sites. However, this rational vaccine design relies on excellent VLP structural information so that epitopes can be effectively conjugated to the VLP surface. In previous study, rather than selecting PORF2 insertion sites on the basis of structural information, six insertion sites were selected according to restriction enzyme sites located either internally (four sites) or in the N- or C-terminus of PORF2. The internal sites are located after residues A179, R366, A507, and R542. Fusion proteins carrying insertions at sites A179 and R336 failed completely to produce VLPs, and insertions at A507 and R542 greatly reduced VLP production (Niikura et al., 2002, supra). Crystal structure data revealed that the spatial position of these sites is disadvantageous. Residue A179 is located in the S domain in the middle of a α-helix, which is necessary for the integrity of the S domain and its interaction with the twofold related neighboring subunit. R366 is located in the M-domain and favors electrostatic interaction with residue E386 from the threefold related neighboring subunit. Although located within the P domain, the side chain of R542 is within the dimeric interface and guides the hydrophobic interaction of the two monomers. Replacement of R542 may misalign the orientation between two P domains and weaken the dimeric interaction between PORF2 proteins. Residue A507 in the P-domain plays an important role in maintaining P domain orientation by fixing the angle of the long proline-rich hinge. Moreover, none of the four residues are exposed on the surface of VLPs, although some of them are located on the surface of individual PORF2 subunits (FIGS. 38C and 38D). Therefore, insertion of a foreign sequence at these sites does not interfere with the expression of individual proteins but rather hinders the assembly of HEV VLPs. The crystal structure revealed that the C-terminus is exposed on the surface of VLPs, while the N-terminus points toward the VLP center. Therefore, insertion at these two sites does not inhibit VLP assembly; however, the C-terminus is more suitable for tethering bulky foreign antigenic sequences, as was shown in a previous report (Niikura et al., 2002, supra).

The cryo-EM structure of the chimeric HEV VLP/C-tag suggested that the B-cell tag was located at the lateral side of the spike, not far from residue A606 (C-terminal end in the crystal structure) (FIG. 39A). This density is located beneath the Fab224 binding site but nonetheless overlaps with the potential binding site of Fab4. As a result, insertion of the 11 amino acid B-cell sequence may partially leave the HEV antigenic site open and accessible to the host immune system. This explains why mice can develop antibodies against both HEV and the foreign epitope after VLP/C-tag oral administration (Niikura et al., 2002, supra).

In conclusion, the cryo-EM structures of VLP/Fab224 identified the lateral surface of the P domain as the recognition site for anti-HEV neutralizing antibodies. Insertion of a B-cell epitope at the PORF2 C-terminus does not interfere with T=1 VLP assembly. Thus, T=1 HEV VLPs are a novel tool for oral vaccine delivery, as they constitute a non-replicating entities that can induce mucosal immunity without adjuvant. Induction of antibodies against both HEV and the target disease is an additional advantage of this delivery system.

All patents, patent applications, and other publications, including GenBank Accession Numbers, cited in this application are incorporated by reference in the entirety for all purposes.

What is claimed is:

1. A composition comprising:
   an HEV capsid protein comprising a portion of an HEV ORF 2 protein and a heterologous peptide, wherein the heterologous peptide is inserted into the portion of HEV ORF 2 within a pre-selected region corresponding to residues 483-490, residues 530-535, residues 554-561, residues 573-577, or residues 582-593, or residues 601-613 of SEQ ID NO:1; and
   a heterologous nucleic acid encapsulated in a chimeric HEV virus-like particle (VLP) formed by the HEV capsid protein.

2. The composition of claim 1, wherein the heterologous nucleic acid and the heterologous peptide are from the same source.

3. The composition of claim 1, wherein the heterologous nucleic acid and the heterologous peptide are from different sources.

4. The composition of claim 1, wherein the HEV capsid protein comprises a portion of HEV ORF 2 protein and two or more heterologous peptides.

5. The composition of claim 1, wherein the two or more heterologous peptides are from different sources.

6. The composition of claim 1, wherein the two or more heterologous peptides are from the same source.

7. The composition of claim 1, wherein the HEV capsid protein comprises an amino acid sequence corresponding to residues 112-608 of SEQ ID NO:1.

8. The composition of claim 7, wherein the HEV capsid protein further comprises an HEV ORF3 polypeptide corresponding to residues 91-123 of SEQ ID NO:2 fused to the N terminus of an HEV ORF2 polypeptide corresponding to residues 112-608 of SEQ ID NO:1.

9. The composition of claim 7, wherein the HEV capsid protein further comprises an HEV ORF3 polypeptide corresponding to residues 70-123 of SEQ ID NO:2 fused to the N terminus of an HEV ORF2 polypeptide corresponding to residues 112-608 of SEQ ID NO:1.

10. A composition of claim 1, further comprising a pharmaceutically acceptable excipient.

11. A composition of claim 10, wherein the excipient is an adjuvant.

12. A composition of claim 10, wherein the excipient is adapted for oral delivery.

13. A composition of claim 10, wherein the excipient is adapted for mucosal delivery.

14. A method of inducing an immunogenic response in a host, comprising the step of administering the composition of claim 1.

15. An HEV capsid protein, comprising a portion of an HEV ORF 2 protein and a heterologous peptide inserted into the portion of the HEV ORF 2 within a pre-selected region of residues corresponding to residues 483-490, residues 530-535, residues 554-561, residues 573-577, residues 582-593, or residues 601-613 of SEQ ID NO:1, wherein the HEV capsid protein forms an HEV VLP.

16. A polynucleotide encoding the HEV capsid protein of claim 15.

* * * * *

SEQUENCE LISTING

<160> NUMBER OF SEQ ID NOS: 9

<210> SEQ ID NO 1
<211> LENGTH: 660
<212> TYPE: PRT
<213> ORGANISM: Hepatitis E virus
<220> FEATURE:
<223> OTHER INFORMATION: hepatitis E virus (HEV) ORF2 capsid protein

<400> SEQUENCE: 1

```
Met Arg Pro Arg Pro Ile Leu Leu Leu Leu Met Phe Leu Pro Met
 1               5                  10                  15

Leu Pro Ala Pro Pro Gly Gln Pro Ser Gly Arg Arg Gly Arg
             20                  25                  30

Arg Ser Gly Gly Ser Gly Gly Phe Trp Gly Asp Arg Val Asp Ser
             35                  40                  45

Gln Pro Phe Ala Ile Pro Tyr Ile His Pro Thr Asn Pro Phe Ala Pro
 50                  55                  60

Asp Val Thr Ala Ala Ala Gly Ala Gly Pro Arg Val Arg Gln Pro Ala
 65                  70                  75                  80

Arg Pro Leu Gly Ser Ala Trp Arg Asp Gln Ala Gln Arg Pro Ala Val
                 85                  90                  95

Ala Ser Arg Arg Arg Pro Thr Thr Ala Gly Ala Ala Pro Leu Thr Ala
                100                 105                 110

Val Ala Pro Ala His Asp Thr Pro Pro Val Pro Asp Val Asp Ser Arg
            115                 120                 125

Gly Ala Ile Leu Arg Arg Gln Tyr Asn Leu Ser Thr Ser Pro Leu Thr
        130                 135                 140

Ser Ser Val Ala Thr Gly Thr Asn Leu Val Leu Tyr Ala Ala Pro Leu
145                 150                 155                 160

Ser Pro Leu Leu Pro Leu Gln Asp Gly Thr Asn Thr His Ile Met Ala
                165                 170                 175

Thr Glu Ala Ser Asn Tyr Ala Gln Tyr Arg Val Ala Arg Ala Thr Ile
                180                 185                 190

Arg Tyr Arg Pro Leu Val Pro Asn Ala Val Gly Gly Tyr Ala Ile Ser
            195                 200                 205

Ile Ser Phe Trp Pro Gln Thr Thr Thr Thr Pro Thr Ser Val Asp Met
        210                 215                 220

Asn Ser Ile Thr Ser Thr Asp Val Arg Ile Leu Val Gln Pro Gly Ile
225                 230                 235                 240

Ala Ser Glu Leu Val Ile Pro Ser Glu Arg Leu His Tyr Arg Asn Gln
                245                 250                 255

Gly Trp Arg Ser Val Glu Thr Ser Gly Val Ala Glu Glu Ala Thr
                260                 265                 270

Ser Gly Leu Val Met Leu Cys Ile His Gly Ser Leu Val Asn Ser Tyr
            275                 280                 285

Thr Asn Thr Pro Tyr Thr Gly Ala Leu Gly Leu Leu Asp Phe Ala Leu
        290                 295                 300

Glu Leu Glu Phe Arg Asn Leu Thr Pro Gly Asn Thr Asn Thr Arg Val
305                 310                 315                 320

Ser Arg Tyr Ser Ser Thr Ala Arg His Arg Leu Arg Arg Gly Ala Asp
                325                 330                 335

Gly Thr Ala Glu Leu Thr Thr Thr Ala Ala Thr Arg Phe Met Lys Asp
                340                 345                 350

Leu Tyr Phe Thr Ser Thr Asn Gly Val Gly Glu Ile Gly Arg Gly Ile
```

```
                355                 360                 365
Ala Leu Thr Leu Phe Asn Leu Ala Asp Thr Leu Leu Gly Gly Leu Pro
370

```
                50                  55                  60
Ser Gln Ser Pro Ile Phe Ile Gln Pro Thr Pro Ser Pro Pro Met Ser
 65                  70                  75                  80

Pro Leu Arg Pro Gly Leu Asp Leu Val Phe Ala Asn Pro Pro Asp His
                 85                  90                  95

Ser Ala Pro Leu Gly Val Thr Arg Pro Ser Ala Pro Pro Leu Pro His
            100                 105                 110

Val Val Asp Leu Pro Gln Leu Gly Pro Arg Arg
        115                 120

<210> SEQ ID NO 3
<211> LENGTH: 84
<212> TYPE: PRT
<213> ORGANISM: Artificial Sequence
<220> FEATURE:
<223> OTHER INFORMATION: synthetic hepatitis E virus (HEV) ORF2 capsid
      protein C-terminal region, residues 525-608

<400> SEQUENCE: 3

Pro Leu Ser Thr Ile Gln Gln Tyr Ser Lys Thr Phe Phe Val Leu Pro
 1               5                  10                  15

Leu Arg Gly Lys Leu Ser Phe Trp Glu Ala Gly Thr Thr Lys Ala Gly
            20                  25                  30

Tyr Pro Tyr Asn Tyr Asn Thr Thr Ala Ser Asp Gln Leu Leu Val Glu
        35                  40                  45

Asn Ala Ala Gly His Arg Val Ala Ile Ser Thr Tyr Thr Thr Ser Leu
    50                  55                  60

Gly Ala Gly Pro Val Ser Ile Ser Ala Val Ala Val Leu Ala Pro His
 65                  70                  75                  80

Ser Ala Leu Ala

<210> SEQ ID NO 4
<211> LENGTH: 660
<212> TYPE: PRT
<213> ORGANISM: Hepatitis E virus
<220> FEATURE:
<223> OTHER INFORMATION: hepatitis E virus (HEV) ORF2 capsid protein
      genotype 1

<400> SEQUENCE: 4

Met Arg Pro Arg Pro Ile Leu Leu Leu Leu Leu Met Phe Leu Pro Met
 1               5                  10                  15

Leu Pro Ala Pro Pro Gly Gln Pro Ser Gly Arg Arg Arg Gly Arg Arg
            20                  25                  30

Arg Ser Gly Gly Ser Gly Gly Gly Phe Trp Gly Asp Arg Val Asp Ser
        35                  40                  45

Gln Pro Phe Ala Ile Pro Tyr Ile His Pro Thr Asn Pro Phe Ala Pro
    50                  55                  60

Asp Val Thr Ala Ala Ala Gly Ala Gly Pro Arg Val Arg Gln Pro Ala
 65                  70                  75                  80

Arg Pro Leu Gly Ser Ala Trp Arg Asp Gln Ala Gln Arg Pro Ala Val
                 85                  90                  95

Ala Ser Arg Arg Arg Pro Thr Thr Ala Gly Ala Ala Pro Leu Thr Ala
            100                 105                 110

Val Ala Pro Ala His Asp Thr Pro Pro Val Pro Asp Val Asp Ser Arg
        115                 120                 125

Gly Ala Ile Leu Arg Arg Gln Tyr Asn Leu Ser Thr Ser Pro Leu Thr
    130                 135                 140
```

```
Ser Ser Val Ala Thr Gly Thr Asn Leu Val Leu Tyr Ala Ala Pro Leu
145                 150                 155                 160

Ser Pro Leu Leu Pro Leu Gln Asp Gly Thr Asn Thr His Ile Met Ala
            165                 170                 175

Thr Glu Ala Ser Asn Tyr Ala Gln Tyr Arg Val Ala Arg Ala Thr Ile
            180                 185                 190

Arg Tyr Arg Pro Leu Val Pro Asn Ala Val Gly Gly Tyr Ala Ile Ser
            195                 200                 205

Ile Ser Phe Trp Pro Gln Thr Thr Thr Pro Thr Ser Val Asp Met
210                 215                 220

Asn Ser Ile Thr Ser Thr Asp Val Arg Ile Leu Val Gln Pro Gly Ile
225                 230                 235                 240

Ala Ser Glu Leu Val Ile Pro Ser Glu Arg Leu His Tyr Arg Asn Gln
            245                 250                 255

Gly Trp Arg Ser Val Glu Thr Ser Gly Val Ala Glu Glu Ala Thr
            260                 265                 270

Ser Gly Leu Val Met Leu Cys Ile His Gly Ser Pro Val Asn Ser Tyr
            275                 280                 285

Thr Asn Thr Pro Tyr Thr Gly Ala Leu Gly Leu Leu Asp Phe Ala Leu
290                 295                 300

Glu Leu Glu Phe Arg Asn Leu Thr Pro Gly Asn Thr Asn Thr Arg Val
305                 310                 315                 320

Ser Arg Tyr Ser Ser Thr Ala Arg His Arg Leu Arg Arg Gly Ala Asp
            325                 330                 335

Gly Thr Ala Glu Leu Thr Thr Thr Ala Ala Thr Arg Phe Met Lys Asp
            340                 345                 350

Leu Tyr Phe Thr Ser Thr Asn Gly Val Gly Glu Ile Gly Arg Gly Ile
            355                 360                 365

Ala Leu Thr Leu Phe Asn Leu Ala Asp Thr Leu Leu Gly Gly Leu Pro
            370                 375                 380

Thr Glu Leu Ile Ser Ser Ala Gly Gly Gln Leu Phe Tyr Ser Arg Pro
385                 390                 395                 400

Val Val Ser Ala Asn Gly Glu Pro Thr Val Lys Leu Tyr Thr Ser Val
            405                 410                 415

Glu Asn Ala Gln Gln Asp Lys Gly Ile Ala Ile Pro His Asp Ile Asp
            420                 425                 430

Leu Gly Glu Ser Arg Val Val Ile Gln Asp Tyr Asp Asn Gln His Glu
            435                 440                 445

Gln Asp Arg Pro Thr Pro Ser Pro Ala Pro Ser Arg Pro Phe Ser Val
            450                 455                 460

Leu Arg Ala Asn Asp Val Leu Trp Leu Ser Leu Thr Ala Ala Glu Tyr
465                 470                 475                 480

Asp Gln Ser Thr Tyr Gly Ser Ser Thr Gly Pro Val Tyr Val Ser Asp
            485                 490                 495

Ser Val Thr Leu Val Asn Val Ala Thr Gly Ala Gln Ala Val Ala Arg
            500                 505                 510

Ser Leu Asp Trp Thr Lys Val Thr Leu Asp Gly Arg Pro Leu Ser Thr
            515                 520                 525

Ile Gln Gln Tyr Ser Lys Thr Phe Phe Val Leu Pro Leu Arg Gly Lys
            530                 535                 540

Leu Ser Phe Trp Glu Ala Gly Thr Thr Lys Ala Gly Tyr Pro Tyr Asn
545                 550                 555                 560
```

Tyr Asn Thr Thr Ala Ser Asp Gln Leu Leu Val Glu Asn Ala Ala Gly
                565                 570                 575

His Arg Val Ala Ile Ser Thr Tyr Thr Thr Ser Leu Gly Ala Gly Pro
            580                 585                 590

Val Ser Ile Ser Ala Val Ala Val Leu Ala Pro His Ser Ala Leu Ala
            595                 600                 605

Leu Leu Glu Asp Thr Leu Asp Tyr Pro Ala Arg Ala His Thr Phe Asp
    610                 615                 620

Asp Phe Cys Pro Glu Cys Arg Pro Leu Gly Leu Gln Gly Cys Ala Phe
625                 630                 635                 640

Gln Ser Thr Val Ala Glu Leu Gln Arg Leu Lys Met Lys Val Gly Lys
                645                 650                 655

Thr Arg Glu Leu
            660

<210> SEQ ID NO 5
<211> LENGTH: 660
<212> TYPE: PRT
<213> ORGANISM: Hepatitis E virus
<220> FEATURE:
<223> OTHER INFORMATION: hepatitis E virus (HEV) ORF2 capsid protein
      genotype 3

<400> SEQUENCE: 5

Met Arg Pro Arg Ala Val Leu Leu Leu Phe Val Phe Leu Pro Met
1               5                   10                  15

Leu Pro Ala Pro Pro Ala Gly Gln Pro Ser Gly Arg Arg Gly Arg
            20                  25                  30

Arg Ser Gly Gly Ala Gly Gly Phe Trp Gly As

```
Gly Trp Arg Ser Val Glu Thr Gly Val Ala Glu Glu Ala Thr
            260                 265                 270

Ser Gly Leu Val Met Leu Cys Ile His Gly Ser Pro Val Asn Ser Tyr
            275                 280                 285

Thr Asn Thr Pro Tyr Thr Gly Ala Leu Gly Leu Leu Asp Phe Ala Leu
290                 295                 300

Glu Leu Glu Phe Arg Asn Leu Thr Pro Gly Asn Thr Asn Thr Arg Val
305                 310                 315                 320

Ser Arg Tyr Thr Ser Thr Ala Arg His Arg Leu Arg Arg Gly Ala Asp
                325                 330                 335

Gly Thr Ala Glu Leu Thr Thr Thr Ala Ala Thr Arg Phe Met Lys Asp
            340                 345                 350

Leu His Phe Thr Gly Thr Asn Gly Val Gly Glu Val Gly Arg Gly Ile
            355                 360                 365

Ala Leu Thr Leu Phe Asn Leu Ala Asp Thr Leu Leu Gly Gly Leu Pro
            370                 375                 380

Thr Glu Leu Ile Ser Ser Ala Gly Gly Gln Leu Phe Tyr Ser Arg Pro
385                 390                 395                 400

Val Val Ser Ala Asn Gly Glu Pro Thr Val Lys Leu Tyr Thr Ser Val
                405                 410                 415

Glu Asn Ala Gln Gln Asp Lys Gly Ile Thr Ile Pro His Asp Ile Asp
            420                 425                 430

Leu Gly Asp Ser Arg Val Val Ile Gln Asp Tyr Asp Asn Gln His Glu
            435                 440                 445

Gln Asp Arg Pro Thr Pro Ser Pro Ala Pro Ser Arg Pro Phe Ser Val
            450                 455                 460

Leu Arg Ala Asn Asp Val Leu Trp Leu Ser Leu Thr Ala Ala Glu Tyr
465                 470                 475                 480

Asp Gln Thr Thr Tyr Gly Ser Ser Thr Asn Pro Met Tyr Val Ser Asp
                485                 490                 495

Thr Val Thr Phe Val Asn Val Ala Thr Gly Ala Gln Ala Val Ala Arg
            500                 505                 510

Ser Leu Asp Trp Ser Lys Val Thr Leu Asp Gly Arg Pro Leu Thr Thr
            515                 520                 525

Ile Gln Gln Tyr Ser Lys Thr Phe Tyr Val Leu Pro Leu Arg Gly Lys
            530                 535                 540

Leu Ser Phe Trp Glu Ala Ser Thr Thr Lys Ala Gly Tyr Pro Tyr Asn
545                 550                 555                 560

Tyr Asn Thr Thr Ala Ser Asp Gln Ile Leu Ile Glu Asn Ala Ala Gly
                565                 570                 575

His Arg Val Ala Ile Ser Thr Tyr Thr Thr Ser Leu Gly Ala Gly Pro
            580                 585                 590

Thr Ser Ile Ser Ala Val Gly Val Leu Ala Pro His Ser Ala Leu Ala
            595                 600                 605

Ala Leu Glu Asp Thr Val Asp Tyr Pro Ala Arg Ala His Thr Phe Asp
            610                 615                 620

Asp Phe Cys Pro Glu Cys Arg Thr Leu Gly Leu Gln Gly Cys Ala Phe
625                 630                 635                 640

Gln Ser Thr Ile Ala Glu Leu Gln Arg Leu Lys Val Lys Val Gly Lys
                645                 650                 655

Thr Arg Glu Ser
            660
```

```
<210> SEQ ID NO 6
<211> LENGTH: 660
<212> TYPE: PRT
<213> ORGANISM: Hepatitis E virus
<220> FEATURE:
<223> OTHER INFORMATION: hepatitis E virus (HEV) ORF2 capsid protein
      genotype 4

<400> SEQUENCE: 6
```

| | | | | | | | | | | | | | | | |
|---|---|---|---|---|---|---|---|---|---|---|---|---|---|---|---|
| Met | Arg | Ser | Arg | Ala | Phe | Leu | Phe | Leu | Phe | Leu | Val | Leu | Leu | Pro | Met |
| 1 | | | | 5 | | | | | 10 | | | | | 15 | |
| Leu | Pro | Ala | Pro | Ala | Gly | Gln | Pro | Ser | Gly | Arg | Arg | Arg | Gly | Arg | |
| | | | 20 | | | | | 25 | | | | | 30 | | |
| Arg | Ser | Gly | Gly | Ala | Gly | Gly | Phe | Trp | Gly | Asp | Arg | Val | Asp | Ser | |
| | | | 35 | | | | | 40 | | | | | 45 | | |
| Gln | Pro | Phe | Ala | Leu | Pro | Tyr | Ile | His | Pro | Thr | Asn | Pro | Phe | Ala | Ser |
| | 50 | | | | | 55 | | | | | 60 | | | | |
| Asp | Ile | Pro | Ala | Ala | Thr | Gly | Ala | Gly | Ala | Arg | Pro | Arg | Gln | Pro | Ala |
| 65 | | | | | 70 | | | | | 75 | | | | | 80 |
| Arg | Pro | Leu | Gly | Ser | Ala | Trp | Arg | Asp | Gln | Ser | Gln | Arg | Pro | Ala | Thr |
| | | | | 85 | | | | | 90 | | | | | 95 | |
| Ser | Ala | Arg | Arg | Arg | Ser | Ala | Pro | Ala | Gly | Ala | Ser | Pro | Leu | Thr | Ala |
| | | | 100 | | | | | 105 | | | | | 110 | | |
| Val | Ala | Pro | Ala | Pro | Asp | Thr | Gly | Pro | Val | Pro | Asp | Val | Asp | Ser | Arg |
| | | | 115 | | | | | 120 | | | | | 125 | | |
| Gly | Ala | Ile | Leu | Arg | Arg | Gln | Tyr | Asn | Leu | Ser | Thr | Ser | Pro | Leu | Thr |
| | 130 | | | | | 135 | | | | | 140 | | | | |
| Ser | Thr | Thr | Ala | Thr | Gly | Thr | Asn | Leu | Val | Leu | Tyr | Ala | Ala | Pro | Leu |
| 145 | | | | | 150 | | | | | 155 | | | | | 160 |
| Ser | Pro | Leu | Leu | Pro | Leu | Gln | Asp | Gly | Thr | Asn | Thr | His | Ile | Met | Ala |
| | | | | 165 | | | | | 170 | | | | | 175 | |
| Ile | Glu | Ala | Ser | Asn | Tyr | Ala | Gln | Tyr | Arg | Val | Val | Arg | Ala | Thr | Ile |
| | | | 180 | | | | | 185 | | | | | 190 | | |
| Arg | Tyr | Arg | Pro | Leu | Val | Pro | Asn | Ala | Val | Gly | Gly | Tyr | Ala | Ile | Ser |
| | | | 195 | | | | | 200 | | | | | 205 | | |
| Ile | Ser | Phe | Trp | Pro | Gln | Thr | Thr | Thr | Thr | Pro | Thr | Ser | Val | Asp | Met |
| | 210 | | | | | 215 | | | | | 220 | | | | |
| Asn | Ser | Ile | Thr | Ser | Thr | Asp | Val | Arg | Ile | Leu | Val | Gln | Pro | Gly | Ile |
| 225 | | | | | 230 | | | | | 235 | | | | | 240 |
| Ala | Ser | Glu | Leu | Val | Ile | Pro | Ser | Glu | Arg | Leu | His | Tyr | Arg | Asn | Gln |
| | | | | 245 | | | | | 250 | | | | | 255 | |
| Gly | Trp | Arg | Ser | Val | Glu | Thr | Ser | Gly | Val | Ala | Glu | Glu | Ala | Thr | |
| | | | 260 | | | | | 265 | | | | | 270 | | |
| Ser | Gly | Leu | Val | Met | Leu | Cys | Ile | His | Gly | Ser | Pro | Val | Asn | Ser | Tyr |
| | | | 275 | | | | | 280 | | | | | 285 | | |
| Thr | Asn | Thr | Pro | Tyr | Thr | Gly | Ala | Leu | Gly | Leu | Leu | Asp | Phe | Ala | Leu |
| | 290 | | | | | 295 | | | | | 300 | | | | |
| Glu | Leu | Glu | Phe | Arg | Asn | Leu | Thr | Pro | Gly | Asn | Thr | Asn | Thr | Arg | Val |
| 305 | | | | | 310 | | | | | 315 | | | | | 320 |
| Ser | Arg | Tyr | Ser | Ser | Ala | Arg | His | Lys | Leu | Arg | Arg | Gly | Pro | Asp | |
| | | | | 325 | | | | | 330 | | | | | 335 | |
| Gly | Thr | Ala | Glu | Leu | Thr | Thr | Thr | Ala | Ala | Thr | Arg | Phe | Met | Lys | Asp |
| | | | 340 | | | | | 345 | | | | | 350 | | |
| Leu | His | Phe | Thr | Gly | Thr | Asn | Gly | Val | Gly | Glu | Val | Gly | Arg | Gly | Ile |
| | | | 355 | | | | | 360 | | | | | 365 | | |

```
Ala Leu Thr Leu Phe Asn Leu Ala Asp Thr Leu Leu Gly Gly Leu Pro
        370                 375                 380

Thr Glu Leu Ile Ser Ser Ala Gly Gly Gln Leu Phe Tyr Ser Arg Pro
385                 390                 395                 400

Val Val Ser Ala Asn Gly Glu Pro Thr Val Lys Leu Tyr Thr Ser Val
                405                 410                 415

Glu Asn Ala Gln Gln Asp Lys Gly Ile Ala Ile Pro His Asp Ile Asp
            420                 425                 430

Leu Gly Glu Ser Arg Val Val Ile Gln Asp Tyr Asp Asn Gln His Glu
        435                 440                 445

Gln Asp Arg Pro Thr Pro Ser Pro Ala Pro Ser Arg Pro Phe Ser Val
    450                 455                 460

Leu Arg Ala Asn Asp Val Leu Trp Leu Ser Leu Thr Ala Ala Glu Tyr
465                 470                 475                 480

Asp Gln Ser Thr Tyr Gly Ser Ser Thr Asn Pro Met Tyr Val Ser Asp
                485                 490                 495

Thr Val Thr Phe Val Asn Val Ala Thr Gly Ala Gln Gly Val Ser Arg
            500                 505                 510

Ser Leu Asp Trp Ser Lys Val Thr Leu Asp Gly Arg Pro Leu Met Thr
        515                 520                 525

Ile Gln Gln Tyr Ser Lys Thr Phe Phe Val Leu Pro Leu Arg Gly Lys
    530                 535                 540

Leu Ser Phe Trp Glu Ala Gly Thr Thr Lys Ala Gly Tyr Pro Tyr Asn
545                 550                 555                 560

Tyr Asn Thr Thr Ala Ser Asp Gln Ile Leu Ile Glu Asn Ala Ala Gly
                565                 570                 575

Pro Arg Val Cys Ile Ser Thr Tyr Thr Thr Asn Leu Gly Ser Gly Pro
            580                 585                 590

Val Ser Ile Ser Ala Val Gly Val Leu Ala Pro His Phe Ala Leu Ala
        595                 600                 605

Ala Leu Glu Asp Thr Val Asp Tyr Pro Ala Arg Ala His Thr Phe Asp
    610                 615                 620

Asp Phe Cys Pro Glu Cys Arg Ala Leu Gly Leu Gln Gly Cys Ala Phe
625                 630                 635                 640

Gln Ser Thr Val Ala Glu Leu Gln Arg Leu Lys Met Lys Gly Gly Lys
                645                 650                 655

Thr Arg Glu Tyr
            660

<210> SEQ ID NO 7
<211> LENGTH: 11
<212> TYPE: PRT
<213> ORGANISM: Artificial Sequence
<220> FEATURE:
<223> OTHER INFORMATION: synthetic herpes simplex virus glycoprotein D
      B-cell tag epitope

<400> SEQUENCE: 7

Gln Pro Glu Leu Ala Pro Glu Asp Pro Glu Asp
  1               5                  10

<210> SEQ ID NO 8
<211> LENGTH: 10
<212> TYPE: PRT
<213> ORGANISM: Artificial Sequence
<220> FEATURE:
<223> OTHER INFORMATION: synthetic hepatitis E virus (HEV) ORF2 capsid
```

```
protein genotype 1 long proline-rich hinge
connecting S2 domain and P domain, residues
452-461

<400> SEQUENCE: 8

Pro Thr Pro Ser Pro Ala Pro Ser Arg Pro
1               5                   10

<210> SEQ ID NO 9
<211> LENGTH: 15
<212> TYPE: PRT
<213> ORGANISM: Artificial Sequence
<220> FEATURE:
<223> OTHER INFORMATION: synthetic human immunodeficiency virus 1
      (HIV-1) envelope glycoprotein third variable domain P18
      peptide, T helper (Th) neutralization epitope

<400> SEQUENCE: 9

Arg Ile Gln Arg Gly Pro Gly Arg Ala Phe Val Thr Ile Gly Lys
1               5                   10                  15
```